US007083797B2

(12) United States Patent
Content et al.

(10) Patent No.: US 7,083,797 B2
(45) Date of Patent: *Aug. 1, 2006

(54) **32-KDA PROTEIN DERIVED FROM *MYCOBACTERIUM TUBERCULOSIS* AND RELATED PEPTIDES**

(75) Inventors: Jean Content, Rhode St Genese (BE); Lucas De Wit, Puurs (BE); Jacqueline De Bruyn, Beersel (BE); Jean-Paul Van Vooren, St-Pieters Leeuw (BE)

(73) Assignee: N.V. Innogenetics S.A., Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/329,087

(22) Filed: Dec. 23, 2002

(65) Prior Publication Data

US 2003/0225249 A1 Dec. 4, 2003

Related U.S. Application Data

(60) Division of application No. 09/342,673, filed on Jun. 29, 1999, now Pat. No. 6,531,138, which is a continuation of application No. 08/447,430, filed on May 22, 1995, now Pat. No. 5,916,558, which is a continuation of application No. 07/690,949, filed on Jul. 8, 1991, now abandoned.

(30) Foreign Application Priority Data

Sep. 19, 1990 (EP) .................. PCT/EP90/01593

(51) Int. Cl.
*A61K 39/04* (2006.01)
*A61K 39/02* (2006.01)
*A61K 39/00* (2006.01)
*A61K 49/00* (2006.01)

(52) U.S. Cl. ............... 424/248.1; 424/9.1; 424/9.2; 424/184.1; 424/185.1; 424/190.1; 424/234.1; 530/300; 530/350

(58) Field of Classification Search ............ 424/9.1, 424/9.2, 184.1, 185.1, 190.1, 234.1, 248.1; 530/300, 350
See application file for complete search history.

(56) References Cited

U.S. PATENT DOCUMENTS

| 4,299,916 A | 11/1981 | Litman et al. | |
|---|---|---|---|
| 4,683,195 A | 7/1987 | Mullis et al. | |
| 5,916,558 A * | 6/1999 | Content et al. | 424/130.1 |
| 6,531,138 B1 * | 3/2003 | Content et al. | 424/248.1 |

FOREIGN PATENT DOCUMENTS

| BE | A 905 582 | 4/1987 |
|---|---|---|
| EP | 0 288 306 | 10/1988 |

OTHER PUBLICATIONS

K. Matsuo et al., *Journal of Bacteriology*, vol. 170, No. 9, Sep. 1988, pp. 3847-3854, American Society for Microbiology.
H. Tasaka et al., *Chemical Abstracts*, vol. 99, No. 11, Sep. 12, 1983. p. 413, Abstract No. 86251m, Columbus Ohio, US.
M.L. Cohen et al., *Biological Abstracts*, vol. 84, 1987, Abstract No. 56349, Philadelphia, US.
R.A. Young et al., *Proc. Natl. Acad. Sci. USA*, vol. 82, May 1985, pp. 2583-2587.
J. Dr. Bruyn et al., *Microbial Pathogenesis*, vol. 2, 1987, pp. 351-366, Academic Press Inc. (London) Ltd.
H.G. Wiker et al., *Int. Archs. Allergy Appl. Immun.*, vol. 81, 1986, pp. 307-314, S. Karger AG, Basel, DE.
M. Borremans et al., *Infection and Immunity*, vol. 57, No. 10, Oct. 1989, pp. 3123-3130, American Society for Microbiology.
New England Biolabs Catalog (1986/87, New England Biolabs, Beverly, MA, USA), p. 60.
Worsaag et al. (1987). *Inf. and Immiunity*, vol. 55, No. 12, pp. 2922-2927.
Young et al. (1992). *Molecular Microbiology*, vol. 6. No. 2. pp. 133-145.
Audibert et al. (1993), *Immunology Today*, vol. 14, No. 6, pp. 281-284.
Turner et al. (1988). *J. of Clin. Microbiol.*, vol. 26, No. 9, pp. 1714-1719.
Munk et al. (1988), *Eur. J. of Immunol.*, vol. 18, pp. 1835-1838.
Andersen (1994), *Infection and Immunity*, vol. 62, No. 6, pp. 2536-2544.
DeWit et al. (1990), *Nucleic Acids Research*, vol. 18, No. 13, p. 3995.
Wiker et al. (1990). *Infection and Immunity*, vol. 58, No. 1, pp. 272-274.
DeBruyn et al. (1989), *J. of Gen. Microbiology*, vol. 135, pp. 79-84.

* cited by examiner

*Primary Examiner*—Rodney P Swartz
(74) *Attorney, Agent, or Firm*—Fish & Richardson P.C.

(57) ABSTRACT

The invention relates to recombinant polypeptides and peptides and particularly to the polypeptide containing in its polypeptidic chain the following amino acid sequence: the one extending from the extremity constituted by nucleotide at position (1) to the extremity constituted by nucleotide at position (194) represented in FIG. 4a and FIG. 4b. The polypeptides and peptides of the invention can be used for the diagnostic of tuberculosis, and can also be part of the active principle in the preparation of vaccine against tuberculosis.

16 Claims, 60 Drawing Sheets

FIG. 3A

```
 654  ACC-TTC-CTG-ACC-AGC-GAG-CTG-CCG-GGG-TGG-CTG-CAG-GCC-AAC-AGG-CAC-GTC-AAG-CCC-ACC-
  99  thr-phe-leu-thr-ser-glu-leu-pro-gly-trp-leu-gln-ala-asn-arg-his-val-lys-pro-thr- 714  GGA-AGC-GCC-GTC-GTC-GGT-CTT-TCG-ATG-GCT-GCT-TCT-TCG-ACG-CTG-GCG-ATC-GCG-ATC-TAT-
 119  gly-ser-ala-val-val-gly-leu-ser-met-ala-ala-ser-ser-thr-leu-ala-ile-ala-ile-tyr- 774  CAC-CCC-CAG-CAG-TTC-GTC-TAC-GCG-GGA-GCG-ATG-GCG-GGA-CTG-TTG-GAC-CCC-TCC-CAG-GCG-
 139  his-pro-gln-gln-phe-val-tyr-ala-gly-ala-met-ser-gly-leu-leu-asp-pro-ser-gln-ala- 834  ATG-GGT-CCC-ACC-CTG-ATC-GGC-CTG-GCG-ATG-GGT-GAC-GCT-GGC-TAC-AAG-GCC-TCC-GAC-
 159  met-gly-pro-thr-leu-ile-gly-leu-ala-met-gly-asp-ala-gly-tyr-lys-ala-ser-asp- 894  ATG-TGG-GGC-CCG-AAG-GAC-GAG-GAC-CCG-TGG-CAG-CGC-AAC-CCG-CTG-TTG-AAC-GTC-GGG-
 179  met-trp-gly-pro-lys-asp-glu-asp-pro-trp-gln-arg-asn-asp-pro-leu-leu-asn-val-gly- 954  AAG-CTG-ATC-GCC-AAC-AAC-ACC-CGC-GTC-TGG-GTG-TAC-TGC-GGC-AAC-GGC-AAG-CCG-TCG-GAT-
 199  lys-leu-ile-ala-asn-asn-thr-arg-val-trp-val-tyr-cys-gly-asn-gly-lys-pro-ser-asp-
                                     ↓2A 1014  CTG-GGT-GGC-AAC-AAC-CTG-CCG-GCC-AAG-TTC-CTC-GAG-GGC-TTC-GTG-CGG-ACC-AGC-AAC-ATC-
 219  leu-gly-gly-asn-asn-leu-pro-ala-lys-phe-leu-glu-gly-phe-val-arg-thr-ser-asn-ile- 1074  AAG-TTC-CAA-GAC-GCC-TAC-AAC-GCC-GGT-GGN-ZGC -CAC-AAC-GGC-GTG-TTC-GAC-TTC-CCG-GAC-
 239  lys-phe-gln-asp-ala-tyr-asn-ala-gly-gly- a₂ -his-asn-gly-val-phe-asp-phe-pro-asp- 1134  AGC-GGT-ACG-CAC-AGC-TGG-GAG-TAC-TGG-GGC-CAG-CTC-AAC-GCT-ATG-AAG-CCC-GAC-CTG-
 259  ser-gly-thr-his-ser-trp-glu-tyr-trp-gly-gln-leu-asn-ala-met-lys-pro-asp-leu-
                                                                          1242
1194  CAA-CG -CAC-TGG-GTG-CCA-CGC-CCA-ACA-CGC-CCG-GGC-CCG-KCL-CAG-GGC-GCT-TAGCTCCGAACAGACA
 279  gln-arg-a₃ -b₃ -c₃ -d₃ - e₃ - f₃ - a₄-gly-pro-a₅ -gln-gly-ala-TER
                                                                   294
1258  CAACATCTAGCNNCGGTGACCCTTGTGGNNCANATGTTTCCTAAATCCCGTCCCTAGCTCCCGCNGCNNCCGTGTGGTTA 1358
1338  GCTACCTGACNNCATGGGTTT
```

FIG. 3B

CGACACATGCCCAGACACTGCGGAAATGCCACCTTCAGGCCGTCGCTCGGT
CCCGAA TTGGC CGTGAACGACCGCCGG ATAA GGGTTTCGGCGGTGCCGCTTGATGCGGGT

GGACGCCC AAGTTGTGTTGACTACACGAGCACTGCCGGCCCCAGCGCCTGCAGTCTGACCT
AATTCAGG ATG CGCCCAAAC ATG CATGGATGCG TTGAGA ATG AGG AGCA AGA
         -63             -59                              -47
MET-ARG-PRO—ASN-MET-HIS- GLY-CYS-VAL— GLU- MET- ARG-MET—ARG—GLU-ALA—ARG
                 -55                       -49

234  ATG-CAG-CTT-GTT-GAC-AGG-GTT-CGT-GGC-GCC-GTC-ACG-GGT-ATG-TCG-CGT-CGA-CTC-GTG-GTC-
-42  MET-GLN-LEU-VAL-ASP-ARG-VAL-ARG-GLY-ALA-VAL-THR-GLY-MET-SER-ARG-ARG-LEU-VAL-VAL-
                                                        -29

294  GGG-GCC-GTC-GCG -CGC-CTA-GTG-TCG-GGT-CTG-GTC-GGC-GCC-GTC-GGT-GGC-ACG-GCG-ACC-GCG-
-22  GLY-ALA-VAL-ALA - ARG-LEU-VAL-SER-GLY-LEU-VAL-GLY-ALA-VAL-GLY-GLY-THR-ALA-THR-ALA-

354  GGG-GCA-TTT-TCC-CGG-CCG-GGC-TTG-CCG-GTG-GAG-TAC-CTG-CAG-GTG-CCG-TCG-CCG-TCG-ATG-
-2   GLY-ALA-phe-ser-arg-pro-gly-leu-pro-val-glu-tyr-leu-gln-val-pro-ser-pro-ser-met-
     -1  +1

414  GGC-CGT-GAC-ATC-AAG)-GTC-CAA-TTC-CAA-AGT-GGT-GCC-AAC-TCG-CCC-GCC-CTG-TAC-CTG-
19   gly-arg-asp-ile-lys -val-gln-phe-gln-ser-gly-ala-asn-ser-pro-ala-leu-tyr-leu-
                        ↓ 17

474  CTC-GAC-GGC-CTG-CGC-GCG-CAG-GAC-GAC-TTC-AGC-GGC-TGG-GAC-ATC-AAC-ACC-CCG-GCG-TTC-
39   leu-asp-gly-leu-arg-ala-gln-asp-asp-phe-ser-gly-trp-asp-ile-asn-thr-pro-ala-phe- 534  GAG-TGG-TAC-GAC-CAG-CAG-TCG-GTG-CCG-GTG-ATG-CCG-GTG-GGT-GGC-CAG-TCA-AGC-TTC-
59   glu-trp-tyr-asp-gln-gln-ser-val-val-met-pro-val-gly-gly-gln-ser-ser-phe- 594  TAC-TCC-GAC-TGG-TAC-CAG-CCC-GCC-TGC-CGC-AAG-GCC-GGT-TGC-CAG-(ACT-TAC-AAG-TGG-GAG-
79   tyr-ser-asp-trp-tyr-gln-pro-ala-cys-arg-lys-ala-gly-cys-gln- thr-tyr-lys-trp-glu-

FIG. 4A

```
654   ACC-TTC-CTG-ACC-AGC-GAG-CTG-CCG-GGG-TGG-CTG-CAG-GCC-AAC-AGG-CAC-GTC-AAG-CCC-ACC-
 99   thr-phe-leu-thr-ser-glu-leu-pro-gly-trp-leu-gln-ala-asn-arg-his-val-lys-pro-thr- 714   GGA-AGC-GCC-GTC-GTC-GGT-CTT-TCG-ATG-GCT-GCT-TCT-TCG-GCG-CTG-ACG-CTG-GCG-ATC-TAT-
119   gly-ser-ala-val-val-gly-leu-ser-met-ala-ala-ser-ser-ala-leu-thr-leu-ala-ile-tyr- 774   CAC-CCC-CAG-CAG-TTC-GTC-TAC-GCG-GGA-GCG-ATG-TCG-GGC-CTG-TTG-GAC-CCC-TCC-CAG-GCG-
139   his-pro-gln-gln-phe-val-tyr-ala-gly-ala-met-ser-gly-leu-leu-asp-pro-ser-gln-ala- 834   ATG-GGT-CCC-ACC-CTG-ATC-GGC-CTG-GCG-ATG-GGT-GAC-GCT-GGC-TAC-AAG-GCC-TCC-GAC-
159   met-gly-pro-thr-leu-ile-gly-leu-ala-met-gly-asp-ala-gly-tyr-lys-ala-ser-asp- 894   ATG-TGG-GGC-CCG-AAG-GAG-GAC-CGC-TGG-CAG-CGC-AAC-GAC-CCG-CTG-TTG-AAC-GTC-GGG-
179   met-trp-gly-pro-lys-glu-asp-pro-ala-trp-gln-arg-asn-asp-pro-leu-leu-asn-val-gly- 954   AAG-CTG-ATC-GCC-AAC-AAC-ACC-CGC-GTC-GTG-TAC-TGC-GGC-AAC-GGC-AAG-CCG-TCG-GAT-
199   lys-leu-ile-ala-asn-asn-thr-arg-val-tyr-cys-gly-asn-gly-lys-pro-ser-asp-
                                                    ↓ 24

1014  CTG-GGT-GGC-AAC-AAC-CTG-CCG-GCC-AAG-TTC-CTC-GAG-GGC-TTC-GTG-CGG-ACC-AGC-AAC-ATC-
219   leu-gly-gly-asn-asn-leu-pro-ala-lys-phe-leu-glu-gly-phe-val-arg-thr-ser-asn-ile- 1074  AAG-TTC-CAA-GAC-GCC-TAC-AAC-GCC-GGT-GGG- CGC-CAC-AAC-GCC-GTG-TTC-CCG-GAC-
239   lys-phe-gln-asp-ala-tyr-asn-ala-gly-gly- arg-his-asn-gly-val-phe-pro-asp- 1134  AGC-GGT-ACG-CAC-AGC-TGG-GAG-TAC-TGG-GGC-CAG-CTC-AAC-GCT-ATG-AAG-CCC-GAC-CTG-
259   ser-gly-thr-his-ser-trp-glu-tyr-trp-gly-gln-leu-asn-ala-met-lys-pro-asp-leu-
                                                                         1242
1194  CAA-CG -CAC-TGG-GTG-CCA-CGC-GTG-CCA-CGC-GGC-CCG-CAG-GGC-GCt-TAGCTCCGAACAGACA
279   gln-arg- his-trp-val-pro-arg -pro-thr-pro-arg -pro-thr-pro-gln-gly-ala-TER
                                                                         294

1258  CAACATCTAGCNNCGGTGACCCTTGTGNNCANATGTTCCTAAATCCGTCCCTAGCTCCCGCNGCNNCCGTGTGGTTA
1338  GCTACCTGACNNCATGGGTTT 1358
```

FIG. 4B

```
  1    ACT-GCC-GGG-CCC-AGC-GCC-TGC-AGT-GCC-TGC-ACC-TAA-TTC-AGG-ATG-CGC-CCA-AAC-ATG-CAT-GGA-
 61    TGC-GTT-GAG-ATG-AGG-ATG-AGG-GAA-GCA-AGA-ATG-CAG-CTT-GTT-GAC-CTT-GTT-CGT-GGC-GCC-
       MET-GLN-LEU-VAL-VAL-ASP-ARG-VAL-ARG-GLY-ALA-
       (-43)
121    GTC-ACG-GGT-ATG-TCG-CGT-CGA-CTC-GTG-GTC-GGC-GCC-GTC-GGG-GCC-GCC-CTA-GTG-TCG-GGT-
 -33   VAL-THR-GLY-MET-SER-ARG-ARG-LEU-VAL-VAL-GLY-ALA-VAL-VAL-GLY-ALA-ALA-LEU-VAL-SER-GLY-
181    CTG-GTC-GGC-GCC-GTC-GGT-GGC-ACG-GCG-GGG-GCA-TTT-TCC-CGG-CCG-GGC-TTG-CCG-
 -13   LEU-VAL-GLY-ALA-VAL-GLY-GLY-THR-ALA-GLY-ALA-phe-ser-arg-pro-gly-leu-pro-
                                                  +1
241    GTG-GAG-TAC-CTG-CAG-GTG-CCG-TCG-CCG-ATG-GGC-CGT-GAC-ATC-AAG-GTC-CAA-TTC-CAA-
   8   val-glu-tyr-leu-gln-val-pro-ser-pro-met-gly-arg-asp-ile-lys-val-gln-phe-gln-
                                                                           ↓17
301    AGT-GGT-GCC-AAC-TCG-CCC-GCC-CTG-TAC-CTC-GAC-GGC-CTG-CGC-GCG-CAG-GAC-GAC-
  28   ser-gly-gly-ala-asn-ser-pro-ala-leu-tyr-leu-asp-gly-leu-arg-ala-gln-asp-asp-
361    TTC-AGC-GGC-TGG-GAC-ATC-AAC-ACC-CCG-GCG-TTC-GAG-TGG-TAC-GAC-CAG-TCG-GGC-CTG-TCG-
  48   phe-ser-gly-trp-asp-ile-asn-thr-pro-ala-phe-glu-trp-tyr-asp-gln-ser-gly-leu-ser-
421    GTG-GTC-ATG-CCG-GTG-GGT-GGC-CAG-TCA-GTC-GGT-TAC-TCC-GAC-TGG-TAC-CAG-CCC-GCC-TGC-
  68   val-val-met-pro-val-gly-gly-gln-ser-ser-phe-ser-asp-trp-tyr-gln-pro-ala-cys-
481    GGC-AAG-GCC-GGT-TGC-CAG-ACT-TAC-AAG-TGG-GAG-ACC-TTC-CTG-ACC-AGC-GAG-CTG-CCG-GGG-
  88   gly-lys-ala-gly-cys-gln-thr-tyr-lys-trp-glu-thr-phe-leu-thr-ser-glu-leu-pro-gly-
```

FIG. 5A

```
541  TGG-CTG-CAG-GCC-AAC-AGG-CAC-GTC-AAG-CCC-ACC-GGA-AGC-GCC-GTC-GTC-GGT-CTT-TCG-ATG-
108  trp-leu-gln-ala-asn-arg-his-val-lys-pro-thr-gly-ser-ala-val-val-gly-leu-ser-met- 601  GCT-GCT-TCT-TCG-GCG-CTG-ACG-CTG-GCG-ATC-TAT-CAC-CCC-CAG-CAG-TTC-GTC-TAC-GCG-GGA-
128  ala-ala-ser-ser-ala-leu-thr-leu-ala-ile-tyr-his-pro-gln-gln-phe-val-tyr-ala-gly- 661  GCG-ATG-TCG-GGC-CTG-TTG-GAC-CCC-CAG-GCG-ATG-GGT-CCC-ACC-CTG-ATC-GGC-CTG-GCG-
148  ala-met-ser-gly-leu-leu-asp-pro-ser-gln-ala-met-gly-pro-thr-leu-ile-gly-leu-ala- 721  ATG-GGT-GAC-GCT-GGC-GGC-TAC-AAG-GCC-TCC-GAC-ATG-TGG-GGC-CCG-AAG-GAG-GAC-CCG-GCG-
168  met-gly-asp-ala-gly-gly-tyr-lys-ala-ser-asp-met-trp-gly-pro-lys-glu-asp-pro-ala- 781  TGG-CAG-CGC-AAC-GAC-CCG-CTG-TTG-AAC-GTC-GGG-AAG-CTG-ATC-GCC-AAC-AAC-ACC-CGC-GTC-
188  trp-gln-arg-asn-asp-pro-leu-leu-asn-val-gly-lys-leu-ile-ala-asn-asn-thr-arg-val- 841  TGG-GTG-TAC-TGC-GGC-AAC-GGC-AAG-CCG-TCG-GAT-CTG-GGT-GGC-AAC-AAC-CTG-CCG-GCC-AAG-
208  trp-val-tyr-cys-gly-asn-gly-lys-pro-ser-asp-leu-gly-gly-asn-asn-leu-pro-ala-lys- 901  TTC-CTC-GAG-GGC-TTC-GTG-CGG-ACC-AGC-AAC-ATC-AAG-TTC-CAA-GAC-GCC-TAC-AAC-GCC-GGT-
228  phe-leu-glu-gly-phe-val-arg-thr-ser-asn-ile-lys-phe-gln-asp-ala-tyr-asn-ala-gly- 961  GGC-GGC-CAC-AAC-GGC-GTG-TTC-GAC-TTC-CCG-GAC-AGC-GGT-ACG-CAC-AGC-TGG-GAG-TAC-TGG-
248  gly-gly-his-asn-gly-val-phe-asp-phe-pro-asp-ser-gly-thr-his-ser-trp-glu-tyr-trp-
```

FIG. 5B

```
1021  gg[C]-GCG-CAG-CTC-AAC-GCT-ATG-AAG-CCC-GAC-CTG-CAA-CGG-GCA-CTG-GGT-GCC-ACG-CCC-AAC-
268       gly-ala-gln-leu-asn-ala-met-lys-pro-asp-leu-gln-arg-ala-leu-gly-ala-thr-pro-asn-
                                                                        (1104)
1081  ACC-GGG-CCC-GCG-CCC-CAG-GGC-GCC-TAG-CTC-CGA-ACA-GAC-ACA-ACA-TCT-AGC-GGC-GGT-GAC-
288       thr-gly-pro-ala-pro-gln-gly-ala-TER
                                    (295)
1141  CCT-TGT-GGT-CGC-CGC-CGT-AGA-TGT-TTC-CTA-AAT-CCC-GTC-CCT-AGC-TCC-CGC-CGC-GGG-CCG-
1201  TGT-GGT-TAG-CTA-CCT-GAC-GGG-GTT-GGC-CGG-GGC-GGT-TGA-CGC-CGG-GTG-CAC-ACA-
1261  GCC-TAC-ACG-AAC-GGA-AGG-TGG-ACA-CAT-GAA-GGG-TCG-GTC
                                                    (1299)
```

FIG. 5C

```
M. tub.              VDRVRGAVTGMSRRLVVGAVGAALVSGLVGAVGGTATAGAFSRPGLPVEYLQVPSPSMGR
                             .  ::.: :::::::::::::::::::::::::::::::::::::::  60
 BCG       MTDVSRKIRAWGRRLMIGTAAAVVLPGLVGLAGGAATAGAFSRPGLPVEYLQVPSPSMGR
                10        20        30        40        50        60

DIKVQFQSGGANSPALYLLDGLRAQDDFESGWDINTPAFEWYDQSGLSVVMPVGGQSSFYS
           ::::::::::::.:::::::::::::::.::::::::::::::.::::::.::::::::  120
           DIKVQFQSGGNNSPAVYLLDGLRAQDDYNGWDINTPAFEWYYQSGLSIVMPVGGQSSFYS
                70        80        90       100       110       120

DWYQPACGKAGCQTYKWETFLTSELPGWLQANRHVKPTG--SAVVGLSMAASSALTLAIY
           :::.::::::::::::::::.::::::.:::::.:::::  :::::::::.:::.::::  180
           DWYSPACGKAGCQTYKWETLLTSELPQWLSANRAVKPTGSPSAAIGLSMAGSSAMILAAY
                130       140       150       160       170       180

HPQQFVYAGAMSGLLDPSQAMGPTLIGLAMGDAGGYKASDMWGPKEDPAWQRNDPLLNVG
           ::::::.::.:::::::::: :::  :::::::::::::::.::::::.:::::   .
           HPQQFIYAGSLSALLDPSQGMG--LIGLAMGDAGGYKAADMWGPSSDPAWERNDPTQQIP
                190       200       210       220       230
```

FIG. 7A

```
                    250         260         270         280         290         300
          KLIANNTRVWVYCGNGKPSDLGGNNLPAKFLEGEVRTSNIKFQDAYNAGGGHNGVFDFPD
          :: ::::::::::::::  ::::::::: ::::::: ::::::::::: :: ::
          KLVANNTRLWVYCGNGTPNELGGANIPAEFLENFVRSSNLKFQDAYKPAGGHNAVFNFPP
                    240         250         260         270         280         290

310         320
          SGTHSWEYWGAQLNAMKPDLQRALGA
          : ::::::::::::::: ::  ::X
          NGTHSWEYWGAQLNAMKGDLQSSLGA
                  300         310         320
```

FIG. 7B

```
                PROBE REGION A
  1    ATG CAGCTTGTTGACAGGGTTCGTGGCGCCGTCACGGGTATGTCGCGTCGACTC
       ||| ||||||||||||||||||||||||||||||||||||||||||||||||||
  1    ATG CAGCTTGTTGACAGGGTTCGTGGCGCCGTCACGGGTATGTCGCGTCGACTC
       |||    ||  | |     |||||    ||| | ||  | ||
  1    ATG ACAGACGTGAGCCGAAAGATTCGAG CTT    GGGGACGCCG ATTGA TG

55    GTGGTCGGGGCCGTCGGCGCGGCCCTAGTGTCGGGTCTGGTCGGCGCCGTCGGTG
       ||||||||||||||| |||||  |||||||||||||||||||||||||||||||
 55    GTGGTCGGGGCCGTC GCGCG  CCTAGTGTCGGGTCTGGTCGGCGCCGTCGGTG
       | |  ||| |  ||       |  |   |||| ||||| ||    | ||| |
 49    ATCGGCACGGCAGCG GCTGT    AGTCCTTCCGGGCCTGGTGGGGCTTGCCGGCG

P1
110    GCA CGGCGACCGCGGGGGCATTTTCCCGGCCGGGCTTGCCGGTG GAGTACCTG
       |||  ||||||||||||||||||||||||||||||||||||||||| |||||||||
107    GCA CGGCGACCGCGGGGGCATTTTCCCGGCCGGGCTTGCCGGTG GAGTACCTG
       |   ||||  ||||| || || |||||||||| || |||||  |   |||||||||
101    GAG CGGCAACCGCGGGCGCGTTCTCCCGGCCGGGGCTGCCGGTC GAGTACCTG

163    CAGGTGCCGTCGCCGTCGATGGGCCG TGACATCAAGGTCCAATTCCAAAGTGGT
       ||||||||||||||||||||||||||| ||||||||||||||||||||||||||||
160    CAGGTGCCGTCGCCGTCGATGGGCCG TGACATCAAGGTCCAATTCCAAAGTGGT
       |||||||||||||||||||||||||| ||||||||||| |||||| || |||
154    CAGGTGCCGTCGCCGTCGATGGGCCG CGACATCAAGGTTCAGTTCCAGAGCGGT

PROBE REGION B
217    GGTGCCAAC TCGCCCGCCCTGTACCTG CTCGACGGCCTGCGCGCGCAGGACGA
       |||||||||  ||||||||||||||||| |||||||||||||||||||||||||||
214    GGTGCCAAC TCGCCCGCCCTGTACCTG CTCGACGGCCTGCGCGCGCAGGACGA
       ||   ||||  || ||  ||  |  ||| |||||||||||||||||  || ||||
208    GGGAACAAC TCACCTGCGGTTTATCTG CTCGACGGCCTGCGCGCCCAAGACGA
```

FIG. 9A

```
                               P2
270   CTTCAGCGGCTGGGAC|ATCAACACCCCGGCGTTCGAGTGGTAC|GACCAGTCGG
      ||||||||||||||||  ||||||||||||||||||||||||||| |||||||||
267   CTTCAGCGGCTGGGAC|ATCAACACCCCGGCGTTCGAGTGGTAC|GACCAGTCGG
      || ||  |||||||||  ||||||||||||||||||||||||||| ||||||||
261   CTACAACGGCTGGGAT|ATCAACACCCCGGCGTTCGAGTGGTAC|TACCAGTCGG

323   GCCTGTCGGTGGTCATGCCGGTGGGTGGCCAGTCAAGCTTCTACTCCGACTGGTA
      |||||||||||||||||||||||||||||||||||||||||||||||||||||||
320   GCCTGTCGGTGGTCATGCCGGTGGGTGGCCAGTCAAGCTTCTACTCCGACTGGTA
      | ||||||  | ||||||||| || || ||||| ||||||||  ||||||||||
314   GACTGTCGATAGTCATGCCGGTCGGCGGGCAGTCCAGCTTCTACAGCGACTGGTA

P3                     P4
378   CCAGCCCGCCTGCGGCAAGGCCGGT|TGCCAGACTTACAAGTGGGA|GACCT|TC
      ||||||||||||| ||||||||||| |||||||||||||||||||| ||||| ||
375   CCAGCCCGCCTGCCGCAAGGCCGGT|TGCCAGACTTACAAGTGGGA|GACCT|TC
      |  || ||||||| |||||  ||   ||||||||||||||||||||  |||   ||
369   CAGCCCGGCCTGCGGTAAGGCTGGC|TGCCAGACTTACAAGTGGGA|AACCC|TC

430   |CTGACCAGCGAGCTGCCG|GGGTGGCTGCAGGCCAACAGGCACGTCAAGCCCACC
       ||||||||||||||||||  ||||||||||||||||||||||||||||||||||||
427   |CTGACCAGCGAGCTGCCG|GGGTGGCTGCAGGCCAACAGGCACGTCAAGCCCACC
       ||||||||||||||||||  ||| ||  ||||||||||  |||  |||||||||
421   |CTGACCAGCGAGCTGCCG|CAATGGTTGTCCGCCAACAGGGCCGTGAAGCCCACC

PROBE REGION C
484   GGAAGCGCCGTCGTCGGTCTTTCGATGGCTGCTTCTTCG|GCGCTGACGCTGGCG|
      |||||||||||||||||||||||||||||||||||||||  |||||||||||||||
481   GGAAGCGCCGTCGTCGGTCTTTCGATGGCTGCTTCTTCG|GCGCTGACGCTGGCG|
      || |||||  ||||  |  ||||||||| || ||| || |  ||  |||   ||||
475   GGCAGCGCTGCAATCGGCTTGTCGATGGCCGGCTCGTCG GCAATGATCTTGGCC
```

FIG. 9B

```
538  ATCTATC ACCCCCAGCAGTTCGTCTACGCGGGAGCGATGTCGGGCCTGTTGGAC
     |||||||  ||||||||||||||||||||||||||||||||||||||||||||
535  ATCTATC ACCCCCAGCAGTTCGTCTACGCGGGAGCGATGTCGGGCCTGTTGGAC
     ||| |   ||||||||||||||| ||||||| ||  |||||| |||| |||||
529  GCCTACC ACCCCCAGCAGTTCATCTACGCCGGCTCGCTGTCGGCCCTGCTGGAC

P5
592  CCCTCCCAGGCGATGGGTCCCAC CCTGATCGGCCTGGCGATGGGTGACGC TGG
     ||||||||||||||||||||||| |||||||||||||||||||||||||||  |||
589  CCCTCCCAGGCGATGGGTCCCAC CCTGATCGGCCTGGCGATGGGTGACGC TGG
     ||||| |||| ||||||       |||||||||| ||||||||||||||    ||
583  CCCTCTCAGGGGATGGG       CCTGATCGGCCTCGCGATGGGTGACGC CGG

645  CGGCTACAAGGCCTCCGACATGTGGGGCCCGAAGGAGGACCCGGCGTGGCAGCGC
     ||||||||||||||||||||||||||||||||||||||||||||||||||||||
642  CGGCTACAAGGCCTCCGACATGTGGGGCCCGAAGGAGGACCCGGCGTGGCAGCGC
     ||| ||||||||| | ||||||||||| ||  |        |||||||| ||||||
631  CGGTTACAAGGCCGCAGACATGTGGGGTCCCTCGAGTGACCCGGCATGGGAGCGC

PROBE REGION D
700  AACGAC CCGCTGTTGAACGTCGGGAAG CTGATCGCCAACAACACCCGCGTCTG
     ||||||  |||||||||||||||||||| ||||||||||||||||||||||||||
697  AACGAC CCGCTGTTGAACGTCGGGAAG CTGATCGCCAACAACACCCGCGTCTG
     ||||||  ||  |  | ||  ||| ||| |||  ||||  ||||||||||   | ||
686  AACGAC CCTACGCAGCAGATCCCCAAG CTGGTCGCAAACAACACCCGGCTATG

PROBE REGION E
753  GGTGTACTGCGGCAACGGC AAGCCGTCGGATCTGGGTGGCAAC AACCTGCCGG
     |||||||||||||||||||||||||||||||||||||||||||||||| ||||||||||
750  GGTGTACTGCGGCAACGGC AAGCCGTCGGATCTGGGTGGCAAC AACCTGCCGG
     ||| || |||||| |||||| |   | ||||  | | |||  ||||  |||  ||  ||
739  GGTTTATTGCGGGAACGGC ACCCCGAACGAGTTGGGCGGTGCC AACATACCCG
```

FIG. 9C

```
806    CCAAGTTCCTCGAGGGCTTCGTGCGGACCAGCAACATCAAGTTCCAAGACGCCTA
       ||||||||||||||||||||||||||||||||||||||||||||||||||||||
803    CCAAGTTCCTCGAGGGCTTCGTGCGGACCAGCAACATCAAGTTCCAAGACGCCTA
       || |||||| | |||  |||||| || | |||||||| | |||||||| || || ||
792    CCGAGTTCTTGGAGAACTTCGTTCGTAGCAGCAACCTGAAGTTCCAGGATGCGTA
```

```
                                                            P6
861    CAACGCCGGTGGCGGCCACAACGGCGTGTTCGACTTCCCGGACAGCGGT |ACGCA
       ||||||||||||   ||||||||||||||||||||||||||||||||||| |||||
858    CAACGCCGGTGGGCGCCACAACGGCGTGTTCGACTTCCCGGACAGCGGT |ACGCA
       |||   |||   ||  | ||||||||  |||||||  |||||||  || ||| |||||
847    CAAGCCCGCGGGCGGGCACAACGCCGTGTTCAACTTCCCGCCCAACGGC |ACGCA
```

```
915    CAGCTGGGAGTACTGGGGCGC| GCAGCTCAACGCTATGAAGCCCGACCTGCA |AC
       ||||||||||||||||||||| |||||||||||||||||||||||||||||||  ||
912    CAGCTGGGAGTACTGGGGCGC| GCAGCTCAACGCTATGAAGCCCGACCTGCA |AC
       ||||||||||||||||||||| |||||||||| ||||||   ||||||| |    |
901    CAGCTGGGAGTACTGGGGCGC| TCAGCTCAACGCCATGAAGGGTGACCTGCAGAG
```

```
       PROBE REGION F
968    GGGCACTGGGTGCCACGCCCAACACCGGGCCCGCGCCCCAGGG] CGCCTAG
       ||||||||||||||||||||||||||||||||||||   ||||  ||  |||||||
965    GGCACTGGGTGCCACGCCCAACACCGGGCC   CGCCGCAGGG] CGCCTAG
         |  | || ||| ||  ||  |
955    TTCGTTAGGCGCC  GGCTGA
```

FIG. 9D

From: PIGRI

```
      3         9        15        21        27        33        39        45
      -         -         -         -         -         -         -         -
  1 TTC CGG GGA TCT CTC ACC TAC CAA ACA ATG CCC CCC TGC AAA AAA
    AAG GCC CCT AGA GAG TGG ATG GTT TGT ACG GGG GGG ACG TTT TTT

46 TAA ATT CAT ATA AAC ATA CAG ATA ACC ATC TGC GGT GAT AAA
    ATT TAA GTA TAT TTT TGT GTC TAT TGG TAG ACG CCA CTA TTT

91 TTA TCT CTG GCG GTG TTG ACA TAA ATA CCA CTG GCG GTG ATA CTG
    AAT AGA GAC CGC CAC AAC TGT ATT TAT GGT GAC CGC CAC TAT GAC

136 AGC ACA TCA GCA GGA CGC ACT GAC CAC CAT GAA CTT GAC CTG CTT
    TCG TGT AGT CGT CCT GCG TGA CTG GTG GTA CTT CTG CGA GAA

181 AAA AAT AAT TAA GCC AAG GGC ATT GGT ACC AGG GGT TTT AAA
    TTT TTA ATT CGG TTC CCG TAA TAA CCA TCC TCC AAA TTT

226 TCA TGG TAA GAT CAA GTA GTC AAA ATT CGA GTG ACA AGC CTG TAG
    AGT ACC ATT CTA GTT CAT CAG TTT AAT GCT CAC TGT TCG GAC ATC

271 CCC ACG TCG TAG CAA ACC AAG TGG AGG AGC AGT AAC CAT GGT
    GGG TGC AGC ATC GTT TGG TTC ACC TCG TCG TCA TTG GTA CCA

316 TAC TGG AGA AGG GGG ACC TCA GCG CTG AGG TCA ATC TGC CCA
    ATG ACC TCT TCC CCC TGG TTG AGT CGC GAC TCC AGT TAG ACG GGT
```

FIG. 10B

```
361 AGT CTA GAG TCG ACC TGC AGC CCA AGC TTG GCT GTT TTG GCG GAT
    TCA GAT CTC AGC TGG ACG TCG GGT TCG AAC CGA CAA AAC CGC CTA

406 GAG AGA AGA TTT TCA GCC TGA TAC AGA TTA AAT CAG AAC GCA GAA
    CTC TCT TCT AAA AGT CGG ACT ATG TCT AAT TTA GTC TTG CGT CTT

451 GCG GTC TGA TAA AAC AGA ATT TGC CTG GCG GCA GTA GCG CGG TGG
    CGC CAG ACT ATT TTG TCT TAA ACG GAC CGC CGT CAT CGC GCC ACC

496 TCC CAC CTG ACC CCA TGC CGA ACT CAG AAG TGA AAC GCC GTA GCG
    AGG GTG GAC TGG GGT ACG GCT TGA GTC TTC ACT TTG CGG CAT CGC

541 CCG ATG GTA GTG TGG GGT CTC CCC ATG CGA GAG TAG GGA ACT GCC
    GGC TAC CAT CAC ACC CCA GAG GGG TAC GCT CTC ATC CCT TGA CGG

586 AGG CAT CAA ATA AAA CGA AAG GCT CAG TCG AAA GAC TGG GCC TTT
    TCC GTA GTT TAT TTT GCT TTC AGT CAG CTG TTT CTG ACC CGG AAA

631 CGT TTT ATC TGT TGT ACA AAC GCT GTG AAC GCT CTC CTG AGT AGG ACA
    GCA AAA TAG ACA ACA TGT TTG CAC TTG CGA GAG GAC TCA TCC TGT

676 AAT CCG CCG GGA GCG GAT TTG AAC GTT GCG AAG CAA CGG CCC GGA
    TTA GGC GGC CCT CGC CTA AAC TTG CAA CGC TTC GCC GGG CCT

721 GGG TGG CGG GCA GGA CGC CCG CCA TAA ACT GCC AGG CAT CAA ATT
    CCC ACC GCC CGT CCT GCG GGC GGT ATT TGA CGG TCC GTA GTT TAA
```

FIG. 10C

```
 766 AAG CAG AAG GCC ATC CTG ACG GAT GGC CTT TTT AAA TTT GCG TTT CTA CAA
     TTC GTC TTC CGG TAG GAC TGC CTA CCG GAA AAA TTT CGC AAA GAT GTT

811 ACT CTT TTG TTT ATT TTT CTA AAT ACA TTC AAA TAT GTA TCC GCT
     TGA GAA AAC AAA TAA AAA GAT TTA TGT AAG TTT ATA CAT AGG CGA

856 CAT GAG ACA ATA ACC CTG ATA AAT GCT TCA ATA AAA GGA TCT
     GTA CTC TGT TAT TGG GAC TAT TTA CGA AGT TAT TTT CCT AGA

901 AGG TGA AGA TCC TTT TTG ATA ATC TCA TGA CCA AAA TCC CTT AAC
     TCC ACT TCT AGG AAA AAC TAT TAG AGT ACT GGT TTT AGG GAA TTG

946 GTG AGT TTT CGT TCC ACT GAG CGT CAG ACC CCG TAG AAA AGA TCA
     CAC TCA AAA GCA AGG TGA CTC GCA GTC TGG GGC ATC TTT TCT AGT

991 AAG GAT CTT CTT GAG ATC CTT TTT TTC TGC GCG TAA TCT GCT GCT
     TTC CTA GAA GAA CTC TAG GAA AAA AAG ACG CGC ATT AGA CGA CGA

1036 TGC AAA CAA AAA AAC CAC CGC TAC CAG CGG TGG TTT GTT TGC CGG
     ACG TTT GTT TTT TTG GTG GCG ATG GTC GCC ACC AAA CAA ACG GCC
```

FIG. 10D

```
1081 ATC AAG AGC TAC CAA CTC TTT TTC CGA AGG TAA CTG GCT TCA GCA
     TAG TTC TCG ATG GTT GAG AAA AAG GCT TCC ATT GAC CGA AGT CGT

1126 GAG CGC AGA TAC CAA ATA CTG TCC TTC TAG TGT AGC CGT AGT TAG
     CTC GCG TCT ATG GTT TAT AGG AAG ATC ACA TCG GCA TCA ATC

1171 GCC ACC ACT TCA AGA ACT CTG TAG CAC CGC CTA CAT ACC TCG CTC
     CGG TGG TGA AGT TCT TGA GAC ATC GTG GCG GAT GTA TGG AGC GAG

1216 TGC TAA TCC TGT TAC CAG TGG CTG CTG CCA GTG GCG ATA AGT CGT
     ACG ATT AGG ACA ATG GTC ACC GAC GAC GGT CAC CGC TAT TCA GCA

1261 GTC TTA CCG GGT TGG ACT CAA GAC GAT AGT TAC CGG ATA AGG CGC
     CAG AAT GGC CCA ACC TGA GTT CTG CTA TCA ATG GCC TAT TCC GCG

1306 AGC GGT CGG GCT GAA CGG GGG GTT CGT GCA CAC AGC CCA GCT TGG
     TCG CCA GCC CGA CTT GCC CCC CAA GCA CGT GTG TCG GGT CGA ACC

1351 AGC GAA CGA CCT ACA CCG AAC TGA GAT ACC TAC AGC GTG AGC ATT
     TCG CTT GCT GGA TGT GGC TTG ACT CTA TGG ATG TCG CAC TCG TAA
```

FIG. 10E

```
1396  GAG AAA GCG CCA CGC TTC CCG AAG GGA GAA AGG CGG ACA GGT ATC
      CTC TTT CGC GGT GCG AAG GGC TTC CCT CTT TCC GCC TGT CCA TAG

1441  CGG TAA GCG GCA CGC TCG GAA CAG GAG AGC GCA CGA GGG AGC TTC
      GCC ATT CGC CGT AGC CTT GTC CTC TCG CGT GCT CCC TCG AAG

1486  CAG GGG GAA ACG CCT GGT ATC TTT ATA GTC CTG TCG GGT TTC GCC
      GTC CCC CTT TGC GGA CCA TAG AAA TAT CAG GAC CCA AAG CGG

1531  ACC TCT GAC TTG AGC GTC GAT TTT TGT GAT GCT CGT CAG GGG GGC
      TGG AGA CTG AAC TCG CAG CTA AAA ACA CTA CGA GCA GTC CCC CCG

1576  GGA GCC TAT GGA AAA ACG CCA GCA ACG CGG CCT TTT TAC GGT TCC
      CCT CGG ATA CCT TTT TGC GGT CGT TGC GCC GGA AAA ATG CCA AGG
```

FIG. 10F

```
1621 TGG CCT TTT GCT GGC CTT TTG CTC ACA TGT TCT TTC CTG CGT TAT
     ACC GGA AAA CGA CCG GAA AAC GAG TGT ACA AGA AAG GAC GCA ATA

1666 CCC CTG ATT CTG TGG ATA ACC GTA TTA CCG CCT TTG AGT CAG CTG
     GGG GAC TAA GAC ACC TAT TGG CAT AAT GGC GGA AAC TCA CTC GAC

1711 ATA CCG CTC GCC GCA GCC GAA CGA CCG AGC GCA GCG AGT CAG TGA
     TAT GGC GAG CGG CGT CGG CTT GCT GGC TCG CGT TCA GTC ACT

1756 GCG AGG AAG CGG AAG AGC GCT GAC CTG TTC CGC GTT CCT GTC GCA
     CGC TCC TTC GCC TTC TCG CGA CTG GAC AAG AGG TCT CAA CAG CGT

1801 GAA ACA CGG AAA CCG AAG ACC ATT CAT GTT GCT CAG CCT ATC GGT
     CTT TGT GCC TTT GGC TTC TGG TAA GTA CAA CGA GTC GGA TAG CCA

1846 GAC GTT TTG CAG CAG TCG CTT CAC CCC CGC TCG CGT AGC CGG
     CTG CAA AAC GTC GTC AGC GAA GTG GGG GCG AGC GCA TCG GCC

1891 GAT TCA TTC TGC TAA CCA GTA AGG CAA CCC CGC CAG AGC GCC
     CTA AGT AAG ACG ATT GGT CAT TCC GTT GGG GCG GTC TCG GCC
```

FIG. 10G

```
1936  GTC CTC AAC GAC AGG AGC ACG ATC ATG CGC ACC CGT GGC CAC GAC
      CAG GAG TTG CTG TCC TCG TGC TAG TAC GCG TGG GCA CCG GTC CTG

1981  CCA ACG CTG CCC GAG ATG CGC GTG CGC CGG CTG CTG GAG ATG GCG
      GGT TGC GAC GGG CTC TAC GCG CAC GCG GCC GAC CTC TAC CGC

2026  GAC GCG ATG GAT ATG TTC TGC CAA GGG TTG GTT TGC GCA TTC ACA
      CTG CGC TAC CTA TAC AAG ACG CCC AAC GTT CAA ACG CGT AAG TGT

2071  GTT CTC CGC AAG AAT TGA TTG GCT CCA ATT CTT GGA GTG GTG AAT
      CAA GAG GCG TTC ACT AAC CGA GGT TAA GAA CCT CAC CAC TTA

2116  CCG AGG TGC CGC CGG CTT CCA TTC AGG TCG AGG TGG CCC
      GGC TCC ACG GCG GCC GAA AAG TCC AGC TCC ACC GGG

2161  GGC TCC ATG CAC GCA ACG CGG GGA GGC AGA CAA GGT ATA
      CCG AGG TAC GTG CGT GCC CCT CCG TCT GTT CCA TAT

2206  GGG CGG CGC TCC ATG CCA ACC CGT TCC ATG TCG CCG
      CCC GCC GCG GAT GTT AGG TAC ACG AGG TAC AGC GGC
```

FIG. 10H

```
2251  AGG CGG CAT AAA TCG CCG TGA CGA TCA GCG GTC CAG TGA TCG AAG
      TCC GCC GTA TTT AGC GGC ACT GCT AGT CGC CAG GTC ACT AGC TTC

2296  TTA GGC TGG TAA GAG CCG CGA GCG ATC CTT GAA GCT GTC CCT GAT
      AAT CCG ACC ATT CTC GGC GCT CGC TAG GAA CTT CGA CAG GGA CTA

2341  GGT CGT CAT CTA CCT GCC TGG ACA GCA TGG CCT GCA ACG CGG GCA
      CCA GCA GTA GAT GGA CGG ACC TGT CGT GGA CGT TGC GCC CGT

2386  TCC CGA TGC CGC CGG AAG CGA GAA TCA TAA TGG GGA AGG CCA
      AGG GCT ACG GCG GCC TTC GCT CTT AGT ATT ACC CCT TCC GGT

2431  TCC AGC CTC GCC GCG TCG CGA ACG CCA GCA CGT AGC CCA CGT CGT
      AGG TCG GAG CGG CGC AGC TGC GGT CGT GCA TCG AGC GGT CGC GCA
```

FIG. 10I

```
2476  CGG CCG CCA TGC CGG CGA TAA TGG CCT GCT TCT CGC CGA AAC GTT
      GCC GGC GGT ACG GCC GCT ATT ACC GGA AGA GCG GCT TTG CAA

2521  TGG CGG GAC CAG TGA CGA AGG CTT GAG CGA GGG CGT GCA AGA
      ACC GCC CTG GTC ACT GCT TCC GAA CTC CCC GCA CGT TCT

2566  TTC CGA ATA CCG CAA GCG ACA GGC CGA TCA TCG CGC TCC AGC
      AAG GCT TAT GGC GTT CGC TGT CCG AGT AGC GCG AGG TCG

2611  GAA AGC GGT CCT CGC CGA AAA TGA CCC AGA GCG CTG CCG CCT
      CTT TCG CCA GGA GCG GCT TTT ACT GGG TCT CGC GAC GGC GGA

2656  GTC CTA CGA GTT GCA TGA AGA CAG TCA TAA GTG CGG CGA
      CAG GAT GCT CAA CGT ACT TCT GTC ATT CAC GCC GCT

2701  CGA TAG TCA TGC CCC GCG CCC ACC AGG AGC TGA CTG GGT TGA
      GCT ATC AGT ACG GGG CGC TGG CCT TCG ACT GAC CCA ACT

2746  AGG CTC TCA AGG GCA TCG GTC GAC GCT CTC CCT TAT GCG ACT CCT
      TCC GAG AGT TCC CGT AGC CAG CTG CGA GAG ATA CGC TGA GGA
```

FIG. 10J

```
2791  GCA TTA GGA AGC AGC CCA GTA GGT TGA GGC CGT TGA GCA CCG
      CGT AAT CCT TCG TCG GGT CAT CCA ACT CCG GCA ACT CGT GGC

2836  CCG CCG CAA GGA ATG GTG CAT GCA AGG AGA TGG CGC CCA ACA GTC
      GGC GGC GTT CCT TAC CAC CGT TCC TCT ACC GCG GGT TGT CAG

2881  CCC CGG CCA CGG GGC CTG CCA TAC CCA CGC CGA AAC AAG CGC
      GGG GCC GGT GCC GAC GGT ATG GGT GCG GCT TTG TTC GCG

2926  TCA TGC CGA AGT GGC GAG CCC GAT CTT CCC CAT CGG TGA TGT
      AGT ACT CGG TCA CCC CTC GGG CTA GAA GGG GTA GCC ACT ACA

2971  CGG CGA TAT AGG CGC CAG CAC CTG TGG CGG TGA TGC
      GCC GCT ATA TCC GCG GTC GTG GAC ACC GCC ACT ACG

3016  CGG CCA CGA TGC GTC CGT AGA GGA TCC ACA CGG GTG TGG
      GCC GGT GCT ACG CAG TCT CCT AGG TGT CCT CAC ACC

3061  TCG CCA TGA TCG CGT AGT CGA TAG TGG CTC CAA GTA GCG AAG CGA
      AGC GGT ACT AGC GCA TCA GCT ATC ACC GAG GTT CAT CGC TTC GCT
```

FIG. 10K

```
3106  GCA GGA CTG GGC GGC CAA AGC CGT CGG ACA GTG CTC CGA GAA
      CGT CCT GAC CCG CCG GTT TCG GCC TGT CAC GAG GCT CTT

3151  CGG GTG CGC ATA GAA ATT GCA TCA ACG CAT ATA GCG CTA GCA
      GCC CAC GCG TAT CTT TAA CGT AGT TGC GTA TAT CGC GAT CGT

3196  CGC CAT AGT GAC TGG CGA TGC TGT CGG AAT GGA CGA TAT CCC GCA
      GCG GTA TCA CTG ACC GCT ACA GCC TTA CCT GCT ATA GGG CGT

3241  AGA GGC CCG GCA GTA CCG GCA TAA CCA AGC CTA TGC CTA CAG CAT
      TCT CCG GGC CGT CAT GGC CGT ATT GGT TCG GAT ACG GAT GTC GTA

3286  CCA GGG TGA CGG TGC CGA GGA TGA CGA CAT TGT TAG ATT
      GGT CCC ACT GCC ACG CCT ACT GCT CGC GTA ACA ATC TAA
```

FIG. 10L

```
3331 TCA TAC ACG GTG CCT GAC TGC GTT AGC AAT TTA ACT GTG ATA AAC
     AGT ATG TGC CAC GGA CTG ACG CAA TCG TTA AAT TGA CAC TAT TTG

3376 TAC CGC ATT AAA GCT TAT CGA TGA TAA GCT GTC AAA CAT GAG AAT
     ATG GCG TAA TTT CGA ATA GCT ACT ATT CGA CAG TTT GTA CTC TTA

3421 TAA
     ATT
```

Total number of bases is: 3423.
DNA sequence composition:  839 A;  915 C;  967 G;  702 T;

Sequence name: NIPS0060.

FIG. 10M

```
From: pmTNF MPH 3         9         15        21        27        33        39        45
              |         |         |         |         |         |         |         |
  1   AAT TCC GGG GAT CTC TCA CCT ACC AAA CAA TGC CCC CCT GCA AAA
      TTA AGG CCC CTA GAG AGT GGA TGG TTT GTT ACG GGG GGA CGT TTT 46   AAT AAA TTC ATA TAA AAA ACA AGA TAA CCA TAA CCA TCT GCG GTG ATA
      TTA TTT AAG TAT ATT TTT TGT TCT ATT GGT AGA CGC CAC TAT 91   AAT TAT CTC TGG CGG TGT TGA CAT AAA TAC CAC CGG TGA TAC
      TTA ATA GAG ACC GCC ACA ACT GTA ATG GTG ACC GCC ACT ATG 136   TGA GCA CAG CAG GAC GCA CTG ACC ATG AAG GTG ACG CTC
      ACT CGT GTC CTG CGT GAC TGG TAC TTC CAC TGC GAG 181   TTA AAA ATT AAG CCC TGA AGA AGG GCA GGG GTA CCA GGA GGT TTA
      AAT TTT TAA TTC GGG ACT TCT TCC CGT CCC CAT GGT CCT CCA AAT 226   AAT CAT GGT AAG ATC AAG TAG TCA AAA TTC GAG TGA CAA GCC TGT
      TTA GTA CCA TTC TAG ATC AGT TTT AAG CTC ACT GTT CGG ACA 271   AGC CCA CGT CGT AGC AAA CCA CCA AGT GGA CCT GCA GGG AAT TCA
      TCG GGT GCA GCA TCG TTT GGT TCA CCT GTC CCC TTA AGT 316   CCA TCA CCA TCA CCA CGT GGA TCC CGG GCC CGG CCA TGG CCG GAG
      GGT AGT GGT AGT GGT GCA CCT AGG GCC CGG GCC GGT ACC GGC CTC

FIG. 11B
```

```
361 GCC TCT AGA GTC GAC CGG CAT GCA AGC TTA AGT AAG TAA GCC GCC
    CGG AGA TCT CAG CTG GCC GTA CGT TCG AAT TCA TTC ATT CGG CGG

406 AGT TCC GCT GGC GGC ATT TTN ATT TTT GAT NTT NAA ACT GAC AAA
    TCA AGG CGA CCG CCG TAA AAN AAA AAA CTA NAA TTA CTG GAC AAA

451 TGG CGG ATG AGA GAA GAT TTT CAG CCT GAT TAA ATC AGA
    ACC GCC TAC TCT CTT AAA GTC GGA CTA ATT TAG TCT

496 ACG CAG AAG CGG TCT GAT AAA ACA GAA TTT ACA GAT CAG TAG
    TGC GTC TTC GCC AGA CTA TTT TGT CTT AAA CTA GTC ATC

541 CGC GGT GGT CCC ACC TGA CCC CAT GCC GAA CTC AGA GAA ACG
    GCG CCA CCA GGG TGG ACT GGG GTA CGG CTT GAG TCT TGC

586 CCG TAG CGC CGA TGG TAG TGT GGG GTC CCA TGC GAG AGT AGG
    GGC ATC GCG GCT ACC ATC ACA CCC CAG ACG CTC TCA TCC

631 GAA CTG CCA GGC ATC AAA TAA AAC GAA AGG CTC AGT CGA AAG ACT
    CTT GAC GGT CCG TAG TTT ATT TTG CTT TCC GAG TCA GCT TTC TGA

676 GGG CCT TTC GTT TCT GTT TGT CGG TGA ACG CTC TCC TGA
    CCC GGA AAG CAA AGA ACA AAC ACA GCC TGC GAG AGG ACT

721 GTA GGA CAA ATC CGC GAG CGG ATT TGA ACG TTG CGA AGC AAC
    CAT CCT GTT TAG GCG CTC GCC TAA ACT TGC AAC GCT TCG TTG
```

FIG. 11C

```
766  GGC CCG GAG GGT GGC GGG CAG GAC GCC CGG CAT AAA CTG CCA GGC
     CCG GGC CTC CCA CCG CCC GTC CTG CGG CCG GTA TTT GAC GGT CCG

811  ATC AAA TTA AGC AGA AGG CCA TCC TGA CGG ATG CCC TTT TTG CGT
     TAG TTT AAT TCG TCT TCC GGT AGG ACT GCC TAC GGG AAA AAC GCA

856  TTC TAC AAA CTC TTT TGT TTA CAA TAA CAT TCA AAT ATG
     AAG ATG GAG AAA ACA AAT GTT ATT TAT GTA AGT TTA TAC

901  TAT CCG CTC ATG AGA CAA TAA CCC TGA ATG CTT CAA TAA
     ATA GGC GAG TCT GTT ATT GGG ACT TAC GAA GTT ATT ATT

946  AAG GAT CTA GGT GAA GAT CCT TTT TGA TAA TCT CAT GAC CAA AAT
     TTC CTA GAT CCA CTT CTA GGA AAA ACT ATT AGA GTA CTG GTT TTA

991  CCC TTA ACG TGA GTT TTC GTT CCA CTG AGC GTC AGA CCC CGT AGA
     GGG AAT TGC ACT CAA AAG CAA GGT GAC TCG CAG TCT GGG GCA TCT

1036 AAA GAT CAA AGG ATC TTC TTG AGA TCC TTT TTT TCT GCG CGT AAT
     TTT CTA GTT TCC TAG AAG AAC TCT AGG AAA AAA AGA CGC GCA TTA
```

FIG. 11D

1081 CTG CTG CTT GCA AAC AAA ACC ACC GCT ACC AGC GGT GGT TTG
     GAC GAC GAA CGT TTG TTT TGG CGA TGG TCG CCA CCA AAC

1126 TTT GCC GGA TCA AGA GCT ACC AAC TCT TTT TCC GAA GGT AAC TGG
     AAA CGG CCT AGT TCT CGA TGG AGA AAA AGG CTT CCA TTG ACC

1171 CTT CAG CAG AGC GCA GAT ACC AAA TAC TGT CCT TCT AGT GTA GCC
     GAA GTC GTC TCG CGT CTA TGG TTT ATG ACA GGA AGA TCA CAT CGG

1216 GTA GTT AGG CCA CCA CTT CAA GAA CTC TGT AGC ACC GCC TAC ATA
     CAT CAA TCC GGT GTT GAA CTT GAG ACA TCG TGG CGG ATG TAT

1261 CCT CGC TCT GCT AAT CCT GTT ACC AGT GGC TGC TGC CAG TGG CGA
     GGA GCG AGA CGA TTA GGA CAA TGG TCA CCG ACG ACG GTC ACC GCT

1306 TAA GTC GTG TCT TAC CGG GTT GGA CTC AAG ACG ATA GTT ACC GGA
     ATT CAG CAC AGA ATG GCC CAA CCT GAG TTC TGC TAT CAA TGG CCT

1351 TAA GGC GCA GCG GTC GGG CTG AAC GGG GGG TTC GTG CAC ACA GCC
     ATT CCG CGT CGC CAG CCC GAC TTG CCC AAG CAC GTG TGT CGG

FIG. 11E

```
1396  CAG CTT GGA GCG AAC GAC CTA CAC CGA ACT GAG ATA CCT ACA GCG
      GTC GAA CCT CGC TTG CTG GAT GTG GCT TGA CTC TAT GGA TGT CGC

1441  TGA GCA TTG AGA AAG CGC CAC GCT TCC CGA AGG GAG AAA GGC GGA
      ACT CGT AAC TCT TTC GCG GTG CGA AGG GCT TCC CTC TTT CCG CCT

1486  CAG GTA TCC GGT AAG CGG CAG GGT CGG AAC AGG AGA GCG CAC GAG
      GTC CAT AGG CCA TTC GCC GTC CCA TTG TCC TCT CGC GTG CTC

1531  GGA GCT TCC AGG GGG AAA CGC CTG GTA TCT TTA TAG TCC TGT CGG
      CCT CGA AGG TCC CCC TTT GCG GAC CAT AGA AAT ATC AGG ACA GCC

1576  GTT TCG CCA CCT CTG ACT TGA GCG TCG ATT TTT GTG ATG CTC GTC
      CAA AGC GGT GGA GAC TGA ACT CGC AGC TAA AAA CAC TAC GAG CAG
```

FIG. 11F

```
1621  AGG GGG GCG GAG CCT ATG GAA AAA CGC CAG CAA CGC GGC CTT TTT
      TCC CCC CGC CTC GGA TAC CTT TTT GCG GTC GTT CCG GAA AAA

1666  ACG GTT CCT GGC CTT TTG CTG GCC TTT TGC TCA CAT GTT CAA TCC
      TGC CAA GGA CCG GAA AAC GAC CGG AAA ACG AGT GTA CAA AGG

1711  TGC GTT ATC CCC TGA TTC TGT GGA TAA CCG CAG TAT CGC CTT TGA
      ACG CAA TAG GGG ACT AAG ACA CCT ATT GGC ATA ATG GAA ACT

1756  GTG AGC TGA TAC CGC TCG CCG CAG CCG AAC GAC CGA GCG CAG CGA
      CAC TCG ACT ATG GCG AGC GGC GTC TTG CTG GCT CGC GTC GCT

1801  GTC AGT GAG CGA GGA AGC GGA AGA GCG CCT ACT TCC GCG TTT CCA
      CAG TCA CTC GCT CCT TCG CCT TCT CGC GGA TGA AGG CGC AAA GGT

1846  GAC TTT ACG AAA CAC GGA AAC CGA CCA TTC ATG TTG TTG CTC
      CTG AAA TGC TTT GTG CCT TTG GCT GGT AAG TAC AAC AAC GAG

1891  AGG TCG CAG ACG TTT TGC AGC AGC AGT CGC TTC ACG TTC GCT CGC
      TCC AGC GTC TGC AAA ACG TCG TCA GCG AAG TGC AAG CGA GCG
```

FIG. 11G

```
1936  GTA TCG GTG ATT CAT TCT GCT AAC CAG TAA GGC AAC CCC GCC AGC
      CAT AGC CAC TAA GTA AGA CGA TTG GTC ATT CCG GGG CGG TCG

1981  CTA GCC GGG TCC ACA GGA GCA CGA TCA TGC GCA CCC GTG
      GAT CGG CCC AGG TGT CCT CGT GCT AGT ACG CGT GGG CAC

2026  GCC AGG ACC CAA CGC TGC CCG AGA TGC GCC GGC TGC TGG
      CGG TCC TGG GTT GCG ACG GGC TCT ACG CGG CCG ACG ACC

2071  AGA TGG CGG ACG CGA TGG ATA TGT TCT GCC AAG GGT TGG TTT GCG
      TCT ACC GCC TGC GCT ACC TAT ACA AGA CGG TTC CCA ACC AAA CGC

2116  CAT TCA CAG TTC TCC GCA AGA ATT GAT TGG CTC TTC CAA TTC TTG GAG
      GTA AGT GTC AAG AGG CGT TCT TAA CTA ACC GAG GTT AAG AAC CTC

2161  TGG TGA ATC CGT TAG CGA GGT GCC GCC GGC TTC CAT TCA GGT CGA
      ACC ACT TAG GCA ATC GCT CCA CGG CCG AAG GTA AGT CCA GCT

2206  GGT GGC CCG GCT CCA TGC ACC GCG ACG CAA CGC GGG GAG GCA GAC
      CCA CCG GGC CGA GGT ACG TGG CGC TGC GTT GCG CCC CTC CGT CTG
```

FIG. 11H

```
2251 AAG GTA TAG GGC GCC TAC AAT CCA TGC CAA CCC GTT CCA TGT
     TTC CAT ATC CCG CGG ATG TTA GGT ACG GTT GGG CAA GGT ACA

2296 GCT CGC CGA GGC GGT ATA AAT CGC CGT GAC GAT CAG CGG TCC AGT
     CGA GCG GCT CCG CCA TAT TTA GCG GCA CTG CTA GTC GCC AGG TCA

2341 GAT CGA AGT TAG GCT GGT AAG AGC CGC GAG CGA TCC TTG AAG CTG
     CTA GCT TCA ATC CGA CCA TTC TCG GCG CTC AGG AAC TTC GAC

2386 TCC CTG ATG GTC ATC TAC CTG CCT GGA CAG CAT GGC CTG CAA
     AGG GAC TAC CAG TAG ATG GAC CCT GTC GTA CCG GAC GTT

2431 CGC GGG CAT CCC GAT GCC GCC GGA AGC GAG AAG AAT CAT AAT GGG
     GCG CCC GTA GGG CTA CGG CGG CCT TCG CTC TTC TTA GTA TTA CCC
```

FIG. 11I

```
2476  GAA GGC CAT CCA GCC TCG CGT CGC GAA CGC CAG CAA GAC GTA GCC
      CTT CCG GTA GGT CGG AGC GCA GCG CTT GCG GTC GTT CTG CAT CGG

2521  CAG CGC GTC GGC CGC CAT GCC CGC GAA GGC AAT GGC CTG CTT CTC GCC
      GTC GCG CAG CCG GCG GTA CGG GCG CTT CCG TTA CCG GAC GAA GAG CGG

2566  GAA ACG TTT GGT GGG CCC ACC AGT GAC GAA GGC TTG AGC GAG GGC
      CTT TGC AAA CCA CCG GGG TGG TCA CTG CTT AAC TCG CTC CCG

2611  GTG CAA GAT TCC GAA TAC CGC AAG CGA CAG GCC GAT CAT CGT CGC
      CAC GTT CTA AGG CTT ATG GCG TTC GCT GTC CTA GTA GCA GCG

2656  GCT CCA GCG AAA GCG CTC GCC GAA AAT GAC CCA GAG CGC TGC ACG
      CGA GGT CGC TTT CGC GAG CGG CTT TTA CTG GGT CTC GCG ACG

2701  CGG CAC CTG TCC TAC GAG TTG CAT AAA GAA GAC AGT CAT AAG
      GCC GTG GAC AGG ATG CTC AAC GTA TTT CTT GTG TCA GTA TTC

2746  TGC GGC GAT AGT CAT GCC CCG CGC CCA CCG GAA GGA GCT GAC
      ACG CCG CTA TCA GTA CGG GCG GGT GGC CTT CCT CGA CTG
```

FIG. 11J

```
2791 TGG GTT GAA GGC TCT CAA GGG CAT CGG TCG ACG CTC TCC CTT ATG
     ACC CAA CTT CCG AGA GTT CCC GTA GCC TGC GAG AGG GAA TAC

2836 CGA CTC CTG CAT TAG GAA CTT TAG GCA GCC CAG TAG GTT GAG GCC GTT
     GCT GAG GAC GTA ATC CTT ATC CGT CGG GTC CAA ATC CTC CGG CAA

2881 GAG CAC CGC CGC AAG GAA TGG TGC ATG CAA GGA GAT GGC GCC
     CTC GTG GCG GCG TTC CTT ACC TAC GTT CCT CTA CCG CGG

2926 CAA CAG TCC CCC GGC CGC CAC GCC TGC ACG CAC GCC GAA
     GTT GTC AGG GGG CCG GCG GTG ACG GTA CGT GCG CTT

2971 ACA AGC GCT CAT GAG CCC GAA GTG GCG AGC CCG ATC TTC CCC ATC
     TGT TCG CGA GTA CTC GGG CTT CAC CGC TCG GGC TAG AAG GGG TAG

3016 GGT GAT GTC GGC GAT ATA GGC GCC AGC AAC CGC ACC TGT GGC GCC
     CCA CTA CAG CCG CTA TAT CCG CGG TCG TTG GCG ACA CCG CGG

3061 GGT GAT GCC GGC CAC GAT GCG TCC GGC GTA GAG GAT CCA CAG GAC
     CCA CTA CGG CCG GTG CTA CGC AGG CCG CAT CTC CTA GGT GTC CTG
```

FIG. 11K

```
3106  GGG TGT GGT CGC CAT GAT CGC GTA GTC GAT AGT GGC TCC AAG TAG
      CCC ACA CCA GCG GTA CTA GCG CAT CAG CTA TCA CCG AGG TTC ATC

3151  CGA AGC GAG CAG GAC TGG GCG GCG GCC AAA GCG GTC GGA CAG TGC
      GCT TCG CTC GTC CTG ACC CGC CGC CGG TTT CGC CAG CCT GTC ACG

3196  TCC GAG AAC GGG TGC GCA TAG AAA TTG CAT CAA CGC ATA TAG CGC
      AGG CTC TTG CCC ACG CGT ATC TTT AAC GTA GTT GCG TAT ATC GCG

3241  TAG CAG CAC GCC ATA GTG ACT GGC GAT GCT GTC GGA ATG GAC GAT
      ATC GTC GTG CGG TAT CAC TGA CCG CTA CGA CAG CCT TAC CTG CTA

3286  ATC CCG CAA GAG GCC CGG TAC CGG CAT AAC CAA GCC TAT GCC
      TAG GGC GTT CTC CGG GCC ATG GTC GTA TTG GTT CGG ATA CGG
```

FIG. 11L

```
3331 TAC AGC ATC CAG GGT GAC GCC GAG GAT GAC GAT GAG CGC ATT
     ATG TCG TAG GTC CCA CTG CGG CTC CTA CTG CTA CTC GCG TAA

3376 GTT AGA TTT CAT ACA CGG TGC CTG ACT GCG TTA GCA ATT TAA CTG
     CAA TCT AAA GTA TGT GCC ACG GAC TGA CGC AAT CGT TAA ATT GAC

3421 TGA TAA ACT ACC GCA TTA AAG CTT ATC GAT GAT AAG CTG TCA AAC
     ACT ATT TGA TTC GAA TAG CTA TTC GAC AGT TTG

3466 ATG AGA ATT
     TAC TCT TAA
```

Total number of bases is: 3474.
DNA sequence composition:    845 A;    933 C;    978 G;    716 T;
2 OTHER;
Sequence name: NPMTNFMPH.

FIG. 11M

```
From: pIG2
            3         9        15        21        27        33        39        45
            -         -         -         -         -         -         -         -
  1   TTC CGG GGA TCT CTC ACC TAC CAA ACA ATG CCC CCC TGC AAA AAA
      AAG GCC CCT AGA GAG TGG ATG GTT TGT TAC GGG GGG ACG TTT TTT 46   TAA ATT CAT ATA AAA AAC ATA CAG ATA ACC ATC TGC GGT GAT AAA
      ATT TAA GTA TAT TTT TTG TAT GTC TAT TGG TAG ACG CCA CTA TTT 91   TTA TCT CTG GCG GTG TTG ACA TAA ATA CCA CTG GCG GTG ATA CTG
      AAT AGA GAC CGC CAC AAC TGT ATT TAT GGT GAC CGC CAC TAT GAC 136   AGC ACA TCA GCA GGA CGC ACT GAC CAC CAT GAA GGT GAC CTG CTT
      TCG TGT AGT CGT CCT GCG TGA CTG GTG GTA CTT CCA CTG CGA GAA 181   AAA AAT TAA GCC CTG AAG GGC AGG GGT ACC AGG TTT AAA
      TTT TTA ATT CGG GAC TTC CCG TCC CCA TGG TCC AAA TTT 226   TAT TCC ATG GGG ATC CTC TAG AGT CGA CCT GCA CAA GCT
      ATA AGG TAC CCC TAG GAG ATC TCA GCT GGA CGT GTT CGA 271   TGG CTG TTT TGG CGG ATG CGG AGA GAT TTT CAG CCT GAT ACA GAT
      ACC GAC AAA ACC GCC TAC GCC TCT CTA AAA GTC GGA CTA TGT CTA 316   TAA ATC AGA ACG CAG AAG CGG TCT GAT AAA ACA GAA TTT GCC TGG
      ATT TAG TCT TGC GTC TTC GCC AGA CTA TTT TGT CTT AAA CGG ACC
```

FIG. 12B

```
361  CGG CAG TAG CGC GGT GGT CCC ACC TGA CCC CAT GCC GAA CTC AGA
     GCC GTC ATC GCG CCA CCA GGG TGG ACT GGG GTA CGG CTT GAG TCT
406  AGT GAA ACG CCG TAG CGC TGG CGA TGG TAG TGT GGG GTC TCC CCA TGC
     TCA CTT TGC GGC ATC GCG ACC GCT ACC ATC ACA CCC CAG AGG GGT ACG
451  GAG AGT AGG GAA CTG CCA GGC ATC AAA TAA AAC GAA AGG CTC AGT
     CTC TCA TCC CTT GAC GGT CCG TAG TTT ATT TTG CTT GAG TCA
496  CGA AAG ACT GGG CCT TTC GTT GTT TGT CGG TGA ACG
     GCT TTC TGA CCC GGA AAG CAA CAA ACA GCC ACT TGC
541  CTC TCC TGA GTA GGA CAA ATC CGC CGG GAG ATT TGA ACG TTG
     GAG AGG ACT CAT CCT GTT TAG GCG GCC CTC TAA ACT TGC AAC
586  CGA AGC AAC GGC CCG GGT GGG CAG GAC GCC CAT AAA
     GCT TCG TTG CCG GGC CCA CCC GTC CTG CGG GTA TTT
631  CTG CCA GGC ATC AAA AGC AGA AGG CCA TCC TGA CGG ATG GCC
     GAC GGT CCG TAG TTT TCG TCT TCC AGG ACT GCC TAC CGG
676  TTT TTG CGT TTC TAC AAA CTC TTT TGT TTA TTC TAA ATA CAT
     AAA AAC GCA AAG ATG TTT GAG AAA ACA AAT AAG ATT TAT GTA
721  TCA AAT ATG TAT CCG CTC ATG AGA CAA TAA CCC TGA TAA ATG CTT
     AGT TTA TAC ATA GGC GAG TAC TCT GTT ATT GGG ACT ATT TAC GAA
```

FIG. 12C

```
766   CAA TAA AAG GAT CTA GGT GAA GAT CCT TTT TGA TAA TCT CAT
      GTT ATT TTC CTA GAT CCA CTT CTA GGA AAA ACT ATT AGA GTA

811   GAC CAA AAT CCC TTA ACG TGA GTT TTC GTT CCA CTG AGC GTC AGA
      CTG GTT TTA GGG AAT TGC ACT CAA AAG GGT GAC TCG CAG TCT

856   CCC CGT AGA AAA GAT CAA AGG ATC TTC TTG AGA TCC TTT TTT TCT
      GGG GCA TCT TTT CTA GTT TCC TAG AAG AAC TCT AGG AAA AAA AGA

901   GCG CGT AAT CTG CTG CTT GCA AAC AAA AAA TTT ACC ACC GCT ACC AGC
      CGC GCA TTA GAC GAC GAA CGT TTG TTT AAA TGG CGA TGG TCG

946   GGT GGT TTG TTT GCC GGA TCA AGA GCT ACC AAC TCT TTT TCC GAA
      CCA CCA AAC AAA CGG CCT AGT TCT CGA TGG TTG AGA AAA AGG CTT

991   GGT AAC TGG CTT CAG AGC GCA GAT ACC AAA TAC TGT CCT TCT
      CCA TTG ACC GAA GTC CGT TCG CTA TGG TTT ATG ACA GGA AGA

1036  AGT GTA GCC GTA GTT AGG CCA CCA CTT CAA GAA CTC TGT AGC ACC
      TCA CAT CGG CAT CAA TCC GGT GGT GAA GTT CTT GAG ACA TCG TGG
```

FIG. 12D

```
1081  GCC TAC ATA CCT CGC TCT GCT AAT CCT GTT ACC AGT GGC TGC TGC
      CGG ATG TAT GGA GCG AGA CGA TTA GGA CAA TGG TCA CCG ACG ACG

1126  CAG TGG CGA TAA GTC GTG TCT TAC CGG GTT CAA GGA CTC AAG TTC GTG
      GTC ACC GCT ATT CAG CAC AGA ATG GCC CAA CCT GAG TTC TGC TAT

1171  GTT ACC GGA TAA GGC GCA GCG GTC GGG CTG GGG GGG TTC GTG
      CAA TGG CCT ATT CCG CGT CGC CAG CCC GAC CCC CCC AAG CAC

1216  CAC ACA GCC CAG CTT GGA GCC AAC GAC CTA CAC ACT GAG ATA
      GTG TGT CGG GTC GAA CCT CGG CGC TTG CTG GAT GTG TGA CTC TAT

1261  CCT ACA GCG TGA GCA TTG AGA AAG CGC CAC GCT TCC CGA AGG GAG
      GGA TGT CGC ACT CGT AAC TCT TTC GCG GTG CGA AGG GCT TCC CTC

1306  AAA GGC GGA CAG GTA TCC GGT AAG CGG CAG GGT CGG AAC AGG AGA
      TTT CCG CCT GTC CAT AGG CCA TTC GCC GTC CCA GCC TTG TCC TCT

1351  GCG CAC GAG GCT TCC AGG GGG AAA CGC CTG GTA TCT TTA TAG
      CGC GTG CTC CGA AGG TCC CCC TTT GCG GAC CAT AGA AAT ATC
```

FIG. 12E

```
1396  TCC TGT CGG GTT TCG CCA CCT CTG ACT TGA GCG TCG ATT TTT GTG
      AGG ACA GCC CAA AGC GGT GGA GAC TGA ACT CGC AGC TAA AAA CAC

1441  ATG CTC GTC AGG GGG GCG GAG CCT ATG GAA AAA CGC CAG CAA CGC
      TAC GAG CAG TCC CCC CGC CTC GGA TAC CTT TTT GCG GTC GTT GCG

1486  GGC CTT TTT ACG GTT CCT GGC CTT TTG CTG GCC TTT TGC TCA CAT
      CCG GAA AAA TGC CAA GGA CCG GAA AAC GAC CGG AAA ACG AGT GTA

1531  GTT CTT TCC TGC GTT ATC CCC TGA TTC TGT GGA TAA CCG TAT TAC
      CAA GAA AGG ACG CAA TAG GGG ACT AAG ACA CCT ATT GGC ATA ATG

1576  CGC CTT TGA GTG AGC TGA TAC CGC TCG CCG CCG CAG CCG AAC GAC CGA
      GCG GAA ACT CAC TCG ACT ATG GCG AGC GGC GGC GTC GGC TTG CTG GCT
```

FIG. 12F

```
1621 GCG CAG CGA GTC AGT GAG CGA GGA AGC GGA AGA GCG CTG ACT TCC
     CGC GTC GCT CAG TCA CTC GCT CCT TCG CCT TCT CGC GAC TGA AGG

1666 GCG TTT CCA GAC TTT ACG AAA CAC GGA AAC CGA AGA CCA TTC ATG
     CGC AAA GGT CTG AAA TGC TTT GTG CCT TTG GCT TCT GGT AAG TAC

1711 TTG TTG CTC AGG TCG CAG ACG TTT TGC AGC AGT CGC TTC ACG
     AAC AAC GAG TCC AGC GTC TGC AAA ACG TCG TCA GCG AAG TGC

1756 TTC GCT CGC GTA TCG ATT CAT TCT GCT AAC CAG TAA GGC AAC
     AAG CGA GCG CAT AGC GTA AGA GTA AGA CGA TTG GTC ATT CCG TTG

1801 CCC GCC AGC CTA GCC TCC TCA ACG ACA GGA GCA CGA TCA TGC
     GGG CGG TCG GAT CGG AGG AGT TGC TGT CCT CGT AGT ACG

1846 GCA CCC GTG GCC AGG ACC CAA CGC TGC CCG AGA TGC GCC GCG TGC
     CGT GGG CAC CGG TCC TGG GTT GCG ACG GGC TCT ACG CGG CGC ACG

1891 GGC TGC TGG AGA TGG CGG ACG CGA TGG ATA TGT TCT GCC AAG GGT
     CCG ACG ACC TCT ACC GCC TGC GCT ACC TAT ACA AGA CGG TTC CCA
```

FIG. 12G

```
1936  TGG TTT GCG CAT TCA CAG TTC TCC GCA AGA ATT GAT TGG CTC CAA
      ACC AAA CGC GTA AGT GTC AAG AGG CGT TAA CTA ACC GAG GTT

1981  TTC TTG GAG TGG TGA ATC CGT TAG CGA GGT GCC GCC GGC TTC CAT
      AAG AAC CTC ACC ACT TAG GCA ATC GCT CCA CGG CCG AAG GTA

2026  TCA GGT CGA GGT GGC CCG GCT CCA TGC ACC GCG CAA CGC GGG
      AGT CCA GCT CCA CCG GGC CGA GGT ACG TGC GTT GCG CCC

2071  GAG GCA GAC AAG GTA TAG GGC GCC CGG TAC AAT CCA TGC CAA CCC
      CTC CGT CTG TTC CAT ATC CCG CGG GCC ATG TTA GGT ACG GTT GGG

2116  GTT CCA TGT GCT CGC CGA GGC CCG GGC ATA AAT CGC CGT GAC GAT CAG
      CAA GGT ACA CGA GCG GCT CCG GGC TAT TTA GCG GCA CTG CTA GTC

2161  CGG TCC AGT GAT CGA AGT TAG GCT AAG AGC CGC GAG CGA TCC
      GCC AGG TCA GCT TCA ATC CGA CCA TTC TCG GCG CTC GCT AGG

2206  TTG AAG CTG TCC CTG ATG GTC ATC TAC CTG CCT GGA CAG CAT
      AAC TTC GAC AGG GAC TAC CAG TAG ATG GAC GGA CCT GTC GTA
```

FIG. 12H

```
2251  GGC CTG CAA CGC GGG CAT CCC GAT GCC GGA AGC GAG AAG AAT
      CCG GAC GTT GCG CCC GTA GGG CTA CGG CCT TCG CTC TTC TTA

2296  CAT AAT GGG GAA CAT CCA GCC TCG CGT CGC GAA CGC CAG CAA
      GTA TTA CCC CTT GTA GGT CGG AGC GCA GCG CTT GCG GTC GTT

2341  GAC GTA GCC CAG CGC GTC GGC CGC CAT GCC GGC GAT AAT GGC CTG
      CTG CAT CGG GTC CAG CCG GCG GTA CGG CCG CCA TTA CCG GAC

2386  CTT CTC GCC GAA ACG TTT GGT GGC GGG ACC AGT GAC GAA GGC TTG
      GAA GAG CGG CTT TGC AAA CCA CCG CCC TGG TCA CTG CTT CCG AAC

2431  AGC GAG GGC GTG CAA GAT TCC GAA TAC CGC AAG CGA CAG GCC GAT
      TCG CTC CCG CAC GTT CTA AGG CTT ATG GCG TTC GCT GTC CGG CTA
```

FIG. 12I

```
2476 CAT CGT CGC GCT CCA GCG GTC CTC GCC GAA AAT GAC CCA
     GTA GCA GCG CGA GGT CGC CAG GAG CGG CTT TTA CTG GGT

2521 GAG CGC TGC CGG CAC CTG TCC TAC GAG TTG CAT GAT AAA GAA GAC
     CTC GCG ACG GCC GTG GAC AGG ATG CTC AAC GTA CTA TTT CTT CTG

2566 AGT CAT AAG TGC GGC GAC GAT AGT CAT GCC CCG CGC CCA CCG GAA
     TCA GTA TTC ACG CCG CTG CTA TCA GTA CGG GGC GCG GGT GGC CTT

2611 GGA GCT GAC TGG GTT GAA TCT CAA GGC CAT CGG CAT CGG TCG ACG CTC
     CCT CGA CTG ACC CAA CTT AGA CCG GTA GCC TGC GAG

2611 GGA GCT GAC TGG GTT GAA TCT CAA GGC CAT CGG TCG ACG CTC
     CCT CGA CTG ACC CAA CTT AGA CCG GTA GCC AGC TGC GAG

2656 TCC CTT ATG CGA CTC CTG GAA GCA GCC CAG TAG TAG GTT
     AGG GAA TAC GCT GAG GAC CTT CGT CGG GTC ATC ATC CAA

2701 GAG GCT GTT GAG CAC CGC CGC AAG GAA TGG TGC ATG CAA GGA
     CTC CGA CAA CTC GTG GCG GCG TTC CTT ACC ACG TAC GTT CCT

2746 GAT GGC GCC CAA CAG TCC CCC GGC CAC GGG GCC TGC CAT ACC
     CTA CCG CGG GTT GTC AGG GGG CCG GTG CCC CGG ACG GTA TGG
```

FIG. 12J

| | | | | | | | | | | | | | | |
|---|---|---|---|---|---|---|---|---|---|---|---|---|---|---|
| 2791 | CAC | GCC | GAA | ACA | AGC | GCT | CAT | GAG | CCC | GAA | GTG | GCG | AGC | CCG | ATC |
| | GTG | CGG | CTT | TGT | TCG | CGA | GTA | CTC | GGG | CTT | CAC | CGC | TCG | GGC | TAG |
| 2836 | TTC | CCC | ATC | GGT | GAT | GTC | GGC | GAT | ATA | GGC | GCC | AAC | CGC | AGC | ACC |
| | AAG | GGG | TAG | CCA | CTA | CAG | CCG | CTA | TAT | CCG | CGG | TTG | GCG | TCG | TGG |
| 2881 | TGT | GGC | GCC | GGT | GAT | GCC | GGC | CAC | GAT | GCG | TCC | GGC | GTA | GAG | GAT |
| | ACA | CCG | CGG | CCA | CTA | CGG | CCG | GTG | CTA | CGC | AGG | CCG | CAT | CTC | CTA |
| 2926 | CCA | CAG | GAC | GGG | TGT | CGC | CAT | GAT | CGC | GTA | GTC | GAT | CGT | AGT | GGC |
| | GGT | GTC | CTG | CCC | ACA | GCG | GTA | CTA | GCG | CAT | CAG | CTA | GCA | TCA | CCG |
| 2971 | TCC | AAG | TAG | CGA | AGC | GAG | CAG | GAC | TGG | GCG | GCG | AAA | GCC | GTC | CAG |
| | AGG | TTC | ATC | GCT | TCG | CTC | GTC | CTG | ACC | CGC | CGC | TTT | CGG | CAG | GTC |
| 3016 | GGA | CAG | TGC | TCC | GAG | AAC | GGG | TGC | GCA | TAG | AAA | TTG | CAT | CAA | CGC |
| | CCT | GTC | ACG | AGG | CTC | TTG | CCC | ACG | CGT | ATC | TTT | AAC | GTA | GTT | GCG |
| 3061 | ATA | TAG | CGC | TAG | CAG | CAC | GCC | ATA | GTG | ACT | GGC | GAT | GCT | GTC | GGA |
| | TAT | ATC | GCG | ATC | GTC | GTG | CGG | TAT | CAC | TGA | CCG | CTA | CGA | CAG | CCT |

FIG. 12K

```
3106 ATG GAC GAT ATC CCG CAA GAG GCC CGG CAG TAC CGG CAT AAC CAA
     TAC CTG CTA TAG GGC GTT CTC CGG GCC GTC ATG GCC GTA TTG GTT

3151 GCC TAT GCC TAC AGC ATC CAG GGT GAC GGT GCC GAG GAT GAC GAT
     CGG ATA CGG ATG TCG TAG GTC CCA CTG CGG CTC CTA CTG CTA

3196 GAG CGC ATT GTT AGA TTT CAT ACA CGG TGC CTG ACT GCG TTA GCA
     CTC GCG TAA CAA TCT AAA GTA TGT GCC ACG GAC TGA CGC AAT CGT

3241 ATT TAA CTG TGA TAA ACT ACC GCA TTA AAG CTT ATC GAT GAT AAG
     TAA ATT GAC ACT ATT TGA TGG CGT AAT TTC GAA TAG CTA CTA TTC

3286 CTG TCA AAC ATG AGA A
     GAC AGT TTG TAC TCT T

Total number of bases is: 3301.
DNA sequence composition:     797 A;     887 C;     936 G;     681 T;

Sequence name: NIPS0039.
```

FIG. 12L

Amino acid sequence of the fusion protein mTNF His6 P32

338 AA

```
1   Met Val Arg Ser Ser Ser Gln Asn Ser Ser
11  Asp Lys Pro Val Ala His Val Val Ala Asn
21  His Gln Val Glu Glu Gln Gly Ile His His
31  His His His His Val Asp Pro Gly Pro Met
41  Ala Phe Arg Arg His Gly Pro Gly ... ...
.
.
.
.
.
.
.
331 Thr Gly Pro Ala Pro Glu Gly Ala
```

ANTI-TNF    ANTI-32 kDa

US 7,083,797 B2

32-KDA PROTEIN DERIVED FROM *MYCOBACTERIUM TUBERCULOSIS* AND RELATED PEPTIDES

CROSS-REFERENCE TO RELATED APPLICATIONS

This application is a divisional application of and claims priority to U.S. application Ser. No. 09/342,673, filed Jun. 29, 1999 now U.S. Pat. No. 6,531,138, which is a continuation application of U.S. application Ser. No. 08/447,430, filed May 22, 1995 now U.S. Pat. No. 5,916,558, which is a file-wrapper-continuation of U.S. application Ser. No. 07/690,949, filed Jul. 8, 1991 now abandoned, based on PCT/EP90/01593, filed Sep. 19, 1990, and British application No. 89402571.7, filed Sep. 19, 1989. The disclosure of the prior application is considered part of (and is incorporated by reference in) the disclosure of this application.

BACKGROUND OF THE INVENTION

1. Field of the Invention

The invention relates to recombinant polypeptides and peptides, which can be used for the diagnosis of tuberculosis. The invention also relates to a process for preparing the above-said polypeptides and peptides, which are in a state of biological purity such that they can be used as part of the active principle in the preparation of vaccines against tuberculosis.

It also relates to nucleic acids coding for said polypeptides and peptides.

Furthermore, the invention relates to the in vitro diagnostic methods and kits using the above-said polypeptides and peptides and to the vaccines containing the above-said polypeptides and peptides as active principle against tuberculosis.

By "recombinant polypeptides or peptides" it is to be understood that it relates to any molecule having a polypeptidic chain liable to be produced by genetic engineering, through transcription and translation, of a corresponding DNA sequence under the control of appropriate regulation elements within an efficient cellular host. Consequently, the expression "recombinant polypeptides" such as is used herein does not exclude the possibility for the polypeptides to comprise other groups, such as glycosylated groups.

The term "recombinant" indeed involves the fact that the polypeptide has been produced by genetic engineering, particularly because it results from the expression in a cellular host of the corresponding nucleic acid sequences which have previously been introduced into the expression vector used in said host.

Nevertheless, it must be understood that this expression does not exclude the possibility for the polypeptide to be produced by a different process, for instance by classical chemical synthesis according to methods used in the protein synthesis or by proteolytic cleavage of larger molecules.

The expression "biologically pure" or "biological purity" means on the one hand a grade of purity such that the recombinant polypeptide can be used for the production of vaccinating compositions and on the other hand the absence of contaminants, more particularly of natural contaminants.

2. Description of the Prior Art

Tuberculosis remains a major disease in developing countries. The situation is dramatic in some countries, particularly where high incidence of tuberculosis among AIDS patients represents a new source of dissemination of the disease.

Tuberculosis is a chronic infectious disease in which cell-mediated immune mechanisms play an essential role both for protection against and control of the disease.

Despite BCG vaccination, and some effective drugs, tuberculosis remains a major global problem. Skin testing with tuberculin PPD (protein-purified derivative) largely used for screening of the disease is poorly specific, due to cross reactivity with other pathogenic or environmental saprophytic mycobacteria.

Moreover, tuberculin PPD when used in serological tests (ELISA) does not allow to discriminate between patients who have been vaccinated by BCG, or those who have been primo-infected, from those who are developing evolutive tuberculosis and for whom an early and rapid diagnosis would be necessary.

A protein with a molecular weight of 32-kDa has been purified (9) from zinc deficient *Mycobacterium bovis* BCG culture filtrate (8). This 32-kDa protein of *M. bovis* BCG has been purified from Sauton zinc deficient culture filtrate of *M. bovis* BCG using successively hydrophobic chromatography on Phenyl-Sepharose, ion exchange on DEAE-Sephacel and molecular sieving on Sephadex G-100. The final preparation has been found to be homogeneous as based on several analyses. This $P_{32}$ protein is a constituent of BCG cells grown in normal conditions. It represents about 3% of the soluble fraction of a cellular extract, and appears as the major protein released in normal Sauton culture filtrate. This protein has been found to have a molecular weight of 32 000 by SDS-polyacrylamide gel electrophoresis and by molecular sieving.

The NH$_2$-terminal amino acid sequence of the 32-kDa protein of *M. bovis* BCG (Phe-Ser-Arg-Pro-Gly-Leu (SEQ ID NO:49)) is identical to that reported for the MPB 59 protein purified from *M. bovis* BCG substrain Tokyo (34).

Purified $P_{32}$ of *M. bovis* BCG has been tested by various cross immunoelectrophoresis techniques, and has been shown to belong to the antigen 85 complex in the reference system for BCG antigens. It has been more precisely identified as antigen 85A in the Closs reference system for BCG antigens (7).

Increased levels of immunoglobulin G antibodies towards the 32-kDa protein of *M. bovis* BCG could be detected in 70% of tuberculous patients (30).

Furthermore, the 32-kDa protein of *M. bovis* BCG induces specific lymphoproliferation and interferon-(IFN-γ) production in peripheral blood leucocytes from patients with active tuberculosis (12) and PPD-positive healthy subjects. Recent findings indicate that the amount of 32-kDa protein of *M. bovis* BCG-induced IFN-γ in BCG-sensitized mouse spleen cells is under probable H-2 control (13). Finally, the high affinity of mycobacteria for fibronectin is related to proteins of the BCG 85 antigen complex (1).

Matsuo et al. (17) recently cloned the gene encoding the antigen α, a major protein secreted by BCG (substrain Tokyo) and highly homologous to MPB 59 antigen in its NH$_2$-terminal amino acid sequence, and even identical for its first 6 amino acids: Phe-Ser-Arg-Pro-Gly-Leu (SEQ ID NO:49).

This gene was cloned by using a nucleotide probe homologous to the N-terminal amino acid sequence of antigen α, purified from *M. tuberculosis* as described in Tasaka, H. et al., 1983. "Purification and antigenic specificity of alpha protein (Yoneda and Fukui) from *Mycobacterium tuberculosis* and *Mycobacterium intracellulare*. Hiroshima J. Med. Sci. 32, 1–8.

The presence of antigens of around 30–32-kDa, named antigen 85 complex, has been revealed from electrophoretic patterns of proteins originating from culture media of mycobacteria, such as *Mycobacterium tuberculosis*. By immunoblotting techniques, it has been shown that these antigens cross-react with rabbit sera raised against the 32-kDa protein of BCG (8).

A recent study reported on the preferential humoral response to a 30-kDa and 31-kDa antigen in lepromatous leprosy patients, and to a 32-kDa antigen in tuberculoid leprosy patients (24).

It has also been found that fibronectin (FN)-binding antigens are prominent components of short-term culture supernatants of *Mycobacterium tuberculosis*. In 3-day-old supernatants, a 30-kilodalton (kDa) protein was identified as the major (FN)-binding molecule. In 21-day-old supernatants, FN was bound to a double protein band of around 30 to 32-kDa, as well as to a group of antigens of larger molecular mass (57 to 60 kDa) (1).

In other experiments, recombinant plasmids containing DNA from *Mycobacterium tuberculosis* were transformed into *Escherichia coli*, and three colonies were selected by their reactivity with polyclonal antisera to *M. tuberculosis*. Each recombinant produced 35- and 53-kilodalton proteins (35K and 53K proteins, respectively) ("Expression of Proteins of *Mycobacterium tuberculosis* in *Escherichia coli* and Potential of Recombinant Genes and Proteins for Development of Diagnostic Reagents", Mitchell L Cohen et al., Journal of Clinical Microbiology, July 1987, p. 1176–1180).

Concerning the various results known to date, the physico-chemical characteristics of the antigen $P_{32}$ of *Mycobacterium tuberculosis* are not precise and, furthermore, insufficient to enable its unambiguous identifiability, as well as the characterization of its structural and functional elements.

Moreover, the pathogenicity and the potentially infectious property of *M. tuberculosis* has hampered research enabling to identify, purify and characterize the constituents as well as the secretion products of this bacteria.

SUMMARY OF THE INVENTION

An aspect of the invention is to provide recombinant polypeptides which can be used as purified antigens for the detection and control of tuberculosis.

Another aspect of the invention is to provide nucleic acids coding for the peptidic chains of biologically pure recombinant polypeptides which enable their preparation on a large scale.

Another aspect of the invention is to provide antigens which can be used in serological tests as an in vitro rapid diagnostic of tuberculosis.

Another aspect of the invention is to provide a rapid in vitro diagnostic means for tuberculosis, enabling it to discriminate between patients suffering from an evolutive tuberculosis from those who have been vaccinated against BCG or who have been primo-infected.

Another aspect of the invention is to provide nucleic probes which can be used as in vitro diagnostic reagent for tuberculosis, as well as in vitro diagnostic reagent for identifying *M. tuberculosis* from other strains of mycobacteria.

The recombinant polypeptides of the invention contain in their polypeptidic chain one at least of the following amino acid sequences:

the one extending from the extremity constituted by amino acid at position (−29) to the extremity constituted by amino acid at position (−1) represented on FIG. 3*a* and FIG. 3*b*, or the one extending from the extremity constituted by amino acid at position (12) to the extremity constituted by amino acid at position (31) represented on FIG. 3*a* and FIG. 3*b*, or the one extending from the extremity constituted by amino acid at position (36) to the extremity constituted by amino acid at position (55) represented on FIG. 3*a* and FIG. 3*b*, or the one extending from the extremity constituted by amino acid at position (77) to the extremity constituted by amino acid at position (96) represented on FIG. 3*a* and FIG. 3*b*, or the one extending from the extremity constituted by amino acid at position (101) to the extremity constituted by amino acid at position (120) represented on FIG. 3*a* and FIG. 3*b*, or the one extending from the extremity constituted by amino acid at position (175) to the extremity constituted by amino acid at position (194) represented on FIG. 3*a* and FIG. 3*b*, or the one extending from the extremity constituted by amino acid at position (211) to the extremity constituted by amino acid at position (230) represented on FIG. 3*a* and FIG. 3*b*, or the one extending from the extremity constituted by amino acid at position (275) to the extremity constituted by amino acid at position (294) represented on FIG. 3*a* and FIG. 3*b*, and the peptidic sequences resulting from the modification by substitution and/or by addition and/or by deletion of one or several amino acids in so far as this modification does not alter the following properties:

the polypeptides react with rabbit polyclonal antiserum raised against the protein of 32-kDa of *M. bovis* BCG culture filtrate, and/or react selectively with human sera from tuberculosis patients and particularly patients developing an evolutive tuberculosis at an early stage, and/or react with the amino acid sequence extending from the extremity constituted by amino acid at position (1), to the extremity constituted by amino acid at position (294) represented on FIG. 3*a* and FIG. 3*b*.

On FIGS. 3*a* and 3*b*:

X represents G or GG,

Y represents C or CC,

Z represents C or G,

W represents C or G and is different from Z,

K represents C or CG,

L represents G or CC, $a_1$-$b_1$ represents ALA-ARG or GLY-ALA-ALA, $a_2$ represents arg or gly, $a_3$-$b_3$-$c_3$-$d_3$-$e_3$-$f_3$- represents his-trp-val-pro-arg-pro or ala-leu-gly-ala, $a_4$ represents pro or pro-asn-thr, $a_5$ represents pro or ala-pro.

The recombinant polypeptides of the invention contain in their polypeptidic chain one at least of the following amino acid sequences:

the one extending from the extremity constituted by amino acid at position (−29) to the extremity constituted by amino acid at position (−1) represented on FIG. 4*a* and FIG. 4*b*, or the one extending from the extremity constituted by amino acid at position (12) to the extremity constituted by amino acid at position (31) represented on FIG. 4*a* and FIG. 4*b*, or the one extending from the extremity constituted by amino acid at position (36) to the extremity constituted by amino acid at position (55) represented on FIG. 4a and FIG. 4b, or the one extending from the extremity constituted by amino acid at position (77) to the extremity constituted by amino acid at position (96) represented on FIG. 4a and FIG. 4b, or the one extending from the extremity constituted by amino acid at position (101) to the extremity constituted by amino acid at position (120) represented on FIG. 4a and FIG. 4b, or the one extending from the extremity constituted by amino acid at position (175) to the extremity constituted by amino acid at position (194) represented on FIG. 4a and FIG. 4b, or the one extending from the extremity constituted by amino acid at position (211) to the extremity constituted by amino acid at position (230) represented on FIG. 4a and FIG. 4b, or the one extending from the extremity constituted by amino acid at position (275) to the extremity constituted by amino acid at position (294) represented on FIG. 4a and FIG. 4b, and the peptidic sequences resulting from the modification by substitution and/or by addition and/or by deletion of one or several amino acids in so far as this modification does not alter the following properties:

the polypeptides react with rabbit polyclonal antiserum raised against the protein of 32-kDa of *M. bovis* BCG culture filtrate, and/or react selectively with human sera from tuberculosis patients and particularly pat man spectrophotometer. For control of purity the gel is revealed with silver stain (Biorad Laboratories, Richmond, Calif.).

The purification step of $P_{32}$ is carried out as follows:

Except for hydrophobic chromatography on Phenyl-Sepharose, all buffers contain Tween 80 (0.005% final concentration). The pH is adjusted to 7.3 before sterilization. All purification steps are carried out at +4° C. Elutions are followed by recording the absorbance at 280 nm. The fractions containing proteins are analysed by SDS-PAGE.

(i) The treated filtrate from a 4 liters zinc-deficient culture, usually containing 125 to 150 mg protein per liter, is applied to a column (5.0 by 5.0 cm) of Phenyl-Sepharose CL-4B (Pharmacia Fine Chemicals, Uppsala, Sweden), which is previously equilibrated with 20 mM phosphate buffer (PB) containing 0.45 M NaCl and 1 mM EDTA, at a flow rate of 800 ml per hour. The gel is then washed with one column volume of the same buffer to remove unfixed material and successively with 300 ml of 20 mM and 4 mM PB and 10% ethanol (v/v). The $P_{32}$ appears in the fraction eluted with 10% ethanol.

(ii) After the phosphate concentration of this fraction has been brought to 4 mM, it is applied to a column (2.6 by 10 cm) of DEAE-Sephacel (Pharmacia Fine Chemicals), which is equilibrated with 4 mM PB. After washing with the equilibrating buffer the sample is eluted with 25 mM phosphate at a flow rate of 50 ml per hour. The eluate is concentrated in a 202 Amicon stirred cell equipped with a PM 10 membrane (Amicon Corp., Lexington, Mass.).

(iii) The concentrated material is submitted to molecular sieving on a Sephadex G-100 (Pharmacia) column (2.6 by 45 cm) equilibrated with 50 mM PB, at a flow rate of 12 ml per hour. The fractions of the peak giving one band in SDS-PAGE are pooled. The purity of the final preparation obtained is controlled by SDS-PAGE followed by silver-staining and by molecular sieving on a Superose 12 (Pharmacia) column (12.0 by 30 cm) equilibrated with 50 mM PB containing 0.005% Tween 80 at a flow rate of 0.2 ml/min. in the Fast Protein Liquid Chromatography system (Pharmacia). Elution is followed by recording the absorbance at 280 nm and 214 nm.

b) Preparation of rabbit polyclonal antiserum raised against the $P_{32}$ protein of BCG:

400 µg of purified $P_{32}$ protein of BCG per ml physiological saline are mixed with one volume of incomplete Freund's adjuvant. The material is homogenized and injected intradermally in 50 µl doses delivered at 10 sites in the back of the rabbits, at 0, 4, 7 and 8 weeks (adjuvant is replaced by the diluent for the last injection). One week later, the rabbits are bled and the sera tested for antibody level before being distributed in aliquots and stored at −80° C.;

2) test for giving evidence of the reaction between the polypeptides of the invention and said rabbit polyclonal antiserum raised against the $P_{32}$ protein of BCG:

the test used was an ELISA test; the ELISA for antibody determination is based on the method of Engvall and Perlmann (Engvall, E., and P. Perlmann. 1971. Enzyme-linked immunosorbent assay (ELISA). Quantitative assay of immunoglobulin G. Immunochemistry 8:871–874)

Immulon Microelisa plates (Dynatech, Kloten, Switzerland) are coated by adding to each well 1 µg of one of the polypeptides of the invention in 100 µl Tris hydrochloride buffer 50 mM (pH 8.2). After incubation for 2 h at 27° C. in a moist chamber, the plates are kept overnight at 4° C. They are washed four times with 0.01 M phosphate-buffered saline (pH 7.2) containing 0.05% Tween 20 by using a Titertek microplate washer (Flow Laboratories. Brussels. Belgium). Blocking is done with 0.5% gelatin in 0.06 M carbonate buffer (pH 9.6) for 1 h. Wells are then washed as before, and 100 µl of above mentioned serum diluted in phosphate-buffered saline containing 0.05% Tween 20 and 0.5% gelatin is added. According to the results obtained in preliminary experiments, the working dilutions are set at 1:200 for IgG, 1:20 for IgA and 1:80 for IgM determinations. Each dilution is run in duplicate. After 2 h of incubation and after the wells are washed, they are filled with 100 µl of peroxidase-conjugated rabbit immunoglobulins directed against human IgG, IgA or IgM (Dakopatts, Copenhagen, Denmark), diluted 1:400, 1:400 and 1:1,200, respectively in phosphate-buffered saline containing 0.05% Tween 20 and 0.5% gelatin and incubated for 90 min. After the wash, the amount of peroxidase bound to the wells is quantified by using a freshly prepared solution of o-phenylenediamine (10 mg/100 ml) and hydrogen peroxide (8 µl of 30% $H_2O_2$ per 100 ml) in 0.15 M citrate buffer (pH 5.0) as a substrate. The enzymatic reaction is stopped with 8 N $H_2SO_4$ after 15 min. of incubation. The optical density is read at 492 nm with a Titertek Multiskan photometer (Flow Laboratories).

Wells without sera are used as controls for the conjugates. Each experiment is done by including on each plate one negative and two positive reference sera with medium and low antibody levels to correct for plate-to-plate and day-to-day variations. The antibody concentrations are expressed as the optical density values obtained after correction of the readings according to the mean variations of the reference sera.

Hereafter is also given in a non limitative way, a test for giving evidence of the fact that polypeptides of the invention are recognized selectively by human sera from tuberculous patients.

This test is an immunoblotting (Western blotting) analysis, in the case where the polypeptides of the invention are obtained by recombinant techniques. This test can also be used for polypeptides of the invention obtained by a different preparation process. After sodium dodecyl sulfate-polyacrylamide gel electrophoresis, polypeptides of the invention are blotted onto nitrocellulose membranes (Hybond C. (Amersham)) as described by Towbin et al. (29). The expression of polypeptides of the invention fused to β-galactosidase in E. coli Y1089, is visualized by the binding of a polyclonal rabbit anti-32-kDa BCG protein serum (1:1,000) or by using a monoclonal anti-β-galactosidase antibody (Promega). The secondary antibody (alkaline phosphatase anti-rabbit immunoglobulin G and anti-mouse alkaline phosphatase immunoglobulin G conjugates, respectively) is diluted as recommended by the supplier (Promega).

In order to identify selective recognition of polypeptides of the invention and of fusion proteins of the invention by human tuberculous sera, nitrocellulose sheets are incubated overnight with these sera (1:50) (after blocking aspecific protein-binding sites). The human tuberculous sera are selected for their reactivity (high or low) against the purified 32-kDa antigen of BCG tested in a dot blot assay as described in document (31) of the bibliography hereafter. Reactive areas on the nitrocellulose sheets are revealed by incubation with peroxidase conjugated goat anti-human immunoglobulin G antibody (Dakopatts, Copenhagen, Denmark) (1:200) for 4 h, and after repeated washings, color reaction is developed by adding peroxidase substrate (α-chloronaphtol) (Bio-Rad Laboratories, Richmond, Calif.) in the presence of peroxidase and hydrogen peroxide.

It goes without saying that the free reactive functions which are present in some of the amino acids, which are part of the constitution of the polypeptides of the invention, particularly the free carboxyl groups which are carried by the groups Glu or by the C-terminal amino acid on the one hand and/or the free NH$_2$ groups carried by the N-terminal amino acid or by amino acid inside the peptidic chain, for instance Lys, on the other hand, can be modified in so far as this modification does not alter the above mentioned properties of the polypeptide.

The molecules which are thus modified are naturally part of the invention. The above mentioned carboxyl groups can be acylated or esterified.

Other modifications are also part of the invention. Particularly, the amine or ester functions or both of terminal amino acids can be themselves involved in the bond with other amino acids. For instance, the N-terminal amino acid can be linked to a sequence comprising from 1 to several amino acids corresponding to a part of the C-terminal region of another peptide.

Furthermore, any peptidic sequences resulting from the modification by substitution and/or by addition and/or by deletion of one or several amino acids of the polypeptides according to the invention are part of the invention in so far as this modification does not alter the above mentioned properties of said polypeptides.

The polypeptides according to the invention can be glycosylated or not, particularly in some of their glycosylation sites of the type Asn-X-Ser or Asn-X-Thr, X representing any amino acid.

Advantageous recombinant polypeptides of the invention contain in their polypeptidic chain, one at least of the following amino acid sequences:

the one extending from the extremity constituted by amino acid at position (−42) to the extremity constituted by amino acid at position (−1) represented on FIG. 3a and FIG. 3b, the one extending from the extremity constituted by amino acid at position (−47) to the extremity constituted by amino acid at position (−1) represented on FIG. 3a and FIG. 3b, the one extending from the extremity constituted by amino acid at position (−49) to to the extremity constituted by amino acid at position (−1) represented on FIG. 3a and FIG. 3b, the one extending from the extremity constituted by amino acid at position (−55) to the extremity constituted by amino acid at position (−1) represented on FIG. 3a and FIG. 3b, the one extending from the extremity constituted by amino acid at position (−59) to the extremity constituted by amino acid at position (−1) represented on FIG. 3a and FIG. 3b.

Advantageous recombinant polypeptides of the invention contain in their polypeptidic chain, one at least of the following amino acid sequences:

the one extending from the extremity constituted by amino acid at position (−42) to the extremity constituted by amino acid at position (−1) represented on FIG. 4a and FIG. 4b, the one extending from the extremity constituted by amino acid at position (−47) to the extremity constituted by amino acid at position (−1) represented on FIG. 4a and FIG. 4b, the one extending from the extremity constituted by amino acid at position (−49) to to the extremity constituted by amino acid at position (−1) represented on FIG. 4a and FIG. 4b, the one extending from the extremity constituted by amino acid at position (−55) to the extremity constituted by amino acid at position (−1) represented on FIG. 4a and FIG. 4b, the one extending from the extremity constituted by amino acid at position (−59) to the extremity constituted by amino acid at position (−1) represented on FIG. 4a and FIG. 4b.

Advantageous recombinant polypeptides of the invention contain in their polypeptidic chain, one at least of the following amino acid sequences:

the one extending from the extremity constituted by amino acid at position (−43) to the extremity constituted by amino acid at position (−1) represented on FIG. 5.

Advantageous recombinant polypeptides of the invention contain in their polypeptidic chain, one at least of the following amino acid sequences:

the one extending from the extremity constituted by amino acid at position (1) to the extremity constituted by amino acid at position (294) represented on FIG. 3a and FIG. 3b, the one extending from the extremity constituted by amino acid at position (−29) to the extremity constituted by amino acid at position (294) represented on FIG. 3a and FIG. 3b, the one extending from the extremity constituted by amino acid at position (−42) to the extremity constituted by amino acid at position (294) represented on FIG. 3a and FIG. 3b, the one extending from the extremity constituted by amino acid at position (−47) to the extremity constituted by amino acid at position (294) represented on FIG. 3a and FIG. 3b, the one extending from the extremity constituted by amino acid at position (−49) to the extremity constituted by amino acid at position (294) represented on FIG. 3a and FIG. 3b, the one extending from the extremity constituted by amino acid at position (−55) to the extremity constituted by amino acid at position (294) represented on FIG. 3a and FIG. 3b, the one extending from the extremity constituted by amino acid at position (−59) to the extremity constituted by amino acid at position (294) represented on FIG. 3a and FIG. 3b.

Advantageous recombinant polypeptides of the invention contain in their polypeptidic chain, one at least of the following amino acid sequences:

the one extending from the extremity constituted by amino acid at position (1) to the extremity constituted by amino acid at position (294) represented on FIG. 4a and FIG. 4b, the one extending from the extremity constituted by amino acid at position (−29) to the extremity constituted by amino acid at position (294) represented on FIG. 4a and FIG. 4b, the one extending from the extremity constituted by amino acid at position (−42) to the extremity constituted by amino acid at position (294) represented on FIG. 4a and FIG. 4b, the one extending from the extremity constituted by amino acid at position (−47) to the extremity constituted by amino acid at position (294) represented on FIG. 4a and FIG. 4b, the one extending from the extremity constituted by amino acid at position (−49) to the extremity constituted by amino acid at position (294) represented on FIG. 4a and FIG. 4b, the one extending from the extremity constituted by amino acid at position (−55) to the extremity constituted by amino acid at position (294) represented on FIG. 4a and FIG. 4b, the one extending from the extremity constituted by amino acid at position (−59) to the extremity constituted by amino acid at position (294) represented on FIG. 4a and FIG. 4b.

Advantageous recombinant polypeptides of the invention contain in their polypeptidic chain, one at least of the following amino acid sequences:

the one extending from the extremity constituted by amino acid at position (1) to the extremity constituted by amino acid at position (295) represented on FIG. 5, the one extending from the extremity constituted by amino acid at position (−30) to the extremity constituted by amino acid at position (295) represented on FIG. 5, the one extending from the extremity constituted by amino acid at position (−43) to the extremity constituted by amino acid at position (295) represented on FIG. 5.

Other advantageous recombinant polypeptides of the invention consist in one of the following amino acid sequences:

the one extending from the extremity constituted by amino acid at position (−59) to the extremity constituted by amino acid at position (294) represented on FIG. 3a and FIG. 3b, the one extending from the extremity constituted by amino acid at position (−55) to the extremity constituted by amino acid at position (294) represented on FIG. 3a and FIG. 3b, the one extending from the extremity constituted by amino acid at position (−49) to the extremity constituted by amino acid at position (294) represented on FIG. 3a and FIG. 3b, the one extending from the extremity constituted by amino acid at position (−47) to the extremity constituted by amino acid at position (294) represented on FIG. 3a and FIG. 3b, the one extending from the extremity constituted by amino acid at position (−42) to the extremity constituted by amino acid at position (294) represented on FIG. 3a and FIG. 3b, the one extending from the extremity constituted by amino acid at position (−29) to the extremity constituted by amino acid at position (294) represented on FIG. 3a and FIG. 3b, the one extending from the extremity constituted by amino acid at position (1) to the extremity constituted by amino acid at position (294) represented on FIG. 3a and FIG. 3b.

Other advantageous recombinant polypeptides of the invention consist in one of the following amino acid sequences:

the one extending from the extremity constituted by amino acid at position (−59) to the extremity constituted by amino acid at position (−294) represented on FIG. 4a and FIG. 4b, the one extending from the extremity constituted by amino acid at position (−55) to the extremity constituted by amino acid at position (294) represented on FIG. 4a and FIG. 4b, the one extending from the extremity constituted by amino acid at position (−49) to the extremity constituted by amino acid at position (294) represented on FIG. 4a and FIG. 4b, the one extending from the extremity constituted by amino acid at position (−47) to the extremity constituted by amino acid at position (294) represented on FIG. 4a and FIG. 4b, the one extending from the extremity constituted by amino acid at position (−42) to the extremity constituted by amino acid at position (294) represented on FIG. 4a and FIG. 4b, the one extending from the extremity constituted by amino acid at position (−29) to the extremity constituted by amino acid at position (294) represented on FIG. 4a and FIG. 4b, the one extending from the extremity constituted by amino acid at position (1) to the extremity constituted by amino acid at position (294) represented on FIG. 4a and FIG. 4b.

Other advantageous recombinant polypeptides of the invention consist in one of the following amino acid sequences:

the one extending from the extremity constituted by amino acid at position (1) to the extremity constituted by amino acid at position (295) represented on FIG. 5, the one extending from the extremity constituted by amino acid at position (−30) to the extremity constituted by amino acid at position (295) represented on FIG. 5, the one extending from the extremity constituted by amino acid at position (−43) to the extremity constituted by amino acid at position (295) represented on FIG. 5.

Other advantageous recombinant polypeptides of the invention consist in one of the following amino acid sequences:

the one extending from the extremity constituted by amino acid at position (−59) to the extremity constituted by amino acid at position (−1) represented on FIG. 3a and FIG. 3b the one extending from the extremity constituted by amino acid at position (−55) to the extremity constituted by amino acid at position (−1) represented on FIG. 3a and FIG. 3b, the one extending from the extremity constituted by amino acid at position (−49) to the extremity constituted by amino acid at position (−1) represented on FIG. 3a and FIG. 3b, the one extending from the extremity constituted by amino acid at position (−47) to the extremity constituted by amino acid at position (−1) represented on FIG. 3a and FIG. 3b, the one extending from the extremity constituted by amino acid at position (−42) to the extremity constituted by amino acid at position (−1) represented on FIG. 3a and FIG. 3b, the one extending from the extremity constituted by amino acid at position (−29) to the extremity constituted by amino acid at position (−1) represented on FIG. 3a and FIG. 3b.

Other advantageous recombinant polypeptides of the invention consist in one of the following amino acid sequences:

the one extending from the extremity constituted by amino acid at position (−59) to the extremity constituted by amino acid at position (−1) represented on FIG. 4a and FIG. 4b, the one extending from the extremity constituted by amino acid at position (−55) to the extremity constituted by amino acid at position (−1) represented on FIG. 4a and FIG. 4b, the one extending from the extremity constituted by amino acid at position (−49) to the extremity constituted by amino acid at position (−1) represented on FIG. 4a and FIG. 4b, the one extending from the extremity constituted by amino acid at position (−47) to the extremity constituted by amino acid at position (−1) represented on FIG. 4a and FIG. 4b, the one extending from the extremity constituted by amino acid at position (−42) to the extremity constituted by amino acid at position (−1) represented on FIG. 4a and FIG. 4b, the one extending from the extremity constituted by amino acid at position (−29) to the extremity constituted by amino acid at position (−1) represented on FIG. 4a and FIG. 4b.

Other advantageous recombinant polypeptides of the invention consist in one of the following amino acid sequences:

the one extending from the extremity constituted by amino acid at position (−43) to the extremity constituted by amino acid at position (−1) represented on FIG. 5, the one extending from the extremity constituted by amino acid at position (−30) to the extremity constituted by amino acid at position (−1) represented on FIG. 5.

In eukaryotic cells, these polypeptides can be used as signal peptides, the role of which is to initiate the translocation of a protein from its site of synthesis, but which is excised during translocation.

Other advantageous peptides of the invention consist in one of the following amino acid sequence:

the one extending from the extremity constituted by amino acid at position (12) to the extremity constituted by amino acid at position (31) represented on FIG. 3a and FIG. 3b, or the one extending from the extremity constituted by amino acid at position (36) to the extremity constituted by amino acid at position (55) represented on FIG. 3a and FIG. 3b, or the one extending from the extremity constituted by amino acid at position (77) to the extremity constituted by amino acid at position (96) represented on FIG. 3a and FIG. 3b, or the one extending from the extremity constituted by amino acid at position (101) to the extremity constituted by amino acid at position (120) represented on FIG. 3a and FIG. 3b, or the one extending from the extremity constituted by amino acid at position (175) to the extremity constituted by amino acid at position (194) represented on FIG. 3a and FIG. 3b, or the one extending from the extremity constituted by amino acid at position (211) to the extremity constituted by amino acid at position (230) represented on FIG. 3a and FIG. 3b, or the one extending from the extremity constituted by amino acid at position (275) to the extremity constituted by amino acid at position (294) represented on FIG. 3a and FIG. 3b.

Other advantageous peptides of the invention consist in one of the following amino acid sequence:

the one extending from the extremity constituted by amino acid at position (12) to the extremity constituted by amino acid at position (31) represented on FIG. 4a and FIG. 4b, or the one extending from the extremity constituted by amino acid at position (36) to the extremity constituted by amino acid at position (55) represented on FIG. 4a and FIG. 4b, or the one extending from the extremity constituted by amino acid at position (77) to the extremity constituted by amino acid at position (96) represented on FIG. 4a and FIG. 4b, or the one extending from the extremity constituted by amino acid at position (101) to the extremity constituted by amino acid at position (120) represented on FIG. 4a and FIG. 4b, or the one extending from the extremity constituted by amino acid at position (175) to the extremity constituted by amino acid at position (194) represented on FIG. 4a and FIG. 4b, or the one extending from the extremity constituted by amino acid at position (211) to the extremity constituted by amino acid at position (230) represented on FIG. 4a and FIG. 4b, or the one extending from the extremity constituted by amino acid at position (275) to the extremity constituted by amino acid at position (294) represented on FIG. 4a and FIG. 4b.

Other advantageous peptides of the invention consist in one of the following amino acid sequence:

the one extending from the extremity constituted by amino acid at position (12) to the extremity constituted by amino acid at position (31) represented on FIG. 5, or the one extending from the extremity constituted by amino acid at position (36) to the extremity constituted by amino acid at position (55) represented on FIG. 5, or the one extending from the extremity constituted by amino acid at position (77) to the extremity constituted by amino acid at position (96) represented on FIG. 5, or the one extending from the extremity constituted by amino acid at position (101) to the extremity constituted by amino acid at position (120) represented on FIG. 5, or the one extending from the extremity constituted by amino acid at position (175) to the extremity constituted by amino acid at position (194) represented on FIG. 5, or the one extending from the extremity constituted by amino acid at position (211) to the extremity constituted by amino acid at position (230) represented on FIG. 5, or the one extending from the extremity constituted by amino acid at position (275) to the extremity constituted by amino acid at position (295) represented on FIG. 5.

It is to be noted that the above mentioned polypeptides are derived from the expression products of a DNA derived from the nucleotide sequence coding for a protein of 32-kDa secreted by *Mycobacterium tuberculosis* as explained hereafter in the examples.

The invention also relates to the amino acid sequences constituted by the above mentioned polypeptides and a protein or an heterologous sequence with respect to said polypeptide, said protein or heterologous sequence comprising for instance from about 1 to about 1000 amino acids. These amino acid sequences will be called fusion proteins.

In an advantageous fusion protein of the invention, the heterologous protein is β-galactosidase.

Other advantageous fusion proteins of the invention are the ones containing an heterologous protein resulting from the expression of one of the following plasmids:

| pEX1 | |
| pEX2 | |
| pEX3 | |
| pUEX1 | pmTNF MPH |
| pUEX2 | |
| pUEX3 | |

The invention also relates to any nucleotide sequence coding for a polypeptide of the invention.

The invention also relates to nucleic acids comprising nucleotide sequences which hybridize with the nucleotide sequences coding for any of the above mentioned polypeptides under the following hybridization conditions:

hybridization and wash medium: 3×SSC, 20% formamide (1×SSC is 0.15 M NaCl, 0.015 M sodium citrate, pH 7.0), hybridization temperature (HT) and wash temperature (WT) for the nucleic acids of the invention defined by x-y: i.e. by the sequence extending from the extremity constituted by the nucleotide at position (x) to the extremity constituted by the nucleotide at position (y) represented on FIG. 3a and FIG. 3b.

| | |
|---|---|
| 1–182 | HT = WT = 69° C. |
| 1–194 | HT = WT = 69° C. |
| 1–212 | HT = WT = 69° C. |
| 1–218 | HT = WT = 69° C. |
| 1–272 | HT = WT = 69° C. |
| 1–359 | HT = WT = 71° C. |
| 1–1241 | HT = WT = 73° C. |
| 1–1358 | HT = WT = 73° C. |
| 183–359 | HT = WT = 70° C. |
| 183–1241 | HT = WT = 73° C. |
| 183–1358 | HT = WT = 73° C. |
| 195–359 | HT = WT = 70° C. |
| 195–1241 | HT = WT = 73° C. |
| 195–1358 | HT = WT = 73° C. |
| 213–359 | HT = WT = 70° C. |
| 213–1241 | HT = WT = 73° C. |
| 213–1358 | HT = WT = 73° C. |
| 219–359 | HT = WT = 71° C. |
| 219–1241 | HT = WT = 73° C. |
| 219–1358 | HT = WT = 73° C. |
| 234–359 | HT = WT = 71° C. |
| 234–1241 | HT = WT = 74° C. |
| 234–1358 | HT = WT = 73° C. |
| 273–359 | HT = WT = 71° C. |
| 273–1241 | HT = WT = 74° C. |
| 273–1358 | HT = WT = 73° C. |
| 360–1241 | HT = WT = 73° C. |
| 360–1358 | HT = WT = 73° C. |
| 1242–1358 | HT = WT = 62° C. |

The above mentioned temperatures are to be considered as approximately ±5° C.

The invention also relates to nucleic acids comprising nucleotide sequences which are complementary to the nucleotide sequences coding for any of the above mentioned polypeptides.

It is to be noted that in the above defined nucleic acids, as well as in the hereafter defined nucleic acids, the nucleotide sequences which are brought into play are such that T can be replaced by U.

A group of preferred nucleic acids of the invention comprises one at least of the following nucleotide sequences:

the one extending from the extremity constituted by nucleotide at position (1) to the extremity constituted by nucleotide at position (182) represented in FIG. 3a and FIG. 3b, the one extending from the extremity constituted by nucleotide at position (273) to the extremity constituted by nucleotide at position (359) represented in FIG. 3a and FIG. 3b, the one extending from the extremity constituted by nucleotide at position (360) to the extremity constituted by nucleotide at position (1241) represented in FIG. 3a and FIG. 3b, the one extending from the extremity constituted by nucleotide at position (1242) to the extremity constituted by nucleotide at position (1358), wherein N represents one of the five A, T, C, G or I nucleotides, represented in FIG. 3a and FIG. 3b, or above said nucleotide sequences wherein T is replaced by U, or nucleic acids which hybridize with said above mentioned nucleotide sequences or the complementary sequences thereof.

A group of preferred nucleic acids of the invention comprises one at least of the following nucleotide sequences:

the one extending from the extremity constituted by nucleotide at position (1) to the extremity constituted by nucleotide at position (182) represented in FIG. 4a and FIG. 4b, the one extending from the extremity constituted by nucleotide at position (273) to the extremity constituted by nucleotide at position (359) represented in FIG. 4a and FIG. 4b, the one extending from the extremity constituted by nucleotide at position (360) to the extremity constituted by nucleotide at position (1241) represented in FIG. 4a and FIG. 4b, the one extending from the extremity constituted by nucleotide at position (1242) to the extremity constituted by nucleotide at position (1358), wherein N represents one of the five A, T, C, G or I nucleotides, represented in FIG. 4a and FIG. 4b, or above said nucleotide sequences wherein T is replaced by U, or nucleic acids which hybridize with said above mentioned nucleotide sequences or the complementary sequences thereof.

A group of preferred nucleic acids of the invention comprises one at least of the following nucleotide sequences:

the one extending from the extremity constituted by nucleotide at position (130) to the extremity constituted by nucleotide at position (219) represented in FIG. 5, the one extending from the extremity constituted by nucleotide at position (220) to the extremity constituted by nucleotide at position (1104) represented in FIG. 5, the one extending from the extremity constituted by nucleotide at position (1104) to the extremity constituted by nucleotide at position (1299), wherein N represents one of the five A, T, C, G or I nucleotides, represented in FIG. 5, or above said nucleotide sequences wherein T is replaced by U, or nucleic acids which hybridize with said above mentioned nucleotide sequences or the complementary sequences thereof.

Other preferred nucleic acids of the invention comprise one at least of the following nucleotide sequences:

the one extending from the extremity constituted by nucleotide at position (195) to the extremity constituted by nucleotide at position (359) represented in FIG. 3a and FIG. 3b, the one extending from the extremity constituted by nucleotide at position (213) to the extremity constituted by nucleotide at position (359) represented in FIG. 3a and FIG. 3b, the one extending from the extremity constituted by nucleotide at position (219) to the extremity constituted by nucleotide at position (359) represented in FIG. 3a and FIG. 3b, the one extending from the extremity constituted by nucleotide at position (183) to the extremity constituted by nucleotide at position (359) represented in FIG. 3a and FIG. 3b.

Other preferred nucleic acids of the invention comprise one at least of the following nucleotide sequences:

the one extending from the extremity constituted by nucleotide at position (195) to the extremity constituted by nucleotide at position (359) represented in FIG. 4a and FIG. 4b, the one extending from the extremity constituted by nucleotide at position (213) to the extremity constituted by nucleotide at position (359) represented in FIG. 4a and FIG. 4b, the one extending from the extremity constituted by nucleotide at position (219) to the extremity constituted by nucleotide at position (359) represented in FIG. 4a and FIG. 4b, the one extending from the extremity constituted by nucleotide at position (183) to the extremity constituted by nucleotide at position (359) represented in FIG. 4a and FIG. 4b.

Another preferred group of nucleic acids of the invention comprises the following nucleotide sequences:

the one extending from the extremity constituted by nucleotide at position (360) to the extremity constituted by nucleotide at position (1358) represented, in FIG. 3a and FIG. 3b.

Another preferred group of nucleic acids of the invention comprises the following nucleotide sequences:

the one extending from the extremity constituted by nucleotide at position (360) to the extremity constituted by nucleotide at position (1358) represented in FIG. 4a and FIG. 4b.

According to another advantageous embodiment, nucleic acids of the invention comprises one of the following sequences:

the one extending from the extremity constituted by nucleotide at position (1) to the extremity constituted by nucleotide at position (194) represented in FIG. 3a and FIG. 3b, the one extending from the extremity constituted by nucleotide at position (1) to the extremity constituted by nucleotide at position (212) represented in FIG. 3a and FIG. 3b, the one extending from the extremity constituted by nucleotide at position (1) to the extremity constituted by nucleotide at position (218) represented in FIG. 3a and FIG. 3b, the one extending from the extremity constituted by nucleotide at position (1) to the extremity constituted by nucleotide at position (272) represented in FIG. 3a and FIG. 3b, the one extending from the extremity constituted by nucleotide at position (1) to the extremity constituted by nucleotide at position (359) represented in FIG. 3a and FIG. 3b, the one extending from the extremity constituted by nucleotide at position (1) to the extremity constituted by nucleotide at position (1358) represented in FIG. 3a and FIG. 3b, the one extending from the extremity constituted by nucleotide at position (1) to the extremity constituted by nucleotide at position (1241) represented in FIG. 3a and FIG. 3b, the one extending from the extremity constituted by nucleotide at position (183) to the extremity constituted by nucleotide at position (1358) represented in FIG. 3a and FIG. 3b, the one extending from the extremity constituted by nucleotide at position (183) to the extremity constituted by nucleotide at position (1241) represented in FIG. 3a and FIG. 3b, the one extending from the extremity constituted by nucleotide at position (195) to the extremity constituted by nucleotide at position (1358) represented in FIG. 3a and FIG. 3b, the one extending from the extremity constituted by nucleotide at position (195) to the extremity constituted by nucleotide at position (1241) represented in FIG. 3a and FIG. 3b, the one extending from the extremity constituted by nucleotide at position (213) to the extremity constituted by nucleotide at position (1358) represented in FIG. 3a and FIG. 3b, the one extending from the extremity constituted by nucleotide at position (213) to the extremity constituted by nucleotide at position (1241) represented in FIG. 3a and FIG. 3b, the one extending from the extremity constituted by nucleotide at position (219) to the extremity constituted by nucleotide at position (1358) represented in FIG. 3a and FIG. 3b, the one extending from the extremity constituted by nucleotide at position (219) to the extremity constituted by nucleotide at position (1241) represented in FIG. 3a and FIG. 3b, the one extending from the extremity constituted by nucleotide at position (234) to the extremity constituted by nucleotide at position (1358) represented in FIG. 3a and FIG. 3b, the one extending from the extremity constituted by nucleotide at position (234) to the extremity constituted by nucleotide at position (1241) represented in FIG. 3a and FIG. 3b, the one extending from the extremity constituted by nucleotide at position (273) to the extremity constituted by nucleotide at position (1241) represented in FIG. 3a and FIG. 3b, the one extending from the extremity constituted by nucleotide at position (273) to the extremity constituted by nucleotide at position (1358) represented in FIG. 3*a* and FIG. 3*b*.

According to another advantageous embodiment, nucleic acids of the invention comprises one of the following sequences:

the one extending from the extremity constituted by nucleotide at position (1) to the extremity constituted by nucleotide at position (194) represented in FIG. 4*a* and FIG. 4*b*, the one extending from the extremity constituted by nucleotide at position (1) to the extremity constituted by nucleotide at position (212) represented in FIG. 4*a* and FIG. 4*b*, the one extending from the extremity constituted by nucleotide at position (1) to the extremity constituted by nucleotide at position (218) represented in FIG. 4*a* and FIG. 4*b*, the one extending from the extremity constituted by nucleotide at position (1) to the extremity constituted by nucleotide at position (272) represented in FIG. 4*a* and FIG. 4*b*, the one extending from the extremity constituted by nucleotide at position (1) to the extremity constituted by nucleotide at position (359) represented in FIG. 4*a* and FIG. 4*b*, the one extending from the extremity constituted by nucleotide at position (1) to the extremity constituted by nucleotide at position (1358) represented in FIG. 4*a* and FIG. 4*b*, the one extending from the extremity constituted by nucleotide at position (1) to the extremity constituted by nucleotide at position (1241) represented in FIG. 4*a* and FIG. 4*b*, the one extending from the extremity constituted by nucleotide at position (183) to the extremity constituted by nucleotide at position (1358) represented in FIG. 4*a* and FIG. 4*b*, the one extending from the extremity constituted by nucleotide at position (183) to the extremity constituted by nucleotide at position (1241) represented in FIG. 4*a* and FIG. 4*b*, the one extending from the extremity constituted by nucleotide at position (195) to the extremity constituted by nucleotide at position (1358) represented in FIG. 4*a* and FIG. 4*b*, the one extending from the extremity constituted by nucleotide at position (195) to the extremity constituted by nucleotide at position (1241) represented in FIG. 4*a* and FIG. 4*b*, the one extending from the extremity constituted by nucleotide at position (213) to the extremity constituted by nucleotide at position (1358) represented in FIG. 4*a* and FIG. 4*b*, the one extending from the extremity constituted by nucleotide at position (213) to the extremity constituted by nucleotide at position (1241) represented in FIG. 4*a* and FIG. 4*b*, the one extending from the extremity constituted by nucleotide at position (219) to the extremity constituted by nucleotide at position (1358) represented in FIG. 4*a* and FIG. 4*b*, the one extending from the extremity constituted by nucleotide at position (219) to the extremity constituted by nucleotide at position (1241) represented in FIG. 4*a* and FIG. 4*b*, the one extending from the extremity constituted by nucleotide at position (234) to the extremity constituted by nucleotide at position (1358) represented in FIG. 4*a* and FIG. 4*b*, the one extending from the extremity constituted by nucleotide at position (234) to the extremity constituted by nucleotide at position (1241) represented in FIG. 4*a* and FIG. 4*b*, the one extending from the extremity constituted by nucleotide at position (273) to the extremity constituted by nucleotide at position (1241) represented in FIG. 4*a* and FIG. 4*b*, the one extending from the extremity constituted by nucleotide at position (273) to the extremity constituted by nucleotide at position (1358) represented in FIG. 4*a* and FIG. 4*b*.

Preferred nucleic acids of the invention consist in one of the following nucleotide sequences:

the one extending from the extremity constituted by nucleotide at position (183) to the extremity constituted by nucleotide at position (359) represented in FIG. 3*a* and FIG. 3*b*, the one extending from the extremity constituted by nucleotide at position (195) to the extremity constituted by nucleotide at position (359) represented in FIG. 3*a* and FIG. 3*b*, the one extending from the extremity constituted by nucleotide at position (213) to the extremity constituted by nucleotide at position (359) represented in FIG. 3*a* and FIG. 3*b*, the one extending from the extremity constituted by nucleotide at position (219) to the extremity constituted by nucleotide at position (359) represented in FIG. 3*a* and FIG. 3*b*, the one extending from the extremity constituted by nucleotide at position (234) to the extremity constituted by nucleotide at position (359) represented in FIG. 3*a* and FIG. 3*b*, the one extending from the extremity constituted by nucleotide at position (273) to the extremity constituted by nucleotide at position (359) represented in FIG. 3*a* and FIG. 3*b*.

Preferred nucleic acids of the invention consist in one of the following nucleotide sequences:

the one extending from the extremity constituted by nucleotide at position (183) to the extremity constituted by nucleotide at position (359) represented in FIG. 4*a* and FIG. 4*b*, the one extending from the extremity constituted by nucleotide at position (195) to the extremity constituted by nucleotide at position (359) represented in FIG. 4*a* and FIG. 4*b*, the one extending from the extremity constituted by nucleotide at position (213) to the extremity constituted by nucleotide at position (359) represented in FIG. 4*a* and FIG. 4*b*, the one extending from the extremity constituted by nucleotide at position (219) to the extremity constituted by nucleotide at position (359) represented in FIG. 4*a* and FIG. 4*b*, the one extending from the extremity constituted by nucleotide at position (234) to the extremity constituted by nucleotide at position (359) represented in FIG. 4*a* and FIG. 4*b*, the one extending from the extremity constituted by nucleotide at position (273) to the extremity constituted by nucleotide at position (359) represented in FIG. 4*a* and FIG. 4*b*.

These nucleotide sequence can be used as nucleotide signal sequences, coding for the corresponding signal peptide.

Preferred nucleic acids of the invention consist in one of the following nucleotide sequences:

the one extending from the extremity constituted by nucleotide at position (360) to the extremity constituted by nucleotide at position (1241) represented in FIG. 3*a* and FIG. 3*b*, the one extending from the extremity constituted by nucleotide at position (360) to the extremity constituted by nucleotide at position (1358) represented in FIG. 3*a* and FIG. 3*b*.

Preferred nucleic acids of the invention consist in one of the following nucleotide sequences:

the one extending from the extremity constituted by nucleotide at position (1) to the extremity constituted by nucleotide at position (182) represented in FIG. 3*a* and FIG. 3*b*, the one extending from the extremity constituted by nucleotide at position (1) to the extremity constituted by nucleotide at position (194) represented in FIG. 3*a* and FIG. 3*b*, the one extending from the extremity constituted by nucleotide at position (1) to the extremity constituted by nucleotide at position (212) represented in FIG. 3*a* and FIG. 3*b*, the one extending from the extremity constituted by nucleotide at position (1) to the extremity constituted by nucleotide at position (218) represented in FIG. 3*a* and FIG. 3*b*, the one extending from the extremity constituted by nucleotide at position (1) to the extremity constituted by nucleotide at position (272) represented in FIG. 3*a* and FIG. 3*b*, the one extending from the extremity constituted by nucleotide at position (1) to the extremity constituted by nucleotide at position (359) represented in FIG. 3*a* and FIG. 3*b*, the one extending from the extremity constituted by nucleotide at position (1) to the extremity constituted by nucleotide at position (1241) represented in FIG. 3*a* and FIG. 3*b*, the one extending from the extremity constituted by nucleotide at position (1) to the extremity constituted by nucleotide at position (1358) represented in FIG. 3*a* and FIG. 3*b*, the one extending from the extremity constituted by nucleotide at position (183) to the extremity constituted by nucleotide at position (1241) represented in FIG. 3*a* and FIG. 3*b*, the one extending from the extremity constituted by nucleotide at position (183) to the extremity constituted by nucleotide at position (1358) represented in FIG. 3*a* and FIG. 3*b*, the one extending from the extremity constituted by nucleotide at position (195) to the extremity constituted by nucleotide at position (1241) represented in FIG. 3*a* and FIG. 3*b*, the one extending from the extremity constituted by nucleotide at position (195) to the extremity constituted by nucleotide at position (1358) represented in FIG. 3*a* and FIG. 3*b*, the one extending from the extremity constituted by nucleotide at position (213) to the extremity constituted by nucleotide at position (1241) represented in FIG. 3*a* and FIG. 3*b*, the one extending from the extremity constituted by nucleotide at position (213) to the extremity constituted by nucleotide at position (1358) represented in FIG. 3*a* and FIG. 3*b*, the one extending from the extremity constituted by nucleotide at position (219) to the extremity constituted by nucleotide at position (1241) represented in FIG. 3*a* and FIG. 3*b*, the one extending from the extremity constituted by nucleotide at position (219) to the extremity constituted by nucleotide at position (1358) represented in FIG. 3*a* and FIG. 3*b*, the one extending from the extremity constituted by nucleotide at position (234) to the extremity constituted by nucleotide at position (1241) represented in FIG. 3*a* and FIG. 3*b*, the one extending from the extremity constituted by nucleotide at position (234) to the extremity constituted by nucleotide at position (1358) represented in FIG. 3*a* and FIG. 3*b*, the one extending from the extremity constituted by nucleotide at position (273) to the extremity constituted by nucleotide at position (1241) represented in FIG. 3*a* and FIG. 3*b*, the one extending from the extremity constituted by nucleotide at position (273) to the extremity constituted by nucleotide at position (1358) represented in FIG. 3*a* and FIG. 3*b*, the one extending from the extremity constituted by nucleotide at position (1242) to the extremity constituted by nucleotide at position (1358) represented in FIG. 3*a* and FIG. 3*b*.

Preferred nucleic acids of the invention consist in one of the following nucleotide sequences:

the one extending from the extremity constituted by nucleotide at position (360) to the extremity constituted by nucleotide at position (1241) represented in FIG. 4*a* and FIG. 4*b*, the one extending from the extremity constituted by nucleotide at position (360) to the extremity constituted by nucleotide at position (1358) represented in FIG. 4*a* and FIG. 4*b*.

Preferred nucleic acids of the invention consist in one of the following nucleotide sequences:

the one extending from the extremity constituted by nucleotide at position (1) to the extremity constituted by nucleotide at position (182) represented in FIG. 4*a* and FIG. 4*b*, the one extending from the extremity constituted by nucleotide at position (1) to the extremity constituted by nucleotide at position (194) represented in FIG. 4*a* and FIG. 4*b*, the one extending from the extremity constituted by nucleotide at position (1) to the extremity constituted by nucleotide at position (212) represented in FIG. 4*a* and FIG. 4*b*, the one extending from the extremity constituted by nucleotide at position (1) to the extremity constituted by nucleotide at position (218) represented in FIG. 4*a* and FIG. 4*b*, the one extending from the extremity constituted by nucleotide at position (1) to the extremity constituted by nucleotide at position (272) represented in FIG. 4a and FIG. 4b, the one extending from the extremity constituted by nucleotide at position (1) to the extremity constituted by nucleotide at position (359) represented in FIG. 4a and FIG. 4b, the one extending from the extremity constituted by nucleotide at position (1) to the extremity constituted by nucleotide at position (1241) represented in FIG. 4a and FIG. 4b, the one extending from the extremity constituted by nucleotide at position (1) to the extremity constituted by nucleotide at position (1358) represented in FIG. 4a and FIG. 4b, the one extending from the extremity constituted by nucleotide at position (183) to the extremity constituted by nucleotide at position (1241) represented in FIG. 4a and FIG. 4b, the one extending from the extremity constituted by nucleotide at position (183) to the extremity constituted by nucleotide at position (1358) represented in FIG. 4a and FIG. 4b, the one extending from the extremity constituted by nucleotide at position (195) to the extremity constituted by nucleotide at position (1241) represented in FIG. 4a and FIG. 4b, the one extending from the extremity constituted by nucleotide at position (195) to the extremity constituted by nucleotide at position (1358) represented in FIG. 4a and FIG. 4b, the one extending from the extremity constituted by nucleotide at position (213) to the extremity constituted by nucleotide at position (1241) represented in FIG. 4a and FIG. 4b, the one extending from the extremity constituted by nucleotide at position (213) to the extremity constituted by nucleotide at position (1358) represented in FIG. 4a and FIG. 4b, the one extending from the extremity constituted by nucleotide at position (219) to the extremity constituted by nucleotide at position (1241) represented in FIG. 4a and FIG. 4b, the one extending from the extremity constituted by nucleotide at position (219) to the extremity constituted by nucleotide at position (1358) represented in FIG. 4a and FIG. 4b, the one extending from the extremity constituted by nucleotide at position (234) to the extremity constituted by nucleotide at position (1241) represented in FIG. 4a and FIG. 4b, the one extending from the extremity constituted by nucleotide at position (234) to the extremity constituted by nucleotide at position (1358) represented in FIG. 4a and FIG. 4b, the one extending from the extremity constituted by nucleotide at position (273) to the extremity constituted by nucleotide at position (1241) represented in FIG. 4a and FIG. 4b, the one extending from the extremity constituted by nucleotide at position (273) to the extremity constituted by nucleotide at position (1358) represented in FIG. 4a and FIG. 4b, the one extending from the extremity constituted by nucleotide at position (1242) to the extremity constituted by nucleotide at position (1358) represented in FIG. 4a and FIG. 4b.

Preferred nucleic acids of the invention consist in one of the following nucleotide sequences:

the one extending from the extremity constituted by nucleotide at position (1) to the extremity constituted by nucleotide at position (129) represented in FIG. 5, the one extending from the extremity constituted by nucleotide at position (1) to the extremity constituted by nucleotide at position (219) represented in FIG. 5, the one extending from the extremity constituted by nucleotide at position (1) to the extremity constituted by nucleotide at position (1104) represented in FIG. 5, the one extending from the extremity constituted by nucleotide at position (1) to the extremity constituted by nucleotide at position (1299) represented in FIG. 5, the one extending from the extremity constituted by nucleotide at position (90) to the extremity constituted by nucleotide at position (219) represented in FIG. 5, the one extending from the extremity constituted by nucleotide at position (90) to the extremity constituted by nucleotide at position (1299) represented in FIG. 5, the one extending from the extremity constituted by nucleotide at position (90) to the extremity constituted by nucleotide at position (1104) represented in FIG. 5, the one extending from the extremity constituted by nucleotide at position (130) to the extremity constituted by nucleotide at position (1104) represented in FIG. 5, the one extending from the extremity constituted by nucleotide at position (130) to the extremity constituted by nucleotide at position (1299) represented in FIG. 5, the one extending from the extremity constituted by nucleotide at position (220) to the extremity constituted by nucleotide at position (1299) represented in FIG. 5.

Preferred nucleic acids of the invention consist in one of the following nucleotide sequences:

the one extending from the extremity constituted by nucleotide at position (1) to the extremity constituted by nucleotide at position (129) represented in FIG. 5, the one extending from the extremity constituted by nucleotide at position (1) to the extremity constituted by nucleotide at position (219) represented in FIG. 5, the one extending from the extremity constituted by nucleotide at position (1) to the extremity constituted by nucleotide at position (1104) represented in FIG. 5, the one extending from the extremity constituted by nucleotide at position (1) to the extremity constituted by nucleotide at position (1299) represented in FIG. 5, the one extending from the extremity constituted by nucleotide at position (90) to the extremity constituted by nucleotide at position (219) represented in FIG. 5, the one extending from the extremity constituted by nucleotide at position (90) to the extremity constituted by nucleotide at position (1104) represented in FIG. 5, the one extending from the extremity constituted by nucleotide at position (90) to the extremity constituted by nucleotide at position (1299) represented in FIG. 5, the one extending from the extremity constituted by nucleotide at position (130) to the extremity constituted by nucleotide at position (219) represented in FIG. 5, the one extending from the extremity constituted by nucleotide at position (130) to the extremity constituted by nucleotide at position (1104) represented in FIG. 5, the one extending from the extremity constituted by nucleotide at position (130) to the extremity constituted by nucleotide at position (1299) represented in FIG. 5, the one extending from the extremity constituted by nucleotide at position (220) to the extremity constituted by nucleotide at position (1104) represented in FIG. 5, the one extending from the extremity constituted by nucleotide at position (220) to the extremity constituted by nucleotide at position (1299) represented in FIG. 5, the one extending from the extremity constituted by nucleotide at position (1104) to the extremity constituted by nucleotide at position (1299) represented in FIG. 5.

The invention also relates to any recombinant nucleic acids containing at least a nucleic acid of the invention inserted in an heterologous nucleic acid.

The invention relates more particularly to recombinant nucleic acid such as defined, in which the nucleotide sequence of the invention is preceded by a promoter (particularly an inducible promoter) under the control of which the transcription of said sequence is liable to be processed and possibly followed by a sequence coding for transcription termination signals.

The invention also relates to the recombinant nucleic acids in which the nucleic acid sequences coding for the polypeptide of the invention and possibly the signal peptide, are recombined with control elements which are heterologous with respect to the ones to which they are normally associated within the bacteria gene and, more particularly, the regulation elements adapted to control their expression in the cellular host which has been chosen for their production.

The invention also relates to recombinant vectors, particularly for cloning and/or expression, comprising a vector sequence, notably of the type plasmid, cosmid or phage, and a recombinant nucleic acid of the invention, in one of the non essential sites for its replication.

Appropriate vectors for expression of the recombinant antigen are the following one:

| | | |
|---|---|---|
| pEX1 | pmTNF | MPH |
| pEX2 | pIGRI | |
| pEX3 | | |
| pUEX1 | | |
| pUEX2 | | |
| pUEX3 | | |

The pEX1, pEX2 and pEX3 vectors are commercially available and can be obtained from Boehringer Mannheim.

The pUEX1, pUEX2 and pUEX3 vectors are also commercially available and can be obtained from Amersham.

According to an advantageous embodiment of the invention, the recombinant vector contains, in one of its non essential sites for its replication, necessary elements to promote the expression of polypeptides according to the invention in a cellular host and possibly a promoter recognized by the polymerase of the cellular host, particularly an inducible promoter and possibly a signal sequence and/or an anchor sequence.

According to another additional embodiment of the invention, the recombinant vector contains the elements enabling the expression by *E. coli* of a nucleic acid according to the invention inserted in the vector, and particularly the elements enabling the expression of the gene or part thereof of β-galactosidase.

The invention also relates to a cellular host which is transformed by a recombinant vector according to the invention, and comprising the regulation elements enabling the expression of the nucleotide sequence coding for the polypeptide according to the invention in this host.

The invention also relates to a cellular host chosen from among bacteria such as *E. coli*, transformed by a vector as above defined, and defined hereafter in the examples, or chosen from among eukaryotic organism, such as CHO cells, insect cells, Sf9 cells [*Spodoptera frugiperda*] infected by the virus Ac NPV (*Autographa californica* nuclear polyhydrosis virus) containing suitable vectors such as pAc 373 pYM1 or pVC3, BmN [*Bombyx mori*] infected by the virus BmNPV containing suitable vectors such as pBE520 or p89B310.

The invention relates to an expression product of a nucleic acid expressed by a transformed cellular host according to the invention.

The invention also relates to nucleotidic probes, hybridizing with anyone of the nucleic acids or with their complementary sequences, and particularly the probes chosen among the following nucleotidic sequences gathered in Table 1, and represented in FIG. 9.

TABLE 1

| Probes A(i), A(ii), A(iii), A(iv) and A(v) | | |
|---|---|---|
| A(i) | CAGCTTGTTGACAGGGTTCGTGGC | (SEQ ID NO:1) |
| A(ii) | GGTTCGTGGCGCCGTCACG | (SEQ ID NO:2) |
| A(iii) | CGTCGCGCGCCTAGTGTCGG | (SEQ ID NO:3) |
| A(iv) | CGGCGCCGTCGGTGGCACGGCGA | (SEQ ID NO:4) |
| A(v) | CGTCGGCGCGGCCCTAGTGTCGG | (SEQ ID NO:5) |
| Probe B | | |
| | TCGCCCGCCCTGTACCTG | (SEQ ID NO:6) |
| Probe C | | |
| | GCGCTGACGCTGGCGATCTATC | (SEQ ID NO:7) |
| Probe D | | |
| | CCGCTGTTGAACGTCGGCAAG | (SEQ ID NO:8) |
| Probe E | | |
| | AAGCCGTCGGATCTGGGTGGCAAC | (SEQ ID NO:9) |
| Probes F(i), F(ii), F(iii) and F(iv) | | |
| F(i) | ACGGCACTGGGTGCCACGCCCAAC | (SEQ ID NO:10) |
| F(ii) | ACGCCCAACACCGGGCCCGCCGCA | (SEQ ID NO:11) |
| F(iii) | ACGGGCACTGGGTGCCACGCCCAAC | (SEQ ID NO:12) |
| F(iv) | ACGCCCCAACACCGGGCCCGCGCCCCA | (SEQ ID NO:13) | or their complementary nucleotidic sequences.

The hybridization conditions can be the following ones: hybridization and wash medium: 3×SSC, 20% formamide (1×SSC is 0.15 M NaCl, 0.015 M sodium citrate, pH 7.0), hybridization temperature (HT) and wash temperature (WT):

| (WT) ° C.: | HT and WT (° C.) |
|---|---|
| A(i) | 50 |
| A(ii) | 50 |
| A(iii) | 52 |
| A(iv) | 60 |
| A(v) | 52 |
| B | 48 |
| C | 50 |
| D | 45 |
| E | 52 |
| F(i) | 55 |
| F(ii) | 59 |
| F(iii) | 55 |
| F(iv) | 59 |

These probes might enable to differentiate *M. tuberculosis* from other bacterial strains and in particular from the following mycobacteria species:

*Mycobacterium marinum, Mycobacterium scrofulaceum, Mycobacterium gordonae, Mycobacterium szulgai, Mycobacterium intracellulare, Mycobacterium xenopi, Mycobacterium gastri, Mycobacterium nonchromogenicum, Mycobacterium terrae* and *Mycobacterium triviale*, and more particularly from *M. bovis, Mycobacterium kansasii, Mycobacterium avium, Mycobacterium phlei* and *Mycobacterium fortuitum*.

The invention also relates to DNA or RNA primers which can be used for the synthesis of nucleotidic sequences according to the invention by PCR (polymerase chain reaction technique), such as described in U.S. Pat. No. 4,683,202 and No. 4,683,195 and European Patent no 200362.

The invention also relates to any DNA or RNA primer constituted by about 15 to about 25 nucleotides of a nucleotide sequence coding for a polypeptide according to the invention.

The invention also relates to any DNA or RNA primer constituted by about 15 to about 25 nucleotides liable to hybridize with a nucleotide sequence coding for a polypeptide according to the invention.

The invention also relates to any DNA or RNA primer constituted by about 15 to about 25 nucleotides complementary to a nucleotide sequence coding for a polypeptide according to the invention.

The sequences which can be used as primers are given in Table 2 hereafter (sequences P1 to P6 or their complement) and illustrated in FIG. 9:

TABLE 2

| P1 | GAGTACCTGCAGGTGCCGTCGCCGTCGATGGGCCG | (SEQ ID NO:14) |
|---|---|---|
| P2 compl. | ATCAACACCCCGGCGTTCGAGTGGTAC | (SEQ ID NO:15) |
| P2 | GTACCACTCGAACGCCGGGCTGTTGAT | (SEQ ID NO:16) |
| P3 | TGCCAGACTTACAAGTGGGA | (SEQ ID NO:17) |
| P3 compl. | TCCCACTTGTAAGTCTGGCA | (SEQ ID NO:18) |
| P4 | TCCTGACCAGCGAGCTGCCG | (SEQ ID NO:19) |
| P4 compl. | CGGCAGCTCGCTGGTCAGGA | (SEQ ID NO:20) |

TABLE 2-continued

| P5 | CCTGATCGGCCTGGCGATGCGTGACGC | (SEQ ID NO:21) |
|---|---|---|
| P5 compl. | GCGTCACCCATCGCCAGGCCGATCAGC | (SEQ ID NO:22) |
| P6 compl. | GCGCCCCAGTACTCCCAGCTGTGCGT | (SEQ ID NO:23) | compl. = complement

The sequences can be combined in twelve different primer-sets (given in Table 3) which allow enzymatical amplification by the polymerase chain reaction (PCR) technique of any of the nucleotide sequences of the invention, and more particularly the one extending from the extremity constituted by nucleotide at position 1 to the extremity constituted by nucleotide at position 1358, as well as the nucleotide sequence of antigen a of BCG (17).

The detection of the PCR amplified product can be achieved by a hybridization reaction with an oligonucleotide sequence of at least 10 nucleotides which is located between PCR primers which have been used to amplify the DNA.

The PCR products of the nucleotide sequences of the invention can be distinguished from the α-antigen gene of BCG or part thereof by hybridization techniques (dot-spot, Southern blotting, etc.) with the probes indicated in Table 3. The sequences of these probes can be found in Table 1 hereabove.

TABLE 3

| | Primer set | Detection with probe |
|---|---|---|
| 1. | P1 and the complement of P2 | B |
| 2. | P1 and the complement of P3 | B |
| 3. | P1 and the complement of P4 | B |
| 4. | P1 and the complement of P5 | B or C |
| 5. | P1 and the complement of P6 | B, C, D or E |
| 6. | P2 and the complement of P5 | C |
| 7. | P2 and the complement of P6 | C, D or E |
| 8. | P3 and the complement of P5 | C |
| 9. | P3 and the complement of P6 | C, D or E |
| 10. | P4 and the complement of P5 | C |
| 11. | P4 and the complement of P6 | C, D or E |
| 12. | P5 and the complement of P6 | D or E |

It is to be noted that enzymatic amplification can also be achieved with all oligonucleotides with sequences of about 15 consecutive bases of the primers given in Table 2. Primers with elongation at the 5'-end or with a small degree of mismatch may not considerably affect the outcome of the enzymatic amplification if the mismatches do not interfere with the base-pairing at the 3'-end of the primers.

Specific enzymatic amplification of the nucleotide sequences of the invention and not of the BCG gene can be achieved when the probes (given in Table 1) or their complements are used as amplification primers.

When the above mentioned probes of Table 1 are used as primers, the primer sets are constituted by any of the nucleotide sequences (A, B, C, D, E, F) of Table 1 in association with the complement of any other nucleotide sequence, chosen from A, B, C, D, E or F, it being understood that sequence A means any of the sequences A(i), A(ii), A(iii), A(iv), A(v) and sequence F, any of the sequences F(i), F(ii), F(iii) and F(iv).

Advantageous primer sets for enzymatic amplification of the nucleotide sequence of the invention can be one of the following primer sets given in Table 3bis hereafter:

TABLE 3BIS

| | |
|---|---|
| A(i) or A(ii) or A(iii) or A(iv) or A(v) | and the complement of B |
| A(i) or A(ii) or A(iii) or A(iv) or A(v) | and the complement of C |
| B | and the complement of C |
| A(i) or A(ii) or A(iii) or A(iv) or A(v) | and the complement of F |
| A(i) or A(ii) or A(iii) or A(iv) or A(v) | and the complement of D |
| A(i) or A(ii) or A(iii) or A(iv) or A(v) | and the complement of E |
| B | and the complement of D |
| B | and the complement of E |
| B | and the complement of F |
| C | and the complement of D |
| C | and the complement of E |
| C | and the complement of F |
| D | and the complement of E |
| D | and the complement of F |
| E | and the complement of F |

A(i), A(ii), A(iii), A(iv), A(v), B, C, D, E and F having the nucleotide sequence indicated in Table 1.

In the case of amplification of a nucleotide sequence of the invention with any of the above mentioned primer sets defined in Table 3bis hereabove, the detection of the amplified nucleotide sequence can be achieved by a hybridization reaction with an oligonucleotide sequence of at least 10 nucleotides, said sequence being located between the PCR primers which have been used to amplify the nucleotide sequence. An oligonucleotide sequence located between said two primers can be determined from FIG. 9 where the primers A, B, C, D, E and F are represented by the boxed sequences respectively named probe region A, probe region B, probe region C, probe region D, probe region E and probe region F.

The invention also relates to a kit for enzymatic amplification of a nucleotide sequence by PCR technique and detection of the amplified nucleotide sequence containing one of the PCR primer sets defined in Table 3 and one of the detection probes of the invention, advantageously the probes defined in Table 1, or one of the PCR primer sets defined in Table 3bis, and a detection sequence consisting for instance in an oligonucleotide sequence of at least 10 nucleotides, said sequence being located (FIG. 9) between the two PCR primers constituting the primer set which has been used for amplifying said nucleotide sequence.

The invention also relates to a process for preparing a polypeptide according to the invention comprising the following steps:

the culture in an appropriate medium of a cellular host which has previously been transformed by an appropriate vector containing a nucleic acid according to the invention, the recovery of the polypeptide produced by the above said transformed cellular host from the above said culture medium, and the purification of the polypeptide produced, eventually by means of immobilized metal ion affinity chromatography (IMAC).

The polypeptides of the invention can be prepared according to the classical techniques in the field of peptide synthesis.

The synthesis can be carried out in homogeneous solution or in solid phase.

For instance, the synthesis technique in homogeneous solution which can be used is the one described by Houben-weyl in the book titled "Methode der organischen chemie" (Method of organic chemistry) edited by E. Wunsh, vol. 15-I et II. THIEME, Stuttgart 1974.

The polypeptides of the invention can also be prepared according to the method described by R. D. MERRIFIELD in the article titled "Solid phase peptide synthesis" (J. Am. Chem. Soc., 45, 2149–2154, 1964).

The invention also relates to a process for preparing the nucleic acids according to the invention.

A suitable method for chemically preparing the single-stranded nucleic acids (containing at most 100 nucleotides of the invention) comprises the following steps:

DNA synthesis using the automatic β-cyanoethyl phosphoramidite method described in Bioorganic Chemistry 4; 274–325, 1986.

In the case of single-stranded DNA, the material which is obtained at the end of the DNA synthesis can be used as such.

A suitable method for chemically preparing the double-stranded nucleic acids (containing at most 100 bp of the invention) comprises the following steps:

DNA synthesis of one sense oligonucleotide using the automatic β-cyanoethyl phosphoramidite method described in Bioorganic Chemistry 4; 274–325, 1986, and DNA synthesis of one anti-sense oligonucleotide using said above-mentioned automatic β-cyanoethyl phosphoramidite method, combining the sense and anti-sense oligonucleotides by hybridization in order to form a DNA duplex, cloning the DNA duplex obtained into a suitable plasmid vector and recovery of the DNA according to classical methods, such as restriction enzyme digestion and agarose gel electrophoresis.

A method for the chemical preparation of nucleic acids of length greater than 100 nucleotides—or bp, in the case of double-stranded nucleic acids—comprises the following steps:

assembling of chemically synthesized oligonucleotides, provided at their ends with different restriction sites, the sequences of which are compatible with the succession of amino acids in the natural peptide, according to the principle described in Proc. Nat. Acad. Sci. USA 80; 7461–7465, 1983, cloning the DNA thereby obtained into a suitable plasmid vector and recovery of the desired nucleic acid according to classical methods, such as restriction enzyme digestion and agarose gel electrophoresis.

The invention also relates to antibodies themselves formed against the polypeptides according to the invention.

It goes without saying that this production is not limited to polyclonal antibodies.

It also relates to any monoclonal antibody produced by any hybridoma liable to be formed according to classical methods from splenic cells of an animal, particularly of a mouse or rat, immunized against the purified polypeptide of the invention on the one hand, and of cells of a myeloma cell line on the other hand, and to be selected by its ability to produce the monoclonal antibodies recognizing the polypeptide which has been initially used for the immunization of the animals.

The invention also relates to any antibody of the invention labeled by an appropriate label of the enzymatic, fluorescent or radioactive type.

The peptides which are advantageously used to produce antibodies, particularly monoclonal antibodies, are the following ones gathered in Table 4:

TABLE 4a (see FIG. 4a and 4b)

| Amino acid position (NH$_2$-terminal) | | Amino acid position (COOH-terminal) | |
|---|---|---|---|
| 12 | QVPSPSMGRDIKVQFQSGGA | 31 | (SEQ ID NO:24) |
| 36 | LYLLDGLRAQDDFSGWDINT | 55 | (SEQ ID NO:25) |
| 77 | SFYSDWYQPACRKAGCQTYK | 96 | (SEQ ID NO:26) |
| 101 | LTSELPGWLQANRHVKPTGS | 120 | (SEQ ID NO:27) |
| 175 | KASDMWGPKEDPAWQRNDPL | 194 | (SEQ ID NO:28) |
| 211 | CGNGKPSDLGGNNLPAKFLE | 230 | (SEQ ID NO:29) |
| 275 | KPDLQRHWVPRPTPGPPQGA | 294 | (SEQ ID NO:30) |

TABLE 4b (see FIG. 5)

| Amino acid position (NH$_2$-terminal) | | Amino acid position (COOH-terminal) | |
|---|---|---|---|
| 77 | SFYSDWYQPACGKAGCQTYX | 96 | (SEQ ID NO:31) |
| 276 | PDLQRALGATPNTGPAPQCA | 295 | (SEQ ID NO:32) |

The amino acid sequences are given in the 1-letter code.

Variations of the peptides listed in Table 4 are also possible depending on their intended use. For example, if the peptides are to be used to raise antisera, the peptides may be synthesized with an extra cysteine residue added. This extra cysteine residue is preferably added to the amino terminus and facilitates the coupling of the peptide to a carrier protein which is necessary to render the small peptide immunogenic. If the peptide is to be labeled for use in radioimmune assays, it may be advantageous to synthesize the protein with a tyrosine attached to either the amino or carboxyl terminus to facilitate iodination. These peptides possess therefore the primary sequence of the peptides listed in Table 4 but with additional amino acids which do not appear in the primary sequence of the protein and whose sole function is to confer the desired chemical properties to the peptides.

The invention also relates to a process for detecting in vitro antibodies related to tuberculosis in a human biological sample liable to contain them, this process comprising contacting the biological sample with a polypeptide or a peptide according to the invention under conditions enabling an in vitro immunological reaction between said polypeptide and the antibodies which are possibly present in the biological sample and
the in vitro detection of the antigen/antibody complex which may be formed.

Preferably, the biological medium is constituted by a human serum.

The detection can be carried out according to any classical process.

By way of example a preferred method brings into play an immunoenzymatic process according to ELISA technique or immunofluorescent or radioimmunological (RIA) or the equivalent ones.

Thus the invention also relates to any polypeptide according to the invention labeled by an appropriate label of the enzymatic, fluorescent, radioactive . . . type.

Such a method for detecting in vitro antibodies related to tuberculosis comprises for instance the following steps:
deposit of determined amounts of a polypeptidic composition according to the invention in the wells of a titration microplate,
introduction into said wells of increasing dilutions of the serum to be diagnosed,
incubation of the microplate,
repeated rinsing of the microplate,
introduction into the wells of the microplate of labeled antibodies against the blood immunoglobulins,
the labeling of these antibodies being carried out by means of an enzyme which is selected from among the ones which are able to hydrolyze a substrate by modifying the absorption of the radiation of this latter at least at a given wave length,
detection by comparing with a control standard of the amount of hydrolyzed substrate.

The invention also relates to a process for detecting and identifying in vitro antigens of *M. tuberculosis* in a human biological sample liable to contain them, this process comprising:
contacting the biological sample with an appropriate antibody of the invention under conditions enabling an in vitro immunological reaction between said antibody and the antigens of *M. tuberculosis* which are possibly present in the biological sample and the in vitro detection of the antigen/antibody complex which may be formed.

Preferably, the biological medium is constituted by sputum, pleural effusion liquid, broncho-alveolar washing liquid, urine, biopsy or autopsy material.

Appropriate antibodies are advantageously monoclonal antibodies directed against the peptides which have been mentioned in Table 4.

The invention also relates to an additional method for the in vitro diagnostic of tuberculosis in a patient liable to be infected by *Mycobacterium tuberculosis* comprising the following steps:

the possible previous amplification of the amount of the nucleotide sequences according to the invention, liable to be contained in a biological sample taken from said patient by means of a DNA primer set as above defined, contacting the above mentioned biological sample with a nucleotide probe of the invention, under conditions enabling the production of an hybridization complex formed between said probe and said nucleotide sequence, detecting the above said hybridization complex which has possibly been formed.

To carry out the in vitro diagnostic method for tuberculosis in a patient liable to be infected by *Mycobacterium tuberculosis* as above defined, the following necessary or kit can be used, said necessary or kit comprising:

a determined amount of a nucleotide probe of the invention, advantageously the appropriate medium for creating an hybridization reaction between the sequence to be detected and the above mentioned probe, advantageously, reagents enabling the detection of the hybridization complex which has been formed between the nucleotide sequence and the probe during the hybridization reaction.

The invention also relates to an additional method for the in vitro diagnostic of tuberculosis in a patient liable to be infected by *Mycobacterium tuberculosis* comprising:

contacting a biological sample taken from a patient with a polypeptide or a peptide of the invention, under conditions enabling an in vitro immunological reaction between said polypeptide or peptide and the antibodies which are possibly present in the biological sample and the in vitro detection of the antigen/antibody complex which has possibly been formed.

To carry out the in vitro diagnostic method for tuberculosis in a patient liable to be infected by *Mycobacterium tuberculosis*, the following necessary or kit can be used, said necessary or kit comprising:

a polypeptide or a peptide according to the invention, reagents for making a medium appropriate for the immunological reaction to occur, reagents enabling to detect the antigen/antibody complex which has been produced by the immunological reaction, said reagents possibly having a label, or being liable to be recognized by a labeled reagent, more particularly in the case where the above mentioned polypeptide or peptide is not labeled.

The invention also relates to an additional method for the in vitro diagnostic of tuberculosis in a patient liable to be infected by *M. tuberculosis*, comprising the following steps:

contacting the biological sample with an appropriate antibody of the invention under conditions enabling an in vitro immunological reaction between said antibody and the antigens of *M. tuberculosis* which are possibly present in the biological sample and—the in vitro detection of the antigen/antibody complex which may be formed.

Appropriate antibodies are advantageously monoclonal antibodies directed against the peptides which have been mentioned in Table 4.

To carry out the in vitro diagnostic method for tuberculosis in a patient liable to be infected by *Mycobacterium tuberculosis*, the following necessary or kit can be used, said necessary or kit comprising:

an antibody of the invention, reagents for making a medium appropriate for the immunological reaction to occur, reagents enabling to detect the antigen/antibody complexes which have been produced by the immunological reaction, said reagent possibly having a label or being liable to be recognized by a label reagent, more particularly in the case where the above mentioned antibody is not labeled.

An advantageous kit for the diagnostic in vitro of tuberculosis comprises:

at least a suitable solid phase system, e.g. a microtiter-plate for deposition thereon of the biological sample to be diagnosed in vitro, a preparation containing one of the monoclonal antibodies of the invention, a specific detection system for said monoclonal antibody, appropriate buffer solutions for carrying out the immunological reaction between a test sample and said monoclonal antibody on the one hand, and the bonded monoclonal antibodies and the detection system on the other hand.

The invention also relates to a kit, as described above, also containing a preparation of one of the polypeptides or peptides of the invention, said antigen of the invention being either a standard (for quantitative determination of the antigen of *M. tuberculosis* which is sought) or a competitor, with respect to the antigen which is sought, for the kit to be used in a competition dosage process.

The invention also relates to an immunogenic composition comprising a polypeptide or a peptide according to the invention, in association with a pharmaceutically acceptable vehicle.

The invention also relates to a vaccine composition comprising among other immunogenic principles anyone of the polypeptides or peptides of the invention or the expression product of the invention, possibly coupled to a natural protein or to a synthetic polypeptide having a sufficient molecular weight so that the conjugate is able to induce in vivo the production of antibodies neutralizing *Mycobacterium tuberculosis*, or induce in vivo a cellular immune response by activating *M. tuberculosis* antigen-responsive T cells.

The peptides of the invention which are advantageously used as immunogenic principle have one of the following sequences:

TABLE 4a (see FIG. 4a and 4b)

| Amino acid position (NH$_2$-terminal) | | Amino acid position (COOH-terminal) | |
|---|---|---|---|
| 12 | QVPSPSMGRDIKVQFQSGGA | 31 | (SEQ ID NO:24) |
| 36 | LYLLDGLRAQDDFSGWDINT | 55 | (SEQ ID NO:25) |

TABLE 4a-continued (see FIG. 4a and 4b)

| Amino acid position (NH$_2$-terminal) | | Amino acid position (COOH-terminal) | |
|---|---|---|---|
| 77 | SFYSDWYQPACRKAGCQTYK | 96 | (SEQ ID NO:26) |
| 101 | LTSELPGWLQANRHVKPTGS | 120 | (SEQ ID NO:27) |
| 175 | KASDMWGPKEDPAWQRNDPL | 194 | (SEQ ID NO:28) |
| 211 | CGNGKPSDLGGNNLPAKFLE | 230 | (SEQ ID NO:29) |
| 275 | KPDLQRHWVPRPTPGPPQGA | 294 | (SEQ ID NO:30) |

TABLE 4b (see FIG. 5)

| Amino acid position (NH$_2$-terminal) | | Amino acid position (COOH-terminal) | |
|---|---|---|---|
| 77 | SFYSDWYQPACGKAGCQTYX | 96 | (SEQ ID NO:31) |
| 276 | PDLQRALGATPNTGPAPQCA | 295 | (SEQ ID NO:32) |

The amino acid sequences are given in the 1-letter code.

Other characteristics and advantages of the invention will appear in the following examples and the figures illustrating the invention.

BRIEF DESCRIPTION OF THE DRAWINGS

FIG. 1(A) corresponds to the EcoRI restriction analysis of clone 15, clone 16, clone 17, clone 19, clone 24 and EcoRI-HindIII digested lambda DNA-molecular weight marker lane (in kilobase pairs) (M) (Boehringer).

FIG. 1(B) corresponds to the immunoblotting analysis of crude lysates of *E. coli* lysogenized with clone 15, clone 16, clone 17, clone 19, clone 23 and clone 24.

Arrow (←) indicates fusion protein produced by recombinant λgt11-*M-tuberculosis* clones. Expression and immunoblotting were as described above. Molecular weight (indicated in kDa) were estimated by comparison with molecular weight marker (High molecular weight-SDS calibration kit, Pharmacia).

Figure 2:
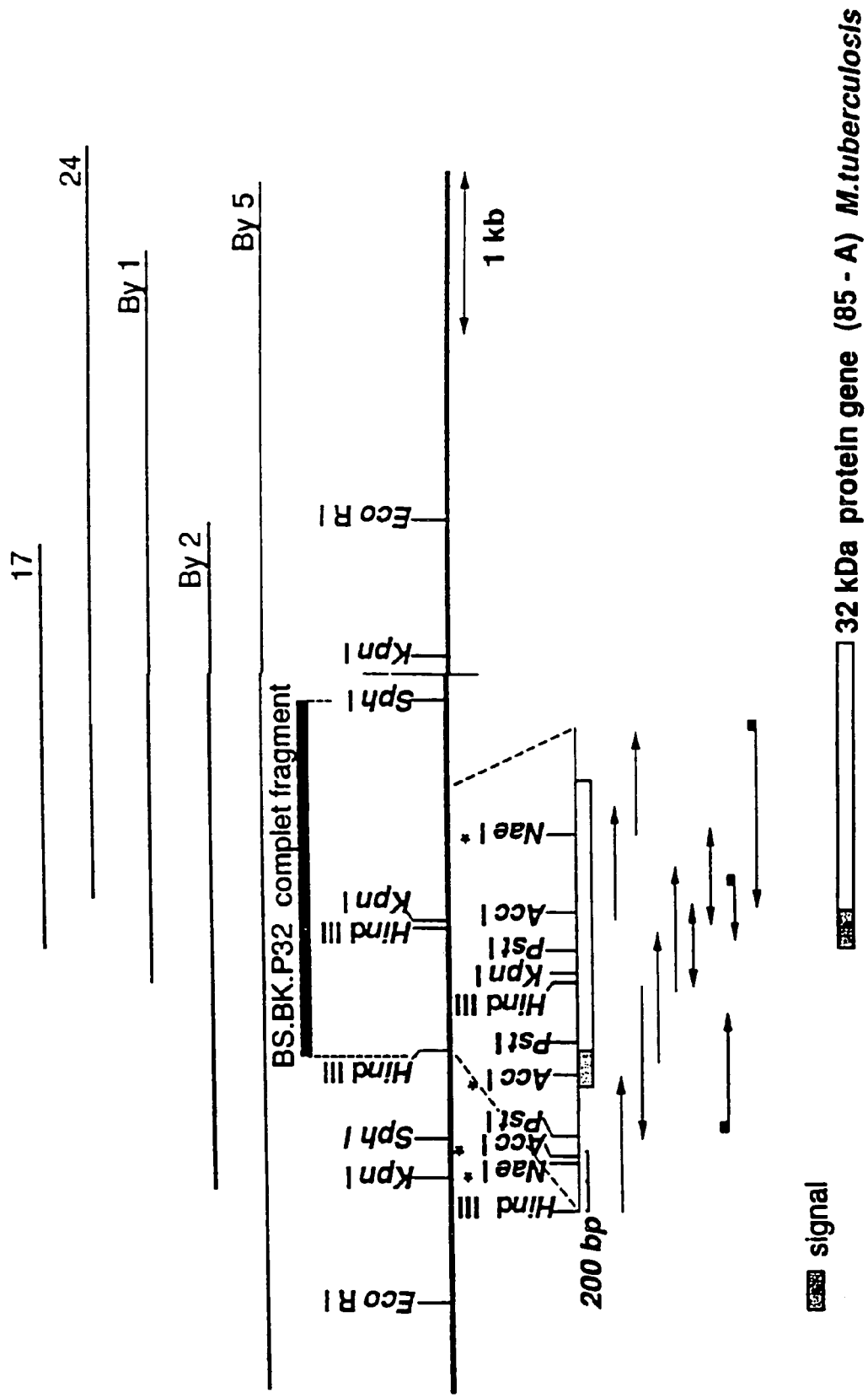

FIG. 2 corresponds to the restriction map of the DNA inserts in the λgt11 *M. tuberculosis* recombinant clones 17 and 24 identified with polyclonal anti-32-kDa (BCG) antiserum as above defined and of clones By1, By2 and By5 selected by hybridization with a 120 bp EcoRI-Kpn I restriction fragment of clone 17.

DNA was isolated from λgt11 phage stocks by using the Lambda Sorb Phage Immunoadsorbent, as described by the manufacturer (Promega). Restriction sites were located as described above. Some restriction sites (*) were deduced from a computer analysis of the nucleotide sequence.

The short vertical bars

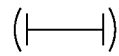

represent linker derived EcoRI sites surrounding the DNA inserts of recombinant clones. The lower part represents a magnification of the DNA region containing the antigen of molecular weight of 32-kDa, that has been sequenced. Arrows indicate strategies and direction of dideoxy-sequencing. (→) fragment subcloned in Bluescribe M13; (⇋) fragment subcloned in mp10 and mp11 M13 vectors; (■→) sequence determined with the use of a synthetic oligonucleotide.

FIGS. 3*a* and 3*b* correspond to the nucleotide (SEQ ID NO:34) and amino acid sequences (SEQ ID NO:35) of the general formula of the antigens of the invention.

FIGS. 4*a* and 4*b* correspond to the nucleotide (SEQ ID NO:36) and amino acid sequences (SEQ ID NO:37) of one of the antigens of the invention.

Two groups of sequences resembling the *E. coli* consensus promoter sequences are boxed and the homology to the consensus is indicated by italic bold letters. Roman bold letters represent a putative Shine-Dalgarno motif.

The NH$_2$-terminal amino acid sequence of the mature protein which is underlined with a double line happens to be very homologous—29/32 amino acids—with the one of MPB 59 antigen (34). Five additional ATG codons, upstream of the ATG at position 273 are shown (dotted underlined). Vertical arrows

indicate the presumed NH$_2$ end of clone 17 and clone 24. The option taken here arbitrarily represents the 59 amino acid signal peptide corresponding to ATG$_{183}$.

FIGS. 5*a*–5*c* correspond to the nucleotide (SEQ ID NO:38) and amino acid sequences (SEQ ID NO:39) of the antigen of 32-kDa of the invention.

The NH$_2$-terminal amino acid sequence of the mature protein which is underlined with a double line happens to be very homologous—29/32 amino acids—with the one of MPB 59 antigen (34). Vertical arrows (↓) indicate the presumed NH$_2$ end of clone 17 and clone 24.

Figure 6:
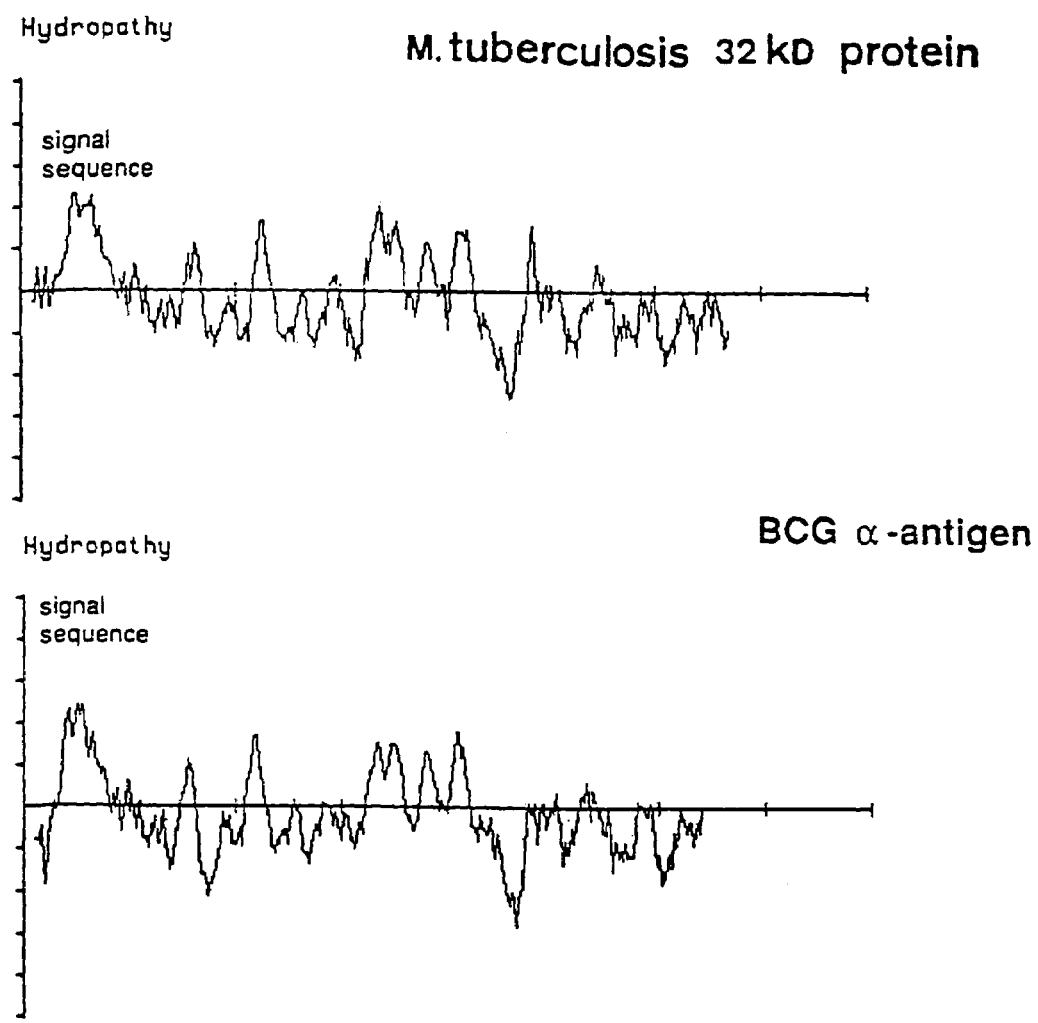

FIG. 6 is the hydropathy pattern of the antigen of the invention of a molecular weight of 32-kDa and of the antigen α of BCG (17).

FIGS. 7a–7b represent the homology between the amino acid sequences of the antigen of 32-kDa (SEQ ID NO:44) of the invention and of antigen α of BCG (SEQ ID NO:45) (revised version).

Identical amino acids; (:) evolutionarily conserved replacement of an amino acid (.), and absence of homology ( ) are indicated. Underlined sequence (=) represents the signal peptide, the option taken here arbitrarily representing the 43-amino acid signal peptide corresponding to ATG$_{91}$. Dashes in the sequences indicate breaks necessary for obtaining the optimal alignment.

Figure 8:
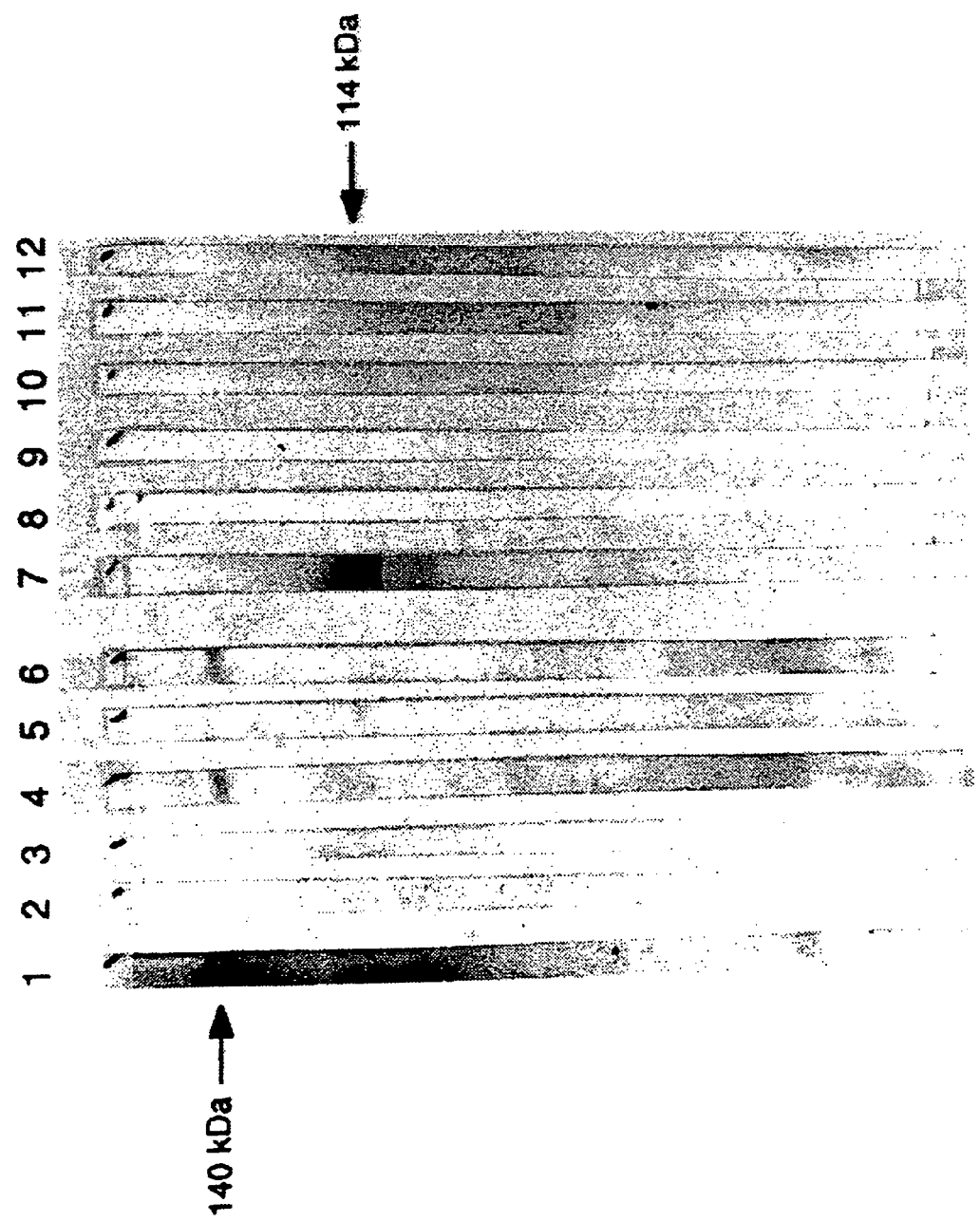

FIG. 8 illustrates the fact that the protein of 32-kDa of the invention is selectively recognized by human tuberculous sera.

FIG. 8 represents the immunoblotting with human tuberculous sera, and anti-β-galactosidase monoclonal antibody. Lanes 1 to 6: E. coli lysate expressing fusion protein (140 kDa); lanes 7 to 12: unfused β-galactosidase (114 kDa). The DNA insert of clone 17 (2.7 kb) was subcloned into pUEX$_2$ and expression of fusion protein was induced as described by Bresson and Stanley (4). Lanes 1 and 7 were probed with the anti-β-galactosidase monoclonal antibody: lanes 4, 5, 6 and 10, 11, 12 with 3 different human tuberculous sera highly responding towards purified protein of the invention of 32-kDa; lanes 2 and 3 and 8 and 9 were probed with 2 different low responding sera.

FIGS. 9a–9d represent the nucleic acid sequence alignment of the 32-kDa protein gene of M. tuberculosis of the invention (SEQ ID NO:46) (upper line), corresponding to the sequence in FIG. 5, of the gene of FIGS. 4a and 4b of the invention (SEQ ID NO:47) (middle line), and of the gene for antigen α of BCG (SEQ ID NO:48) (lower line).

Dashes in the sequence indicate breaks necessary for obtaining optimal alignment of the nucleic acid sequence.

FIG. 9a represents part of the nucleic acid sequence of the 32-kDA protein including probe region A and probe region B as well as primer region P1.

FIG. 9b represents part of the nucleic acid sequence of the 32-kDA protein including Primer regions P2, P3 and P4 and part of probe region C.

FIG. 9c represents part of the nucleic acid sequence of the 32-kDA protein including part of probe region C, probe regions D and E and primer region P5.

FIG. 9d represents part of the nucleic acid sequence of the 32 kDA protein including probe region F and primer region P6.

The primer regions for enzymatical amplification are boxed (P1 to P6).

The specific probe regions are boxed and respectively defined by probe region A, probe region B, probe region C, probe region D, probe region E and probe region F.

It is to be noted that the numbering of nucleotides is different from the numbering of FIG. 3a and FIG. 3b, and of FIG. 5, because nucleotide at position 1 (on FIG. 9) corresponds to nucleotide 234 on FIG. 3a, and corresponds to nucleotide 91 on FIG. 5.

Figure 10A:
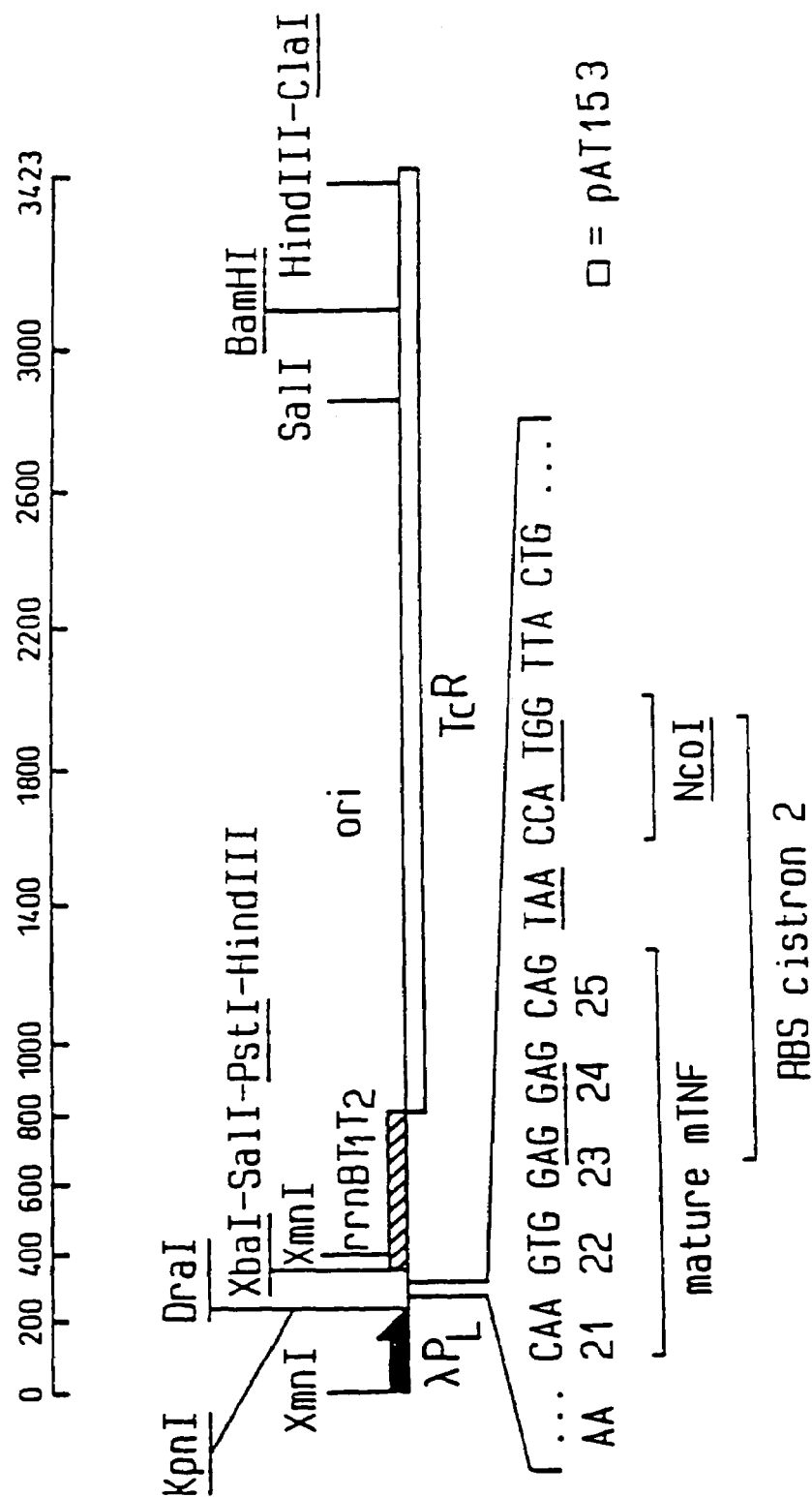

FIG. 10a corresponds to the restriction and genetic map of the pIGRI plasmid used in Example IV for the expression of the P$_{32}$ antigen of the invention in E. coli and contains SEQ ID NO:50.

On this figure, underlined restriction sites are unique.

FIGS. 10b–10m correspond to the pIGRI nucleic acid sequence (SEQ ID NO:40).

On this figure, the origin of nucleotide stretches used to construct plasmid pIGRI are specified hereafter.

| Position | |
|---|---|
| 3422–206 | lambda PL containing EcoRI blunt-MboII blunt fragment of pPL(λ) (Pharmacia) |
| 207–384 | synthetic DNA sequence |
| 228–230 | initiation codon ATG of first cistron |
| 234–305 | DNA encoding amino acids 2 to 25 of mature mouse TNF |
| 306–308 | stop codon (TAA) first cistron |
| 311–312 | initiation codon (ATG) second cistron |
| 385–890 | rrnBT$_1$T$_2$ containing HindIII-SspI fragment from pKK223 (Pharmacia) |
| 891–3421 | DraI-EcoRI blunt fragment of pAT$_{153}$ (Bioexcellence) containing the | tetracycline resistance gene and the origin of replication.

Table 5 hereafter corresponds to the complete restriction site analysis of pIGRI.

TABLE 5

RESTRICTION-SITE ANALYSIS

Name of the plasmid: pIGRI
Total number of bases is: 3423.
Analysis done on the complete sequence.

List of cuts by enzyme.

| | | | | | | | | | | |
|---|---|---|---|---|---|---|---|---|---|---|
| Acc I | 370 | 2765 | | | | | | | | |
| Acy I | 735 | 2211 | 2868 | 2982 | 3003 | | | | | |
| Afl III | 1645 | | | | | | | | | |
| Aha III | 222 | | | | | | | | | |
| Alu I | 386 | 1088 | 1345 | 1481 | 1707 | 2329 | 2732 | 3388 | 3403 | |
| Alw NI | 1236 | | | | | | | | | |
| Apa LI | 1331 | | | | | | | | | |
| Asp 718I | 208 | | | | | | | | | |
| Asu I | 329 | 494 | 623 | 713 | 1935 | 1977 | 2156 | 2280 | 2529 | 2617 | 289 |
| | 3244 | | | | | | | | | |
| Ava I | 1990 | | | | | | | | | |
| Ava II | 329 | 494 | 1935 | 1977 | 2280 | 2529 | 2617 | | | |
| Bal I | 1973 | | | | | | | | | |
| Bam HI | 3040 | | | | | | | | | |

TABLE 5-continued

RESTRICTION-SITE ANALYSIS

```
Bbe I      2214 2871 2985 3006
Bbv I       389 1316 1735 1753 1866 1869 2813 3202
Bbv I*     1017 1223 1226 1973 1997 2630
Bbv II     1822 2685
Bgl I      2253 2487
Bin I        15  903 1001 1087 3048
Bin I*      902  999 2313 3035
Bsp HI      855  925 2926
Bsp MI      382 2361
Bst NI      213  475  585  753 1486 1499 1620 1975 2358 3287
Cau II        4  683  716 1268 1933 2159 2883 3247
Cfr 10I    2132 2486 2646 3005 3014 3255
Cfr I      1971 2476 2884 3016 3120
Cla I      3393
Cvi JI      190  263  270  380  386  391  421  607  625  714   77
            791 1088 1117 1160 1171 1236 1315 1340 1345 1481  157
           1605 1623 1634 1707 1726 1926 1931 1973 2010 2092  213
           2157 2162 2300 2310 2329 2370 2427 2435 2465 2478  249
           2544 2588 2732 2748 2804 2822 2886 2894 2932 2946  301
           3087 3122 3245 3269 3388 3403
Cvi QI      209 3253
Dde I       133  336  343  518  608  664  962 1371 1835
Dpn I         9  236  897  909  995 1006 1081 1957 2274  228
           2320 2592 2951 3042 3069
Dra II     1935 1977 2892
Dra III     293
Dsa I       309 1968 2887
Eco 31I     562
Eco 47III   341 1773 2642 2923 3185
Eco 57I     214
Eco 57I*   1103
Eco 78I    2212 2869 2983 3004
Eco NI      196 2792
Eco RII     211  473  583  751 1484 1497 1618 1973 2356 3285
Eco RV     3232
Fnu 4HI     378  479 1031 1237 1240 1305 1448 1603 1721 1724  174
           1855 1858 1987 2001 2008 2011 2130 2209 2254 2311  239
           2479 2644 2695 2802 2836 2839 3117 3120 3191
Fnu DII     489 1021 1602 1784 1881 2003 2029 2174 2184 2313  237
           2440 2445 2472 2601 2716 3072
Fok I       415  799 3317
Fok I*      763 2370 2415 3269
Gsu I       339 2035
Gsu I*     2589
Hae I       775  791 1171 1623 1634 1973 2370 2427 2499
Hae II      343  541 1405 1775 2214 2644 2871 2925 2985 3006  318
Hae III     625  714  775  791 1171 1605 1623 1634 1973 2157  237
           2427 2478 2499 2588 2822 2886 2894 3018 3122 3245
Hga I       158  181  743 2035 2185 2776
Hga I*      955 1533 2429 2461 3015
Hgi AI      139 1335 1954 2245 2832 3143
Hgi CI      208 2126 2210 2649 2867 2981 3002 3296 3339
Hgi JII    2934 2948
Hha I       342  489  540 1021 1130 1304 1404 1471 1741 1774  196
           2000 2062 2213 2472 2603 2643 2718 2870 2924 2984  300
           3158 3186 3318
Hin P1I     340  487  538 1019 1128 1302 1402 1469 1739 1772  196
           1998 2060 2211 2470 2601 2641 2716 2868 2922 2982  300
           3156 3184 3316
Hind II     107  371 2766
Hind III    384 3386
Hinf I      367 1275 1671 1746 1891 2112 2410 2564 2784
Hpa II        3  682  716 1077 1267 1293 1440 1932 2133 2159  239
           2487 2647 2723 2883 3006 3015 3030 3247 3256
Hph I        94  138  181  663  914 1900 2121 2975 3020 3302
Hph I*        6
Kpn I       212
Mae I       364  899 1152 1928 3187
Mae II      274  698  944 1847 1871 2460 2516
Mae III     169  255  304  313 1109 1225 1288 2267 2534 3202  329
Mbo I         7  234  895  907  985  993 1004 1079 1955 2272  228
           2318 2590 2949 3040 3067
Mbo II      207  422  917 1779 1827 2419 2690
Mbo II*     988 2944
Mme I*     1252 1436 3112 3199
Mnl I      1218 1542 1948 2446 2630
Mnl I*      208  289  337  711 1467 1750 2116 2143 2181 2242  254
```

TABLE 5-continued

RESTRICTION-SITE ANALYSIS

|  |  |  |  |  |  |  |  |  |  |  |
|---|---|---|---|---|---|---|---|---|---|---|
|  | 2811 | 3030 | 3234 | 3294 |  |  |  |  |  |  |
| Mse I | 179 | 186 | 221 | 433 | 764 | 941 | 3361 | 3383 | 3420 |  |
| Mst I | 1963 | 2061 | 3157 |  |  |  |  |  |  |  |
| Nae I | 2134 | 2488 | 2648 | 3016 |  |  |  |  |  |  |
| Nar I | 2211 | 2868 | 2982 | 3003 |  |  |  |  |  |  |
| Nco I | 309 |  |  |  |  |  |  |  |  |  |
| Nhe I | 3186 |  |  |  |  |  |  |  |  |  |
| Nla III | 166 | 230 | 313 | 512 | 567 | 859 | 929 | 1649 | 1828 | 1962 | 216 |
|  | 2226 | 2241 | 2369 | 2486 | 2672 | 2711 | 2857 | 2930 | 3068 | 3415 |  |
| Nla IV | 210 | 330 | 496 | 1578 | 1617 | 1936 | 1979 | 2093 | 2128 | 2163 | 221 |
|  | 2530 | 2651 | 2869 | 2893 | 2983 | 3004 | 3042 | 3088 | 3298 | 3341 |  |
| Nru I | 2445 |  |  |  |  |  |  |  |  |  |
| Nsp BII | 1062 | 1307 | 2278 |  |  |  |  |  |  |  |
| Nsp HI | 1649 | 2857 |  |  |  |  |  |  |  |  |
| Pfl MI | 293 | 2052 | 2101 |  |  |  |  |  |  |  |
| Ple I | 375 | 1754 |  |  |  |  |  |  |  |  |
| Ple I* | 1269 | 2778 |  |  |  |  |  |  |  |  |
| Ppu MI | 1935 | 1977 |  |  |  |  |  |  |  |  |
| Pss I | 1938 | 1980 | 2895 |  |  |  |  |  |  |  |
| Pst I | 379 |  |  |  |  |  |  |  |  |  |
| Rsa I | 210 | 3254 |  |  |  |  |  |  |  |  |
| Sal I | 369 | 2764 |  |  |  |  |  |  |  |  |
| Scr FI | 4 | 213 | 475 | 585 | 683 | 716 | 753 | 1268 | 1486 | 1499 | 162 |
|  | 1933 | 1975 | 2159 | 2358 | 2883 | 3247 | 3287 |  |  |  |  |
| Sdu I | 139 | 1335 | 1954 | 2245 | 2832 | 2934 | 2948 | 3143 |  |  |  |
| Sec I | 3 | 309 | 1485 | 1968 | 2046 | 2248 | 2881 | 2887 | 3286 | 3300 |  |
| Sfa NI | 597 | 765 | 2392 | 2767 | 3178 | 3291 |  |  |  |  |  |
| Sfa NI* | 1548 | 1985 | 2380 | 3001 | 3013 | 3202 |  |  |  |  |  |
| Sph I | 2857 |  |  |  |  |  |  |  |  |  |
| Sso II | 2 | 211 | 473 | 583 | 681 | 714 | 751 | 1266 | 1484 | 1497 | 161 |
|  | 1931 | 1973 | 2157 | 2356 | 2881 | 3245 | 3285 |  |  |  |  |
| Sty I | 309 | 2046 |  |  |  |  |  |  |  |  |
| Taq I | 252 | 370 | 613 | 1547 | 2149 | 2290 | 2765 | 3078 | 3393 |  |  |
| Taq IIB | 1749 |  |  |  |  |  |  |  |  |  |
| Taq IIB* | 2751 |  |  |  |  |  |  |  |  |  |
| TthlllI | 38 | 1054 |  |  |  |  |  |  |  |  |
| TthlllI* | 633 | 1022 | 1061 |  |  |  |  |  |  |  |
| Xba I | 363 |  |  |  |  |  |  |  |  |  |
| Xho II | 7 | 895 | 907 | 993 | 1004 | 3040 |  |  |  |  |
| Xma III | 2476 |  |  |  |  |  |  |  |  |  |
| Xmn I | 414 |  |  |  |  |  |  |  |  |  |

Total number of cuts is: 705.

Sorted list of enzymes by n* of cuts.

| Cvi JI | 61 | Sdu I | 8 | TthlllI* | 3 | Ava I | 1 |
|---|---|---|---|---|---|---|---|
| Fnu 4HI | 31 | Cau II | 8 | Nsp BII | 3 | Taq IIB | 1 |
| Hha I | 25 | Bbv I | 8 | Fok I | 3 | Alw NI | 1 |
| Hin P1I | 25 | Mbo II | 7 | Pfl MI | 3 | Dra III | 1 |
| Hae III | 21 | Ava II | 7 | Hind II | 3 | Afl III | 1 |
| Nla IV | 21 | Mae II | 7 | Dsa I | 3 | Cla I | 1 |
| Nla III | 21 | Sfa NI | 6 | Bsp HI | 3 | Eco 57I* | 1 |
| Hpa II | 20 | Xho II | 6 | Pss I | 3 | Nhe I | 1 |
| Scr FI | 18 | Hgi AI | 6 | Mst I | 3 | Gsu I* | 1 |
| Sso II | 18 | Sfa NI* | 6 | Hgi JII | 2 | Bal I | 1 |
| Fnu DII | 17 | Bbv I* | 6 | Ple I | 2 | Eco RV | 1 |
| Mbo I | 16 | Cfr 10I | 6 | Mbo II* | 2 | Sph I | 1 |
| Dpn I | 16 | Hga I | 6 | Cvi QI | 2 | Xma III | 1 |
| Mnl I* | 15 | Acy I | 5 | Acc I | 2 | Hph I* | 1 |
| Asu I | 12 | Bin I | 5 | Bgl I | 2 | Taq IIB* | 1 |
| Hae II | 11 | Cfr I | 5 | Ple I* | 2 | Eco 57I | 1 |
| Mae III | 11 | Hga I* | 5 | Gsu I | 2 | Kpn I | 1 |
| Hph I | 10 | Mae I | 5 | Ppu MI | 2 | Xba I | 1 |
| Bst NI | 10 | Eco 47III | 5 | TthlllI | 2 | Aha III | 1 |
| Eco RII | 10 | Mnl I | 5 | Hind III | 2 | Nru I | 1 |
| Sec I | 10 | Mme I* | 4 | Nsp HI | 2 | Bam HI | 1 |
| Dde I | 9 | Eco 78I | 4 | Rsa I | 2 | Apa LI | 1 |
| Hinf I | 9 | Nae I | 4 | Sal I | 2 | Asp 718I | 1 |
| Hae I | 9 | Bbe I | 4 | Bbv II | 2 | Eco 31I | 1 |
| Alu I | 9 | Bin I* | 4 | Bsp MI | 2 | Nco I | 1 |
| Hgi CI | 9 | Nar I | 4 | Sty I | 2 | Pst I | 1 |
| Mse I | 9 | Fok I* | 4 | Eco NI | 2 |  |  |
| Taq I | 9 | Dra II | 3 | Xmn I | 2 |  |  |

TABLE 5-continued

RESTRICTION-SITE ANALYSIS

List of non cutting selected enzymes

| | | | | | | |
|---|---|---|---|---|---|---|
| Aat II, | Afl II, | Apa I, | Asu II, | Avr II, | Bbv II*, | Bcl I |
| Bql II, | Bsp MI*, | Bsp MII, | Bss HII, | Bst EII, | Bst XI, | Eco 31I* |
| Eco RI, | Esp I, | Hpa I, | Mlu I, | Mme I, | Nde I, | Not I |
| Nsi I, | Pma CI, | Pvu I, | Pvu II, | Rsr II, | Sac I, | Sac II |
| Sau I, | Sca I, | Sci I, | Sfi I, | Sma I, | Sna BI, | Spe I |
| Spl I, | Ssp I, | Stu I, | Taq IIA, | Taq IIA*, | Tth 111I, | Vsp I |
| Xca I, | Xho I, | Xma I, | | | | |

Total number of selected enzymes which do not cut: 45

Figure 11A:
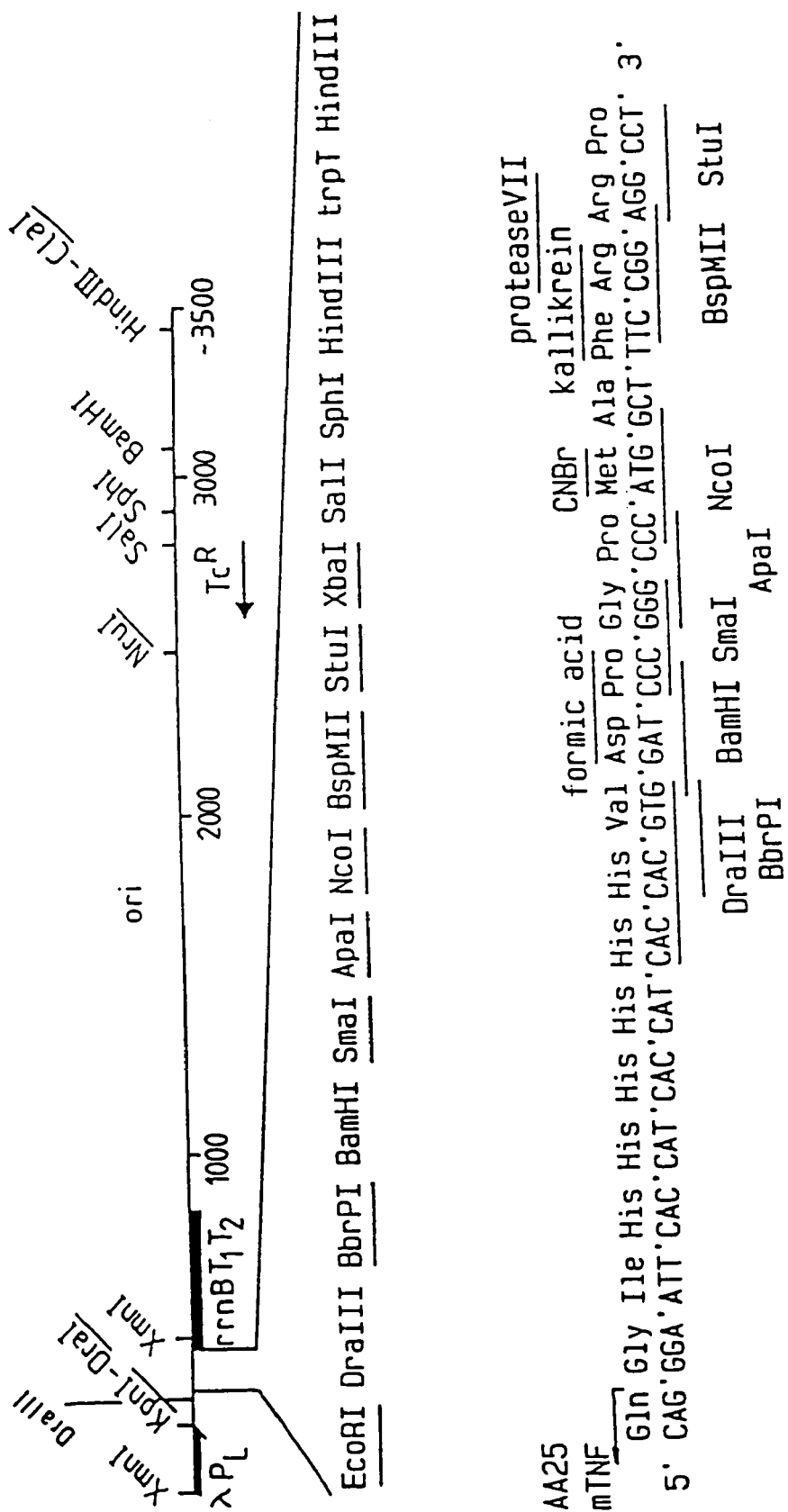

FIG. 11a corresponds to the restriction and genetic map of the pmTNF MPH plasmid used in Example V for the expression of the $P_{32}$ antigen of the invention in *E. coli* and contains SEQ ID NO:51 and SEQ ID NO:52.

FIGS. 11b–11m correspond to the pmTNF-MPH nucleic acid sequence (SEQ ID NO:41).

On this figure, the origin of nucleotide stretches used to construct plasmid pmTNF-MPH is specified hereafter.

| Position | |
|---|---|
| 1–208 | lambda PL containing EcoRI blunt-MboII blunt fragment of pPL(λ) (Pharmacia) |
| 209–436 | synthetic DNA fragment |
| 230–232 | initiation codon (ATG) of mTNF fusion protein |
| 236–307 | sequence encoding AA 2 to 25 of mature mouse TNF |
| 308–384 | multiple cloning site containing |
| 315–332 | His$_6$ encoding sequence at position |
| 385–436 | HindIII fragment containing *E. coli* trp terminator |
| 437–943 | rrnBT$_1$T$_2$ containing HindIII-SspI fragment from pKK223 (Pharmacia) |
| 944–3474 | DraI-EcoRI blunt fragment of pAT$_{153}$ (Bioexcellence) containing the tetracycline resistance gene and the origin of replication. |

Table 6 hereafter corresponds to the complete restriction site analysis of pmTNF-MPH.

TABLE 6

RESTRICTION-SITE ANALYSIS

Done on DNA sequence PMTNFMPH.
Total number of bases is: 3474.
Analysis done on the complete sequence.

List of cuts by enzyme.

| | | | | | | | | | |
|---|---|---|---|---|---|---|---|---|---|
| Acc I | 371 | 2818 | | | | | | | |
| Acy I | 788 | 2264 | 2921 | 3035 | 3056 | | | | |
| Afl II | 387 | | | | | | | | |
| Afl III | 1698 | | | | | | | | |
| Aha III | 224 | | | | | | | | |
| Alu I | 386 | 439 | 1141 | 1398 | 1534 | 1760 | 2382 | 2785 | 3441 | 3456 |
| Alw NI | 1289 | | | | | | | | |
| Apa I | 345 | | | | | | | | |
| Apa LI | 1384 | | | | | | | | |
| Asp 718I | 210 | | | | | | | | |
| Asu I | 341 | 342 | 547 | 676 | 766 | 1988 | 2030 | 2209 | 2333 | 2582 | 267 |
| | 2945 | 3297 | | | | | | | |
| Ava I | 338 | 2043 | | | | | | | |
| Ava II | 547 | 1988 | 2030 | 2333 | 2582 | 2670 | | | |
| Bal I | 2026 | | | | | | | | |
| Bam HI | 334 | 3093 | | | | | | | |
| Bbe I | 2267 | 2924 | 3038 | 3059 | | | | | |
| Bbv I | 1369 | 1788 | 1806 | 1919 | 1922 | 2866 | 3255 | | |
| Bbv I* | 1070 | 1276 | 1279 | 2026 | 2050 | 2683 | | | |
| Bbv II | 1875 | 2738 | | | | | | | |
| Bgl I | 2306 | 2540 | | | | | | | |
| Bin I | 17 | 342 | 956 | 1054 | 1140 | 3101 | | | |
| Bin I* | 329 | 955 | 1052 | 2366 | 3088 | | | | |

TABLE 6-continued

RESTRICTION-SITE ANALYSIS

| Enzyme | | | | | | | | | | | |
|---|---|---|---|---|---|---|---|---|---|---|---|
| Bsp HI | 908 | 978 | 2979 | | | | | | | | |
| Bsp MI | 2414 | | | | | | | | | | |
| Bsp MII | 354 | | | | | | | | | | |
| Bst NI | 215 | 528 | 638 | 806 | 1539 | 1552 | 1673 | 2028 | 2411 | 3340 | |
| Cau II | 6 | 339 | 340 | 736 | 769 | 1321 | 1986 | 2212 | 2936 | 3300 | |
| Cfr 10I | 374 | 2185 | 2539 | 2699 | 3058 | 3067 | 3308 | | | | |
| Cfr I | 2024 | 2529 | 2937 | 3069 | 3173 | | | | | | |
| Cla I | 3446 | | | | | | | | | | |
| Cvi JI | 192 | 265 | 272 | 343 | 350 | 361 | 386 | 400 | 439 | 444 | 47 |
| | 660 | 678 | 767 | 828 | 844 | 1141 | 1170 | 1213 | 1224 | 1289 | 136 |
| | 1393 | 1398 | 1534 | 1632 | 1658 | 1676 | 1687 | 1760 | 1779 | 1979 | 198 |
| | 2026 | 2063 | 2145 | 2189 | 2210 | 2215 | 2353 | 2363 | 2382 | 2423 | 248 |
| | 2488 | 2518 | 2531 | 2552 | 2597 | 2641 | 2785 | 2801 | 2857 | 2875 | 293 |
| | 2947 | 2985 | 2999 | 3071 | 3140 | 3175 | 3298 | 3322 | 3441 | 3456 | |
| Cvi QI | 211 | 3306 | | | | | | | | | |
| Dde I | 135 | 571 | 661 | 717 | 1015 | 1424 | 1888 | | | | |
| Dpn I | 11 | 238 | 336 | 950 | 962 | 1040 | 1048 | 1059 | 1134 | 2010 | 232 |
| | 2342 | 2373 | 2645 | 3004 | 3095 | 3122 | | | | | |
| Dra II | 1988 | 2030 | 2945 | | | | | | | | |
| Dra III | 295 | 331 | | | | | | | | | |
| Dsa I | 345 | 2021 | 2940 | | | | | | | | |
| Eco 31I | 615 | | | | | | | | | | |
| Eco 47III | 1826 | 2695 | 2976 | 3238 | | | | | | | |
| Eco 57I | 216 | | | | | | | | | | |
| Eco 57I* | 1156 | | | | | | | | | | |
| Eco 78I | 2265 | 2922 | 3036 | 3057 | | | | | | | |
| Eco NI | 198 | 2845 | | | | | | | | | |
| Eco RI | 309 | | | | | | | | | | |
| Eco RII | 213 | 526 | 636 | 804 | 1537 | 1550 | 1671 | 2026 | 2409 | 3338 | |
| Eco RV | 3285 | | | | | | | | | | |
| Fnu 4HI | 401 | 417 | 532 | 1084 | 1290 | 1293 | 1358 | 1501 | 1656 | 1774 | 177 |
| | 1795 | 1908 | 1911 | 2040 | 2054 | 2061 | 2064 | 2183 | 2262 | 2307 | 236 |
| | 2447 | 2532 | 2697 | 2748 | 2855 | 2889 | 2892 | 3170 | 3173 | 3244 | |
| Fnu DII | 542 | 1074 | 1655 | 1837 | 1934 | 2056 | 2082 | 2227 | 2237 | 2366 | 243 |
| | 2493 | 2498 | 2525 | 2654 | 2769 | 3125 | | | | | |
| Fok I | 468 | 852 | 3370 | | | | | | | | |
| Fok I* | 816 | 2423 | 2468 | 3322 | | | | | | | |
| Gsu I | 2088 | | | | | | | | | | |
| Gsu I* | 2642 | | | | | | | | | | |
| Hae I | 361 | 828 | 844 | 1224 | 1676 | 1687 | 2026 | 2423 | 2480 | 2552 | |
| Hae II | 594 | 1458 | 1828 | 2267 | 2697 | 2924 | 2978 | 3038 | 3059 | 3240 | |
| Hae III | 343 | 361 | 678 | 767 | 828 | 844 | 1224 | 1658 | 1676 | 1687 | 202 |
| | 2210 | 2423 | 2480 | 2531 | 2552 | 2641 | 2875 | 2939 | 2947 | 3071 | 317 |
| | 3298 | | | | | | | | | | |
| Hga I | 160 | 183 | 796 | 2088 | 2238 | 2829 | | | | | |
| Hga I* | 1008 | 1586 | 2482 | 2514 | 3068 | | | | | | |
| Hgi AI | 141 | 1388 | 2007 | 2298 | 2885 | 3196 | | | | | |
| Hgi CI | 210 | 2179 | 2263 | 2702 | 2920 | 3034 | 3055 | 3349 | 3392 | | |
| Hgi JII | 345 | 2987 | 3001 | | | | | | | | |
| Hha I | 542 | 593 | 1074 | 1183 | 1357 | 1457 | 1524 | 1794 | 1827 | 2017 | 205 |
| | 2115 | 2266 | 2525 | 2656 | 2696 | 2771 | 2923 | 2977 | 3037 | 3058 | 321 |
| | 3239 | 3371 | | | | | | | | | |
| Hin PII | 540 | 591 | 1072 | 1181 | 1355 | 1455 | 1522 | 1792 | 1825 | 2015 | 205 |
| | 2113 | 2264 | 2523 | 2654 | 2694 | 2769 | 2921 | 2975 | 3035 | 3056 | 320 |
| | 3237 | 3369 | | | | | | | | | |
| Hind II | 109 | 372 | 2819 | | | | | | | | |
| Hind III | 384 | 437 | 3439 | | | | | | | | |
| Hinf I | 368 | 1328 | 1724 | 1799 | 1944 | 2165 | 2463 | 2617 | 2837 | | |
| Hpa II | 5 | 339 | 355 | 375 | 735 | 769 | 1130 | 1320 | 1346 | 1493 | 198 |
| | 2186 | 2212 | 2450 | 2540 | 2700 | 2776 | 2936 | 3059 | 3068 | 3083 | 330 |
| | 3309 | | | | | | | | | | |
| Hph I | 96 | 140 | 183 | 716 | 967 | 1953 | 2174 | 3028 | 3073 | 3355 | |
| Hph I* | 8 | 305 | 311 | 317 | | | | | | | |
| Kpn I | 214 | | | | | | | | | | |
| Mae I | 365 | 952 | 1205 | 1981 | 3240 | | | | | | |
| Mae II | 276 | 330 | 751 | 997 | 1900 | 1924 | 2513 | 2569 | | | |
| Mae III | 171 | 257 | 1162 | 1278 | 1341 | 2320 | 2587 | 3255 | 3343 | | |
| Mbo I | 9 | 236 | 334 | 948 | 960 | 1038 | 1046 | 1057 | 1132 | 2008 | 232 |
| | 2340 | 2371 | 2643 | 3002 | 3093 | 3120 | | | | | |
| Mbo II | 209 | 475 | 970 | 1832 | 1880 | 2472 | 2743 | | | | |
| Mbo II* | 1041 | 2997 | | | | | | | | | |
| Mme I* | 1305 | 1489 | 3165 | 3252 | | | | | | | |
| Mnl I | 372 | 1271 | 1595 | 2001 | 2499 | 2683 | | | | | |
| Mnl I* | 210 | 291 | 350 | 764 | 1520 | 1803 | 2169 | 2196 | 2234 | 2295 | 259 |
| | 2864 | 3083 | 3287 | 3347 | | | | | | | |
| Mse I | 181 | 188 | 223 | 388 | 486 | 817 | 994 | 3414 | 3436 | | |
| Mst I | 2016 | 2114 | 3210 | | | | | | | | |

TABLE 6-continued

RESTRICTION-SITE ANALYSIS

| Enzyme | | | | | | | | | | | |
|---|---|---|---|---|---|---|---|---|---|---|---|
| Nae I | 2187 | 2541 | 2701 | 3069 | | | | | | | |
| Nar I | 2264 | 2921 | 3035 | 3056 | | | | | | | |
| Nco I | 345 | | | | | | | | | | |
| Nhe I | 3239 | | | | | | | | | | |
| Nla III | 168 | 232 | 349 | 382 | 565 | 620 | 912 | 982 | 1702 | 1881 | 201 |
| | 2222 | 2279 | 2294 | 2422 | 2539 | 2725 | 2764 | 2910 | 2983 | 3121 | 346 |
| Nla IV | 212 | 336 | 343 | 549 | 1631 | 1670 | 1989 | 2032 | 2146 | 2181 | 221 |
| | 2265 | 2583 | 2704 | 2922 | 2946 | 3036 | 3057 | 3095 | 3141 | 3351 | 339 |
| Nru I | 2498 | | | | | | | | | | |
| Nsp BII | 412 | 1115 | 1360 | 2331 | | | | | | | |
| Nsp HI | 382 | 1702 | 2910 | | | | | | | | |
| Pfl MI | 295 | 2105 | 2154 | | | | | | | | |
| Ple I | 376 | 1807 | | | | | | | | | |
| Ple I* | 1322 | 2831 | | | | | | | | | |
| Pma CI | 331 | | | | | | | | | | |
| Ppu MI | 1988 | 2030 | | | | | | | | | |
| Pss I | 1991 | 2033 | 2948 | | | | | | | | |
| Rsa I | 212 | 3307 | | | | | | | | | |
| Sal I | 370 | 2817 | | | | | | | | | |
| Scr FI | 6 | 215 | 339 | 340 | 528 | 638 | 736 | 769 | 806 | 1321 | 153 |
| | 1552 | 1673 | 1986 | 2028 | 2212 | 2411 | 2936 | 3300 | 3340 | | |
| Sdu I | 141 | 345 | 1388 | 2007 | 2298 | 2885 | 2987 | 3001 | 3196 | | |
| Sec I | 5 | 338 | 345 | 1538 | 2021 | 2099 | 2301 | 2934 | 2940 | 3339 | 335 |
| Sfa NI | 650 | 818 | 2445 | 2820 | 3231 | 3344 | | | | | |
| Sfa NI* | 420 | 1601 | 2038 | 2433 | 3054 | 3066 | 3255 | | | | |
| Sma I | 340 | | | | | | | | | | |
| Sph I | 382 | 2910 | | | | | | | | | |
| Sso II | 4 | 213 | 337 | 338 | 526 | 636 | 734 | 767 | 804 | 1319 | 153 |
| | 1550 | 1671 | 1984 | 2026 | 2210 | 2409 | 2934 | 3298 | 3338 | | |
| Stu I | 361 | | | | | | | | | | |
| Sty I | 345 | 2099 | | | | | | | | | |
| Taq I | 254 | 371 | 666 | 1600 | 2202 | 2343 | 2818 | 3131 | 3446 | | |
| Taq IIB | 1802 | | | | | | | | | | |
| Taq IIB* | 2804 | | | | | | | | | | |
| TthIIII | 40 | 1107 | | | | | | | | | |
| TthIIII* | 686 | 1075 | 1114 | | | | | | | | |
| Xba I | 364 | | | | | | | | | | |
| Xho II | 9 | 334 | 948 | 960 | 1046 | 1057 | 3093 | | | | |
| Xma I | 338 | | | | | | | | | | |
| Xma III | 2529 | | | | | | | | | | |
| Xmn I | 467 | | | | | | | | | | |

Total number of cuts is: 743.

| | | | | | | |
|---|---|---|---|---|---|---|
| Aat II, | Asu II, | Avr II, | Bbv II*, | Bcl I, | Bgl II, | Bsp MI* |
| Bss HII, | Bst EII, | Bst XI, | Eco 3lI*, | Esp I, | Hpa I, | Mlu I |
| Mme I, | Nde I, | Not I, | Nsi I, | Pst I, | Pvu I, | Pvu I |
| Rsr II, | Sac I, | Sac II, | Sau I, | Sca I, | Sci I, | Sfi I |
| Sna BI, | Spe I, | Spl I, | Ssp I, | Taq IIA, | Taq IIA*, | Tth IIII |
| Vsp I, | Xca I, | Xho I | | | | |

Total number of selected enzymes which do not cut: 38

Figure 12A:

FIG. 12a corresponds to the restriction and genetic map of the plasmid pIG2 used to make the intermediary construct pIG2 Mt32 as described in Example IV for the subcloning of the $P_{32}$ antigen in plasmid pIGRI and contains SEQ ID NO:53.

FIGS. 12b–12l correspond to the pIG2 nucleic acid sequence (SEQ ID NO:42).

On this figure, the origin of nucleotide stretches used to construct plasmid pIG2 is specified hereafter.

| Position | |
|---|---|
| 3300–206 | lambda PL containing EcoRI-MboII blunt fragment of pPL(λ) (Pharmacia) |

-continued

| Position | |
|---|---|
| 207–266 | synthetic sequence containing multiple cloning site and ribosone binding site of which the ATG initiation codon is located at position 232–234 |
| 267–772 | rrnBT$_1$T$_2$ containing HindIII-SspI fragment from pKK223 (Pharmacia) |
| 773–3300 | tetracycline resistance gene and origin of replication containing EcoRI-DraI fragment of pAT 153 (Bioexcellence) |

Table 7 corresponds to the complete restriction site analysis of pIG2.

TABLE 7

RESTRICTION-SITE ANALYSIS

Done on DNA sequence pIG2
Total number of bases is: 3301.
Analysis done on the complete sequence.

List of cuts by enzyme.

| Enzyme | Positions |
|---|---|
| Acc I | 252 2647 |
| Acy I | 617 2093 2750 2664 2885 |
| Afl III | 1527 |
| Aha III | 222 |
| Alu I | 268 970 1227 1363 1589 2211 2614 3270 3285 |
| Alw NI | 1118 |
| Apa LI | 1213 |
| Asp 718I | 208 |
| Asu I | 376 505 595 1817 1859 2038 2162 2411 2499 2774 312 |
| Ava I | 1872 |
| Ava II | 376 1817 1859 2162 2411 2499 |
| Bal I | 1855 |
| Bam HI | 239 2922 |
| Bbe I | 2096 2753 2867 2888 |
| Bbv I | 271 1198 1617 1635 1748 1751 2695 3084 |
| Bbv I* | 899 1105 1108 1855 1879 2512 |
| Bbv II | 1704 2567 |
| Bgl I | 2135 2369 |
| Bin I | 15 247 785 883 969 2930 |
| Bin I* | 234 784 881 2195 2917 |
| Bsp HI | 737 807 2808 |
| Bsp MI | 264 2243 |
| Bst NI | 213 357 467 635 1366 1381 1502 1857 2240 3169 |
| Cau II | 4 565 598 1150 1815 2641 2765 3129 |
| Cfr 10I | 2014 2368 2528 2887 2896 3137 |
| Cfr I | 1853 2358 2766 2898 3002 |
| Cla I | 3275 |
| Cvi JI | 190 262 268 273 303 489 507 596 657 673 97 |
| | 999 1042 1053 1118 1197 1222 1227 1363 1461 1487 150 |
| | 1516 1589 1608 1808 1813 1855 1892 1974 2018 2039 204 |
| | 2182 2192 2211 2252 2309 2317 2347 2360 2381 2426 247 |
| | 2614 2630 2686 2704 2768 2776 2814 2828 2900 2969 300 |
| | 3127 3151 3270 3285 |
| Cvi QI | 209 3135 |
| Dde I | 133 400 490 546 844 1253 1717 |
| Dpn I | 9 241 779 791 869 877 888 963 1839 2156 217 |
| | 2202 2474 2833 2924 2951 |
| Dra II | 1817 1859 2774 |
| Dsa I | 230 1850 2769 |
| Eco 31I | 444 |
| Eco 47III | 1655 2524 2805 3067 |
| Eco 57I | 214 |
| Eco 57I* | 985 |
| Eco 78I | 2094 2751 2865 2886 |
| Eco NI | 196 2674 |
| Eco RII | 211 355 465 633 1366 1379 1500 1855 2238 3167 |
| Eco RV | 3114 |
| Fnu 4HI | 260 361 913 1119 1122 1187 1330 1485 1603 1606 162 |
| | 1737 1740 1869 1883 1890 1893 2012 2091 2136 2193 227 |
| | 2361 2526 2577 2684 2718 2721 2999 3002 3073 |
| Fnu DII | 371 903 1484 1666 1763 1885 1911 2056 2066 2195 226 |
| | 2322 2327 2354 2483 2598 2954 |
| Fok I | 297 681 3199 |
| Fok I* | 645 2252 2297 3151 |
| Gsu I | 1917 |
| Gsu I* | 2471 |
| Hae I | 657 673 1053 1505 1516 1855 2252 2309 2381 |
| Hae II | 423 1287 1657 2096 2526 2753 2807 2867 2888 3069 |
| Hae III | 507 596 657 673 1053 1487 1505 1516 1855 2039 225 |
| | 2309 2360 2381 2470 2704 2768 2776 2900 3004 3127 |
| Hga I | 158 181 625 1917 2067 2658 |
| Hga I* | 837 1415 2311 2343 2897 |
| Hgi AI | 139 1217 1836 2127 2714 3025 |
| Hgi CI | 208 2008 2092 2531 2749 2863 2884 3178 3221 |
| Hgi JII | 2816 2830 |
| Hha I | 371 422 903 1012 1186 1286 1353 1623 1656 1846 188 |
| | 1944 2095 2354 2485 2525 2600 2752 2806 2866 2887 304 |
| | 3068 3200 |
| Hin PII | 369 420 901 1010 1184 1284 1351 1621 1654 1844 188 |
| | 1942 2093 2352 2483 2523 2598 2750 2804 2864 2885 303 |
| | 3066 3198 |

TABLE 7-continued

RESTRICTION-SITE ANALYSIS

| Enzyme | | | | | | | | | | |
|---|---|---|---|---|---|---|---|---|---|---|
| Hind II | 107 | 253 | 2648 | | | | | | | |
| Hind III | 266 | 3268 | | | | | | | | |
| Hinf I | 249 | 1157 | 1553 | 1628 | 1773 | 1994 | 2292 | 2446 | 2666 | |
| Hpa II | 3 | 564 | 598 | 959 | 1149 | 1175 | 1322 | 1814 | 2015 | 2041 | 227 |
| | 2369 | 2529 | 2605 | 2765 | 2888 | 2897 | 2912 | 3129 | 3138 | |
| Hph I | 94 | 138 | 181 | 545 | 796 | 1782 | 2003 | 2857 | 2902 | 3184 |
| Hph I* | 6 | | | | | | | | | |
| Kpn I | 212 | | | | | | | | | |
| Mae I | 246 | 781 | 1034 | 1810 | 3069 | | | | | |
| Mae II | 580 | 826 | 1729 | 1753 | 2342 | 2398 | | | | |
| Mae III | 169 | 991 | 1107 | 1170 | 2149 | 2416 | 3084 | 3172 | | |
| Mbo I | 7 | 239 | 777 | 789 | 867 | 875 | 886 | 961 | 1837 | 2154 | 216 |
| | 2200 | 2472 | 2831 | 2922 | 2949 | | | | | |
| Mbo II | 207 | 304 | 799 | 1661 | 1709 | 2301 | 2572 | | | |
| Mbo II* | 870 | 2826 | | | | | | | | |
| Mme I* | 1134 | 1318 | 2994 | 3081 | | | | | | |
| Mnl I | 253 | 1100 | 1424 | 1830 | 2328 | 2512 | | | | |
| Mnl I* | 208 | 593 | 1349 | 1632 | 1998 | 2025 | 2063 | 2124 | 2426 | 2693 | 291 |
| | 3116 | 3176 | | | | | | | | |
| Mse I | 179 | 186 | 221 | 315 | 646 | 823 | 3243 | 3265 | | |
| Mst I | 1845 | 1943 | 3039 | | | | | | | |
| Nae I | 2016 | 2370 | 2530 | 2898 | | | | | | |
| Nar I | 2093 | 2750 | 2864 | 2885 | | | | | | |
| Nco I | 230 | | | | | | | | | |
| Nhe I | 3068 | | | | | | | | | |
| Nla III | 166 | 234 | 394 | 449 | 741 | 811 | 1531 | 1710 | 1844 | 2051 | 210 |
| | 2123 | 2251 | 2368 | 2554 | 2593 | 2739 | 2812 | 2950 | 3297 | |
| Nla IV | 210 | 241 | 378 | 1460 | 1499 | 1818 | 1861 | 1975 | 2010 | 2045 | 209 |
| | 2412 | 2533 | 2751 | 2775 | 2865 | 2886 | 2924 | 2970 | 3180 | 3223 |
| Nru I | 2327 | | | | | | | | | |
| Nsp BII | 944 | 1189 | 2160 | | | | | | | |
| Nsp HI | 1531 | 2739 | | | | | | | | |
| Pfl MI | 1934 | 1983 | | | | | | | | |
| Ple I | 257 | 1636 | | | | | | | | |
| Ple I* | 1151 | 2660 | | | | | | | | |
| Ppu MI | 1817 | 1859 | | | | | | | | |
| Pss I | 1820 | 1862 | 2777 | | | | | | | |
| Pst I | 261 | | | | | | | | | |
| Rsa I | 210 | 3136 | | | | | | | | |
| Sal I | 251 | 2646 | | | | | | | | |
| Scr FI | 4 | 213 | 357 | 467 | 565 | 598 | 635 | 1150 | 1368 | 1381 | 150 |
| | 1815 | 1857 | 2041 | 2240 | 2765 | 3129 | 3169 | | | |
| Sdu I | 139 | 1217 | 1836 | 2127 | 2714 | 2816 | 2830 | 3025 | | |
| Sec I | 3 | 230 | 1367 | 1850 | 1928 | 2130 | 2763 | 2769 | 3168 | 3182 |
| Sfa NI | 479 | 647 | 2274 | 2649 | 3060 | 3173 | | | | |
| Sfa NI* | 1430 | 1867 | 2262 | 2883 | 2895 | 3084 | | | | |
| Sph I | 2739 | | | | | | | | | |
| Sso II | 2 | 211 | 355 | 465 | 563 | 596 | 633 | 1148 | 1366 | 1379 | 150 |
| | 1813 | 1855 | 2039 | 2238 | 2763 | 3127 | 3167 | | | |
| Ssp I | 226 | | | | | | | | | |
| Sty I | 230 | 1928 | | | | | | | | |
| Taq I | 252 | 495 | 1429 | 2031 | 2172 | 2647 | 2960 | 3275 | | |
| Taq IIB | 1631 | | | | | | | | | |
| Taq IIB* | 2633 | | | | | | | | | |
| TthlllII | 38 | 936 | | | | | | | | |
| TthlllII* | 515 | 904 | 943 | | | | | | | |
| Xba I | 245 | | | | | | | | | |
| Xho II | 7 | 239 | 777 | 789 | 875 | 886 | 2922 | | | |
| Xma III | 2358 | | | | | | | | | |
| Xmn I | 296 | | | | | | | | | |
| EcoRI | 3300 | | | | | | | | | |

Total number of cuts is: 689.

| List of non cutting selected enzymes. | | | | | | | |
|---|---|---|---|---|---|---|---|
| Aat II, | Afl II, | Apa I, | Asu II, | Avr II, | Bbv II*, | Bcl I | |
| Bgl II, | Bsp MI*, | Bsp MII, | Bss HII, | Bst EII, | Bst XI, | Dra III | |
| Eco 31I*, | Esp I, | Hpa I, | Mlu I, | Mme I, | Nde I, | Not I | |
| Nsi I, | Pma CI, | Pvu I, | Pvu II, | Rsr II, | Sac I, | Sac II | |
| Sau I, | Sca I, | Sci I, | Sfi I, | Sma I, | Sna BI, | Spe I | |
| Spl I, | Stu I, | Taq IIA, | Taq IIA*, | Tth lllI, | Vsp I, | Xca I | |
| Xho I, | Xma I | | | | | | |

Total number of selected enzymes which do not cut: 44

FIG. 13 corresponds to the amino acid sequence of the total fusion protein mTNF-His$_6$-P$_{32}$ (SEQ ID NO:43).

On this figure:
the continuous underlined sequence (_____) represents the mTNF sequence (first 25 amino acids),
the dotted underlined sequence (- - - - -) represents the polylinker sequence,
the double underlined sequence ═══)represents the extra amino acids created at cloning site, and
the amino acid marked with nothing is the antigen sequence starting from the amino acid at position 4 of FIG. 5.

Figure 14A:
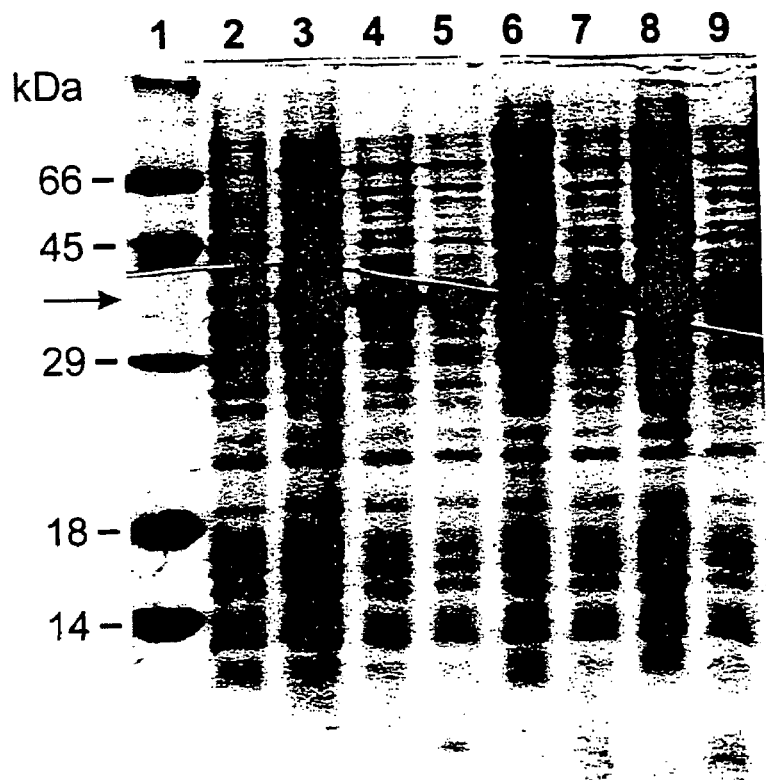
Figure 14B:
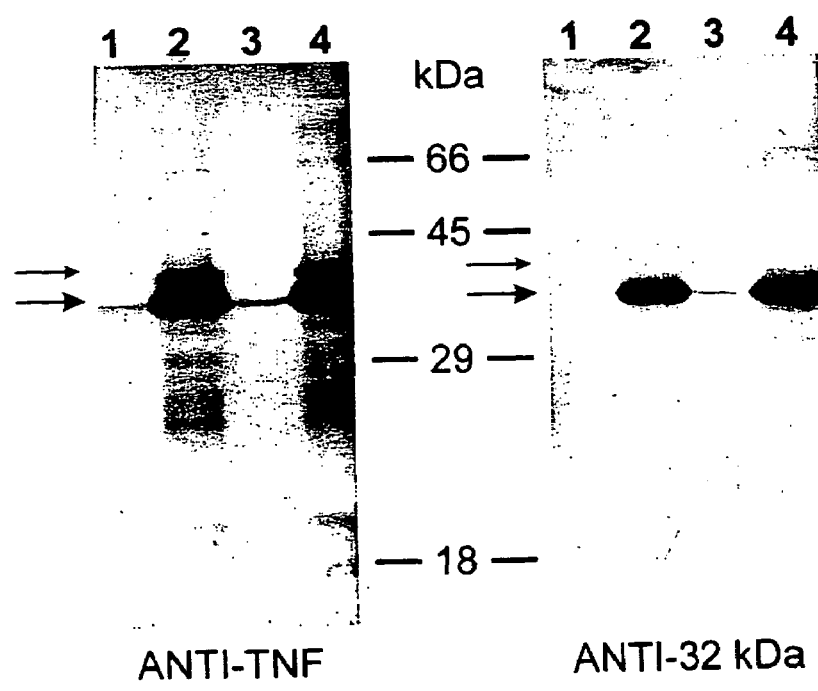

FIGS. 14a and 14b correspond to the expression of the mTNF-His$_6$-P$_{32}$ fusion protein in K12ΔH, given in Example VI, with FIG. 14a representing the Coomassie Brilliant Blue stained SDS-PAGE and 14b representing immunoblots of the gel with anti-32-kDa and anti-mTNF-antibody.

On FIG. 14a, the lanes correspond to the following:

| Lanes | | | |
|---|---|---|---|
| 1. | protein molecular weight markers | | |
| 2. | pmTNF-MPH-Mt32 | 28° C. | 1 h induction |
| 3. | " | 42° C. | " |
| 4. | " | 42° C. | 2 h induction |
| 5. | " | 42° C. | 3 h induction |
| 6. | " | 28° C. | 4 h induction |
| 7. | " | 42° C. | 4 h induction |
| 8. | " | 28° C. | 5 h induction |
| 9. | " | 42° C. | 5 h induction |

On FIG. 14b, the lanes correspond to the following:

| Lanes | | | |
|---|---|---|---|
| 1. | pmTNF-MPH-Mt32 | 28° C. | 1 h induction |
| 2. | " | 42° C. | 1 h induction |
| 3. | " | 28° C. | 4 h induction |
| 4. | " | 42° C. | 4 h induction |

Figure 15:
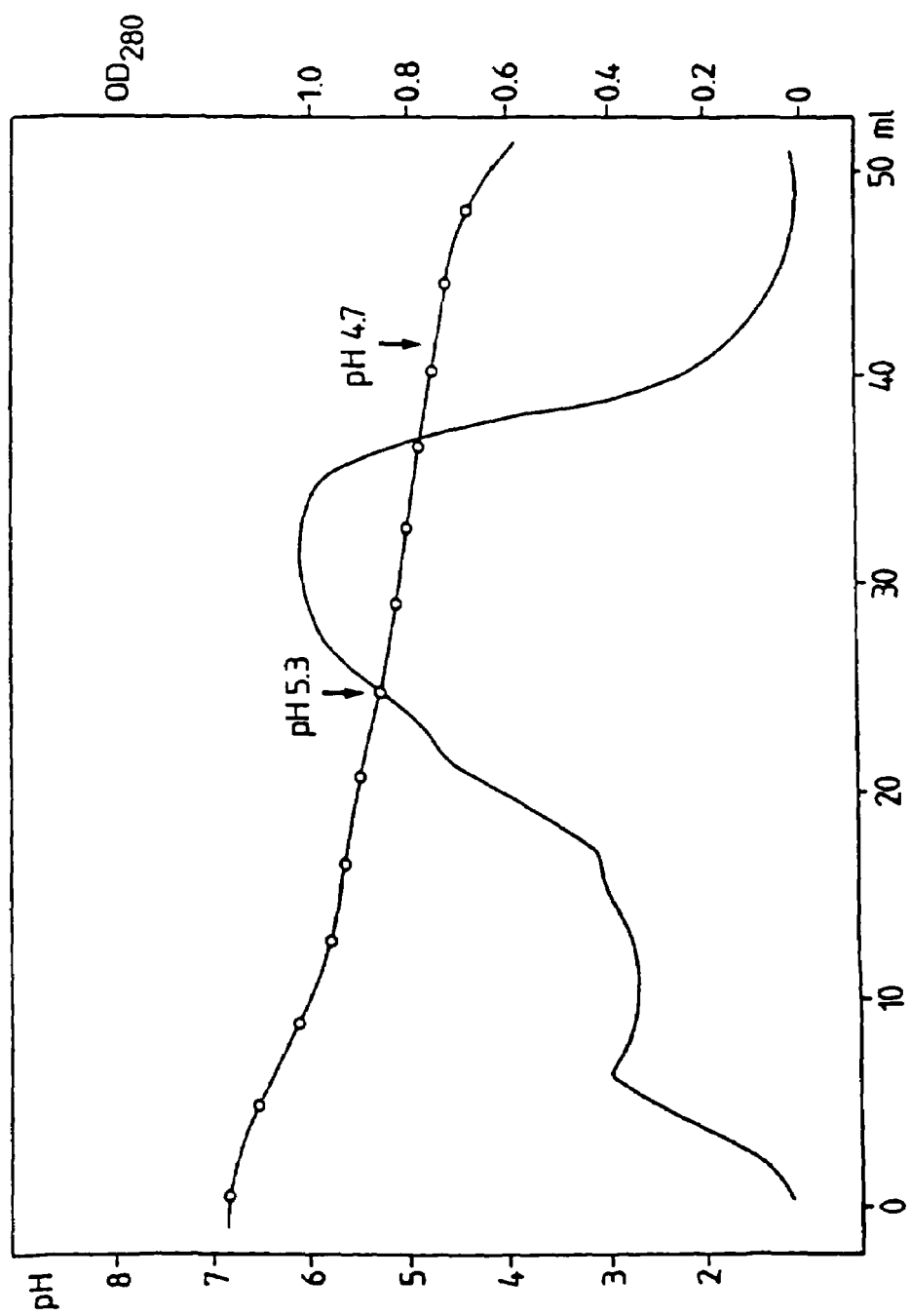

FIG. 15 corresponds to the IMAC elution profile of the recombinant antigen with decreasing pH as presented in Example VII.

Figure 16:
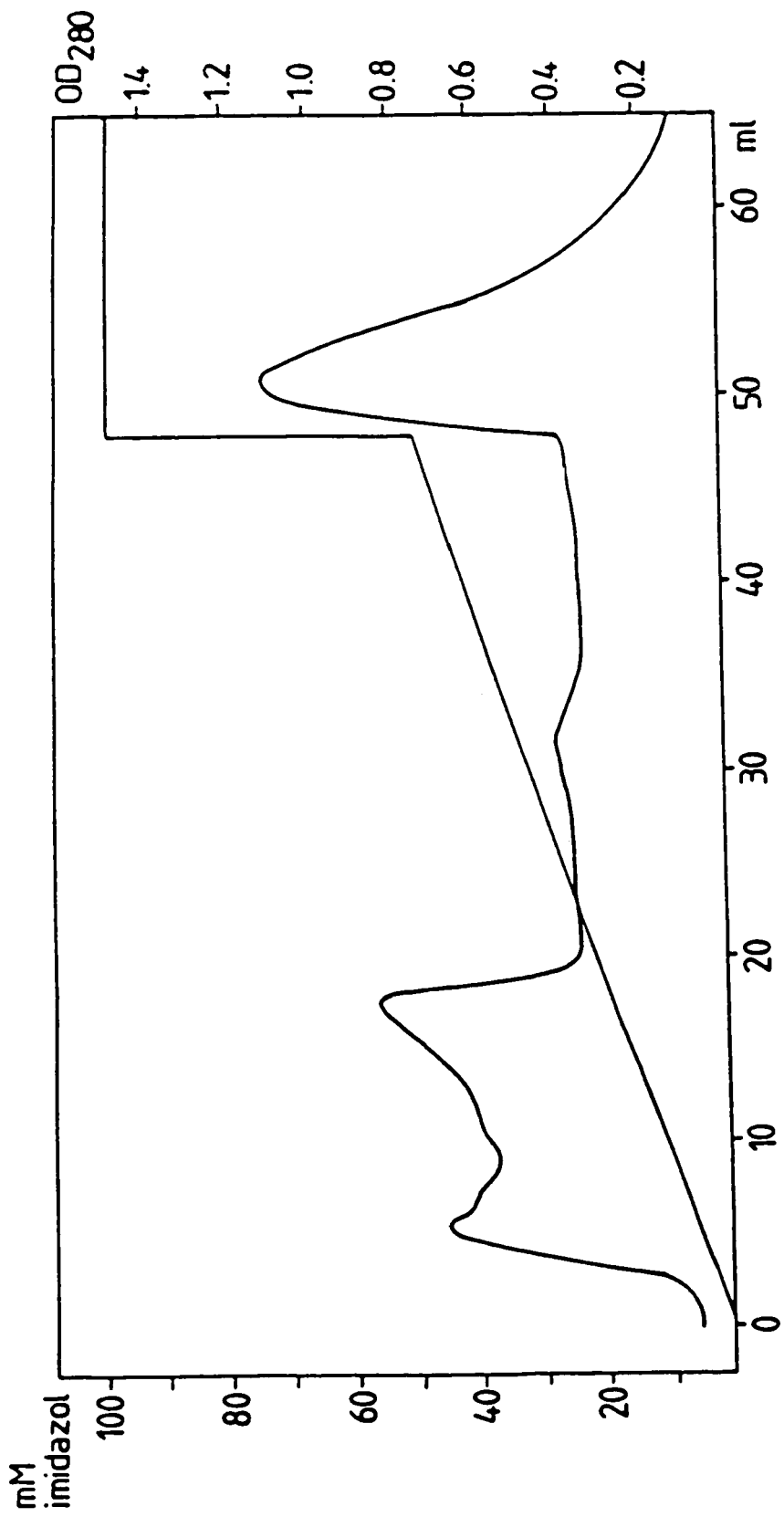

FIG. 16 corresponds to the IMAC elution profile of the recombinant antigen with increasing imidazole concentrations as presented in Example VII.

Figure 17:
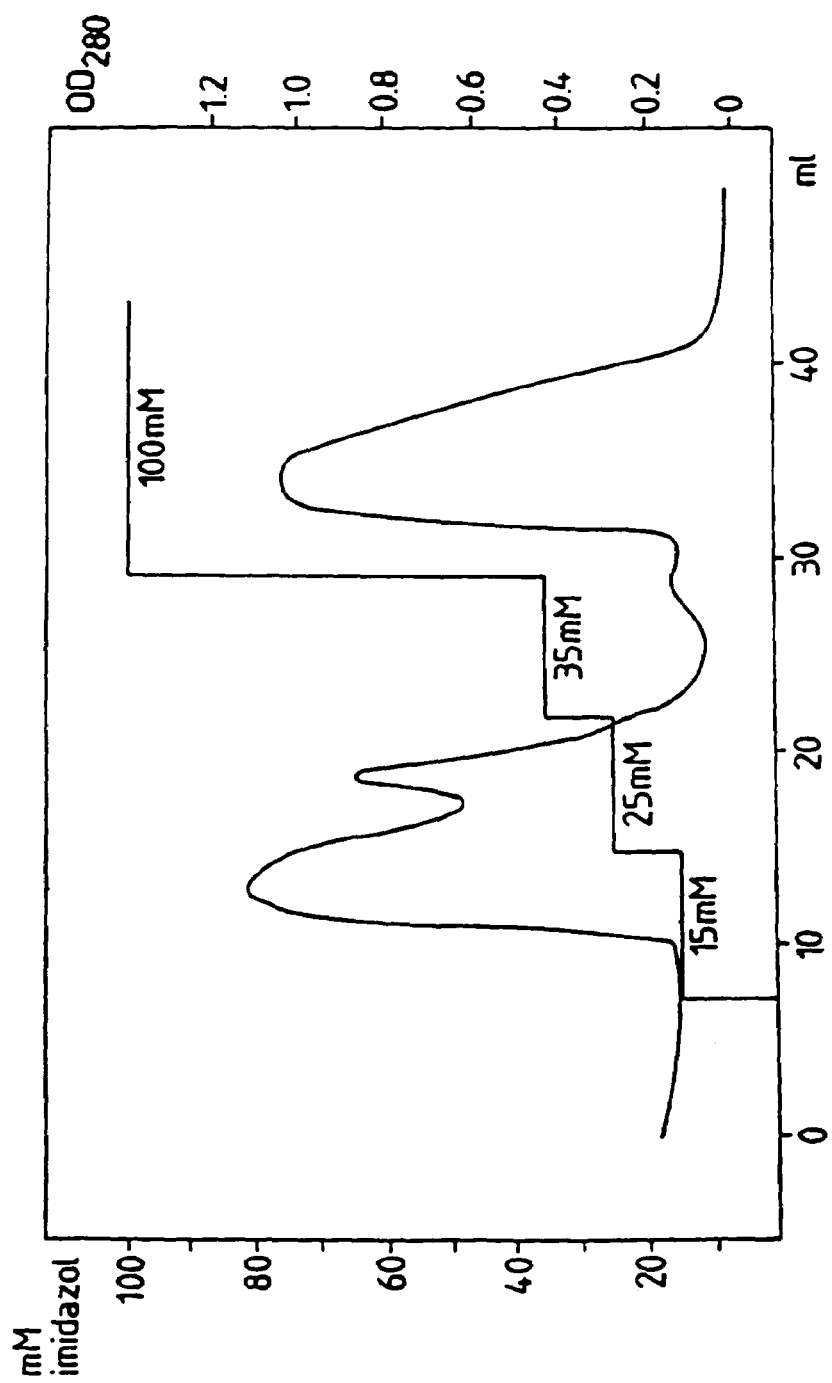

FIG. 17 corresponds to the IMAC elution profile of the recombinant antigen with a step gradient of increasing imidazole concentrations as presented in Example VII.

DESCRIPTION OF THE PREFERRED EMBODIMENTS

EXAMPLE I

Material and Methods

Screening of the λqt11 M. tuberculosis Recombinant DNA Library with Anti-32-kDa Antiserum A λgt11 recombinant library constructed from genomic DNA of M. tuberculosis (Erdman strain), was obtained from R. Young (35). Screening was performed as described (14, 35) with some modifications hereafter mentioned. λgt11 infected E. coli Y1090 (10$^5$ pfu per 150 mm plate) were seeded on NZYM plates (Gibco) (16) and incubated at 42° C. for 24 hrs. To induce expression of the β-galactosidase-fusion proteins the plates were overlaid with isopropyl β-D-thiogalactoside (IPTG)-saturated filters (Hybond C extra, Amersham), and incubated for 2 hrs at 37° C. Screening was done with a polyclonal rabbit anti-32-kDa antiserum. Said polyclonal antiserum rabbit anti-32-kDa antiserum was obtained by raising antiserum against the P$_{32}$ M. bovis BCG (strain 1173P2—Institut Pasteur Paris) as follows: 400 μg (purified P$_{32}$ protein of M. bovis BCG) per ml physiological saline were mixed with one volume of incomplete Freund's adjuvant. The material was homogenized and injected intradermally in 50 μl doses, delivered at 10 sites in the back of the rabbits, at 0, 4, 7 and 8 weeks (adjuvant was replaced by the diluent for the last injection). One week later, the rabbits were bled and the sera tested for antibody level before being distributed in aliquots and stored at −80° C.

The polyclonal rabbit anti-32-kDa antiserum was pre-absorbed on E. coli lysate (14) and used at a final dilution of 1:300. A secondary alkaline-phosphatase anti-rabbit IgG conjugate (Promega), diluted at 1:5000 was used to detect the β-galactosidase fusion proteins. For color development nitro blue tetrazolium (NBT) and 5-bromo-4-chloro-3-indolyl phosphate (BCIP) were used. Reactive areas on the filter turned deep purple within 30 min. Usually three consecutive purification steps were performed to obtain pure clones. IPTG, BCIP and NBT were from Promega corp. (Madison Wis.).

Plaque Screening by Hybridization for Obtaining the Secondary Clones BY1, By2 and By5 Hereafter Defined The procedure used was as described by Maniatis et al. (14).

Preparation of Crude Lysates from λgt11 Recombinant Lysogens

Colonies of E. coli Y1089 were lysogenized with appropriate λgt11 recombinants as described by Hyunh et al. (14). Single colonies of lysogenized E. coli Y1089 were inoculated into LB medium and grown to an optical density of 0.5 at 600 nm at 30° C. After a heat shock at 45° C. for 20 min., the production of β-galactosidase-fusion protein was induced by the addition of IPTG to a final concentration of 10 mM. Incubation was continued for 60 min. at 37° C. and cells were quickly harvested by centrifugation. Cells were concentrated 50 times in buffer (10 mM Tris pH 8.0, 2 mM EDTA) and rapidly frozen into liquid nitrogen. The samples were lysed by thawing and treated with 100 μg/ml DNase I in EcoRI restriction buffer, for 5–10 minutes at 37° C.

Immunoblotting (Western Blotting) Analysis:

After SDS-PAGE electrophoresis, recombinant lysogen proteins were blotted onto nitrocellulose membranes (Hybond C, Amersham) as described by Towbin et al. (29). The expression of mycobacterial antigens, fused to β-galactosidase in E. coli Y1089 was visualized by the binding of a polyclonal rabbit anti-32-kDa antiserum (1:1000) obtained as described in the above paragraph "Screening of the λgt11 M. tuberculosis recombinant DNA library with anti-32-kDa antiserum" and using a monoclonal anti-β-galactosidase antibody (Promega). A secondary alkaline-phosphatase anti-rabbit IgG conjugate (Promega) diluted at 1:5000, was used to detect the fusion proteins.

The use of these various antibodies enables to detect the β-galactosidase fusion protein. This reaction is due to the M. tuberculosis protein because of the fact that non fused-β-galactosidase is also present on the same gel and is not recognized by the serum from tuberculous patients.

In order to identify selective recognition of recombinant fusion proteins by human tuberculous sera, nitrocellulose sheets were incubated overnight with these sera (1:50) (after blocking aspecific protein binding sites). The human tuberculous sera were selected for their reactivity (high or low) against the purified 32-kDa antigen of *M. bovis* BCG tested in a Dot blot assay as previously described (31). Reactive areas on the nitrocellulose sheets were revealed by incubation with peroxidase conjugated goat anti-human IgG antibody (Dakopatts, Copenhagen, Denmark) (1:200) for 4 hrs and after repeated washings color reaction was developed by adding peroxidase substrate (α-chloronaphtol) (Bio-Rad) in the presence of peroxidase and hydrogen peroxide.

Recombinant DNA Analysis

Initial identification of *M. tuberculosis* DNA inserts in purified λgt11 clones was performed by EcoRI restriction. After digestion, the excised inserts were run on agarose gels and submitted to Southern hybridization. Probes were labeled with α$^{32}$P-dCTP by random priming (10). Other restriction sites were located by single and double digestions of recombinant λgt11 phage DNA or their subcloned EcoRI fragments by HindIII, PstI, KpnI, AccI and SphI.

Sequencing

Sequence analysis was done by the primer extension dideoxy termination method of Sanger et al. (25) after subcloning of specific fragments in Bluescribe-M13 (6) or in mp10 and mp11 M13 vectors (Methods in Enzymology, vol. 101, 1983, p. 20–89, Joachim Messing, New M13 vectors for cloning, Academic Press). Sequence analysis was greatly hampered by the high GC content of the *M. tuberculosis* DNA (65%). Sequencing reactions were therefore performed with several DNA polymerases: T7 DNA polymerase ("Sequenase" USB), Klenow fragment of DNA polymerase I (Amersham) and in some cases with AMV reverse transcriptase (Super RT, Anglian Biotechnology Ltd.) and sometimes with dITP instead of dGTP. Several oligodeoxynucleotides were synthesized and used to focus ambiguous regions of the sequence. The sequencing strategy is summarized in FIG. 2. In order to trace possible artefactual frameshifts in some ambiguous regions, a special program was used to define the most probable open reading frame in sequences containing a high proportion of GC (3). Several regions particularly prone to sequencing artefacts were confirmed or corrected by chemical sequencing (18). For this purpose, fragments were subcloned in the chemical sequencing vector pGV462 (21) and analysed as described previously. Selected restriction fragments of about 250–350 bp were isolated, made blunt-ended by treatment with either Klenow polymerase or Mung bean nuclease, and subcloned in the SmaI or HincII site of pGV462. Both strands of the inserted DNA were sequenced by single-end labeling at Tth 111I or BstEII (32) and a modified chemical degradation strategy (33).

Routine computer aided analysis of the nucleic acid and deduced amino acid sequences were performed with the LGBC program from Bellon (2). Homology searches used the FASTA programs from Pearson and Lipman (23) and the Protein Identification Resource (PIR) from the National Biomedical Research Fundation—Washington (NBRF) (NBRF/PIR data bank), release 16 (March 1988).

Results

Screening of the λgt11M, *M. tuberculosis* Recombinant DNA Library with Polyclonal Anti-32-kDa Antiserum:

Ten filters representing 1.5×10$^6$ plaques were probed with a polyclonal rabbit anti-32-kDa antiserum (8). Following purification, six independent positive clones were obtained.

Analysis of Recombinant Clones

Figure 1A:
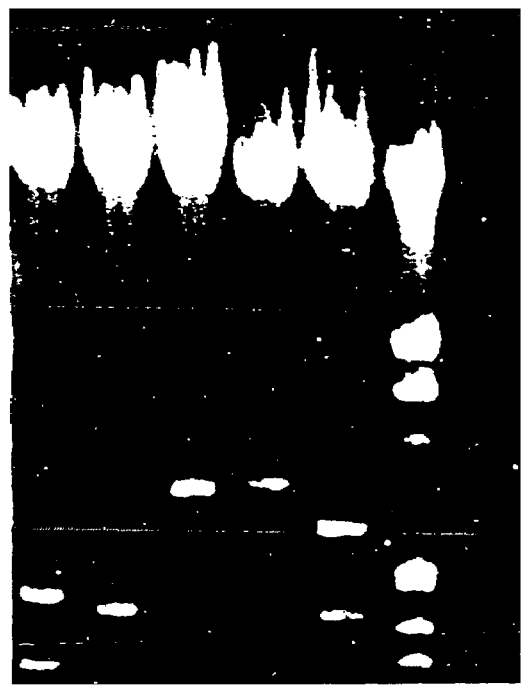
FIGS. 1(A) and 1(B) correspond to the identification of six purified λgt11 *M. tuberculosis* recombinant clones.

EcoRI restriction analysis of these 6 purified λgt11 recombinant clones DNA, (FIG. 1A) revealed 4 different types of insert. Clone 15 had an insert with a total length of 3.8 kb with two additional internal EcoRI sites resulting in three DNA fragments of 1.8 kb, 1.5 kb and 0.5 kb. The DNA Insert of clone 16 was 1.7 kb long. Clones 17 and 19 had a DNA insert of almost identical length being 2.7 kb and 2.8 kb respectively.

Figure 1B:

Finally, clone 23 (not shown) and clone 24 both contained an insert of 4 kb with one additional EcoRI restriction site giving two fragments of 2.3 kb and 1.7 kb. Southern analysis (data not shown) showed that the DNA inserts of clones 15, 16, 19 and the small fragment (1.7 kb) of clone 24 only hybridized with themselves whereas clone 17 (2.7 kb) hybridized with itself but also equally well with the 2.3 kb DNA fragment of clone 24. Clones 15, 16 and 19 are thus distinct and unrelated to the 17, 23, 24 group. This interpretation was further confirmed by analysis of crude lysates of *E. coli* Y1089 lysogenized with the appropriate λgt11 recombinants and induced with IPTG. Western blot analysis (FIG. 1B), showed no fusion protein, either mature or incomplete, reactive with the polyclonal anti-32-kDa antiserum in cells expressing clones 15, 16 and 19. Clones 15, 16 and 19, were thus considered as false positives and were not further studied. On the contrary, cells lysogenized with clone 23 and 24 produced an immunoreactive fusion protein containing about 10 kDa of the 32-kDa protein. Clone 17 finally expressed a fusion protein of which the foreign polypeptide part is about 25 kDa long. The restriction endonuclease maps of the 2.3 kb insert of clone 24 and of the 2.7 kb fragment of clone 17 (FIG. 2) allowed us to align and orient the two inserts suggesting that the latter corresponds to a ±0.5 kb 5' extension of the first.

As clone 17 was incomplete, the same λgt11 recombinant *M. tuberculosis* DNA library was screened by hybridization with a 120 bp EcoRI-KpnI restriction fragment corresponding to the very 5' end of the DNA insert of clone 17 (previously subcloned in a Blue Scribe vector commercialized by Vector cloning Systems (Stratagene Cloning System) (FIG. 2). Three 5'-extended clones By1, By2 and By5 were isolated, analyzed by restriction and aligned. The largest insert, By5 contained the information for the entire coding region (see below) flanked by 3.1 kb upstream and 1.1 kb downstream (FIG. 2).

DNA Sequencing

The 1358 base pairs nucleotide sequence derived from the various λgt11 overlapping clones is represented in FIG. 3a and FIG. 3b. The DNA sequence contains a 1059 base pair open reading frame starting at position 183 and ending with a TAG codon at position 1242. It occurs that the NH$_2$-terminal amino-acid sequence, (phe-ser-arg-pro-gly-leu-pro-val-glu-tyr-leu-gln-val-pro-ser-pro-ser-met-gly-arg-asp-ile-lys-val-gln-phe-gln-ser-gly-gly-ala-asn; SEQ ID NO:33) which can be located within this open reading frame from the nucleotide sequence beginning with a TTT codon at position 360 corresponds to the same NH$_2$-terminal amino acid sequence of the MPB 59 antigen except for the amino acids at position 20, 21, 31, which are respectively gly, cys and asn in the MPB 59 (34). Therefore, the DNA region upstream of this sequence is expected to encode a signal peptide required for the secretion of a protein of 32-kDa. The mature protein thus presumably consists of 295 amino acid residues from the N-terminal Phe (TTT codon) to the C-terminal Ala (GCC codon) (FIG. 5).

Six ATG codons were found to precede the TTT at position 360 in the same reading frame. Usage of any of these ATGs in the same reading frame would lead to the synthesis of signal peptides of 29,42,47,49,55 and 59 residues.

Hydropathy Pattern

The hydropathy pattern coding sequence of the protein of 32-kDa of the invention and that of the antigen α of BCG (17) were determined by the method of Kyte and Doolittle (15). The nonapeptide profiles are shown in FIG. 6. Besides the initial hydrophobic signal peptide region, several hydrophilic domains could be identified. It is interesting to note that the overall hydrophilicity pattern of the protein of 32-kDa of the invention is comparable to that of the BCG antigen α. For both proteins, a domain of highest hydrophilicity could be identified between amino acid residues 200 and 250.

Homology

Matsuo et al. (17) recently published the sequence of a 1095 nucleotide cloned DNA corresponding to the gene coding for the antigen α of BCG. The 978 bp coding region of M. bovis antigen α as revised in Infection and Immunity, vol. 58, p. 550–556, 1990, and 1017 bp coding regions of the protein of 32-kDa of the invention show a 77.5% homology, in an aligned region of 942 bp. At the amino acid level both precursor protein sequences share 75.6% identical residues. In addition, 17.6% of the amino acids correspond to evolutionary conserved replacements as defined in the algorithm used for the comparison (PAM250 matrix, ref 23). FIG. 7 shows sequence divergences in the N-terminal of the signal peptide. The amino terminal sequence—32 amino acids—of both mature proteins is identical except for position 31.

Human Sera Recognize the Recombinant 32-kDa Protein

FIG. 8 shows that serum samples from tuberculous patients when immunoblotted with a crude *E. coli* extract expressing clone 17 distinctly react with the 140 kDa fusion protein (lanes 4 to 6) contain the protein of 32-kDa of the invention, but not with unfused β-galactosidase expressed in a parallel extract (lanes 10 to 12). Serum samples from two negative controls selected as responding very little to the purified protein of 32-kDa of the invention does neither recognize the 140 kDa fused protein containing the protein of 32-kDa of the invention, nor the unfused β-galactosidase (lanes 2, 3 and 8 and 9). The 140 k-Da fused protein and the unfused β-galactosidase were easily localized reacting with the anti-β-galactosidase monoclonal antibody (lanes 1 to 7).

The invention has enabled to prepare a DNA region coding particularly for a protein of 32-kDa (cf. FIG. 5); said DNA region containing an open reading frame of 338 codons (stop codon non included). At position 220 a TTT encoding the first amino acid of the mature protein is followed by the 295 triplets coding for the mature protein of 32-kDa. The size of this open reading frame, the immunoreactivity of the derived fusion proteins, the presence of a signal peptide and, especially, the identification within this gene of a $NH_2$-terminal region highly homologous to that found in the MPB 59 antigen (31/32 amino acids homology) and in the BCG antigen α (31/32 amino acids homology) (see FIG. 7), strongly suggest that the DNA fragment described contains the complete cistron encoding the protein of 32-kDa secreted by *M. tuberculosis*, and which had never been so far identified in a non ambiguous way.

Six ATG codons were found to precede this TTT at position 220 in the same reading frame. Usage of any of these ATGs in the same reading frame would lead to the synthesis of signal peptides of 43, 48, 50, 56 or 60 residues. Among these various possibilities, initiation is more likely to take place either at $ATG_{91}$ or $ATG_{52}$ because both are preceded by a plausible *E. coli*-like promoter and a Shine-Dalgarno motif.

If initiation takes place at $ATG_{91}$, the corresponding signal peptide would code for a rather long peptide signal of 43 residues. This length however is not uncommon among secreted proteins from Gram positive bacteria (5). It would be preceded by a typical *E. coli* Shine-Dalgarno motif (4/6 residues homologous to AGGAGG) at a suitable distance.

If initiation takes place at $ATG_{52}$, the corresponding signal peptide would code for a peptide signal of 56 residues but would have a less stringent Shine-Dalgarno ribosome binding site sequence.

The region encompassing the translation termination triplet was particularly sensitive to secondary structure effects which lead to so-called compressions on the sequencing gels. In front of the TAG termination codon at position 1105, 22 out of 23 residues are G-C base pairs, of which 9 are G's.

Upstream $ATG_{130}$, a sequence resembling an *E. coli* promoter (11) comprising an hexanucleotide (TTGAGA) (homology 5/6 to TTGACA) and a AAGAAT box (homology 4/6 to TATAAT) separated by 16 nucleotides was observed. Upstream the potential initiating codon $ATG_{91}$, one could detect several sequences homologous to the *E. coli* "–35 hexanucleotide box", followed by a sequence resembling a TATAAT box. Among these, the most suggestive is illustrated on FIGS. 3*a* and 3*b*. It comprises a TTGGCC at position 59 (FIGS. 3*a* and 3*b*) (homology 4/6 to TTGACA) separated by 14 nucleotides from a GATAAG (homology 4/6 to TATAAT). Interestingly this putative promoter region shares no extensive sequence homology with the promoter region described for the BCG protein α-gene (17) nor with that described for the 65 kDa protein gene (26, 28).

Searching the NBRF data bank (issue 16.0) any significant homology between the protein of 32-kDa of the invention and any other completely known protein sequence could not be detected. In particular no significant homology was observed between the 32-kDa protein and α and β subunits of the human fibronectin receptor (1). The $NH_2$-terminal sequence of the 32-kDa protein of the invention is highly homologous—29/32 amino acids—to that previously published for BCG MPB 59 antigen (34) and to that of BCG α-antigen—31/32 amino acids—(Matsuo, 17) and is identical in its first 6 amino acids with the 32-kDa protein of *M. bovis* BCG (9). However, the presumed initiating methionine precedes an additional 29 or 42 amino acid hydrophobic sequence which differs from the one of α-antigen (cf. FIG. 7), but displaying all the characteristics attributed to signal sequences of secreted polypeptides in prokaryotes (22).

Interestingly, no significant homology between the nucleic acid (1–1358) of the invention (cf. FIGS. 3*a* and 3*b*) and the DNA of the antigen α of Matsuo exists within their putative promoter regions.

EXAMPLE II

Construction of a Bacterial Plasmid Containing the Entire Coding Sequence of the 32-kDa Protein of M. tuberculosis In the previous example, in FIG. 2, the various overlapping λgt11 isolates covering the 32-kDa protein gene region from *M. tuberculosis* were described. Several DNA fragments were subcloned from these λgt11 phages in the Blue Scribe M13+ plasmid (Stratagene). Since none of these plasmids contained the entire coding sequence of the 32-kDa protein gene, a plasmid containing this sequence was reconstructed.

Step 1: Preparation of the DNA Fragments:

1) The plasmid BS-By5-800 obtained by subcloning HindIII fragments of By5 (cf. FIG. 2) into the Blue Scribe $M13^+$ plasmid (Stratagene), was digested with HindIII and a fragment of 800 bp was obtained and isolated from a 1% agarose gel by electroelution.

2) The plasmid BS-4.1 obtained by subcloning the 2.7 kb EcoRI insert from λgt11-17) into the Blue Scribe $M13^+$ plasmid (Stratagene) (see FIG. 2 of patent application) was digested with HindIII and SphI and a fragment of 1500 bp was obtained and isolated from a 1% agarose gel by electroelution.

3) Blue Scribe $M13^+$ was digested with HindIII and SphI, and treated with calf intestine alkaline phosphatase (special quality for molecular biology, Boehringer Mannheim) as indicated by the manufacturer.

Step 2: Ligation:

The ligation reaction contained:

125 ng of the 800 bp HindIII fragment (1)

125 ng of the 1500 bp SphI-HindIII insert (2)

50 ng of the HindIII-SphI digested $BSM13^+$ vector (3)

2 μl of 10 ligation buffer (Maniatis et al., 1982)

1 μl of (=2.5 U) of T4 DNA ligase (Amersham)

4 μl PEG 6000, 25% (w/v)

8 μl $H_2O$

The incubation was for 4 hours at 16° C.

Step 3: Transformation:

100 μl of DH5α *E. coli* (Gibco BRL) were transformed with 10 μl of the ligation reaction (step 2) and plated on IPTG, X-Gal ampicillin plates, as indicated by the manufacturer. About 70 white colonies were obtained.

Step 4:

As the 800 bp fragment could have been inserted in both orientations, plasmidic DNA from several clones were analyzed by digestion with PstI in order to select one clone (different from clone 11), characterized by the presence of 2 small fragments of 229 and 294 bp. This construction contains the HindIII-HindIII-SphI complex in the correct orientation. The plasmid containing this new construction was called: "BS.BK.$P_{32}$.complet".

EXAMPLE III

Expression of a Polypeptide of the Invention in *E. coli*

The DNA sequence coding for a polypeptide, or part of it, can be linked to a ribosome binding site which is part of the expression vector, or can be fused to the information of another protein or peptide already present on the expression vector.

In the former case the information is expressed as such and hence devoid of any foreign sequences (except maybe for the aminoterminal methionine which is not always removed by *E. coli*).

In the latter case the expressed protein is a hybrid or a fusion protein.

The gene, coding for the polypeptide, and the expression vector are treated with the appropriate restriction enzyme(s) or manipulated otherwise as to create termini allowing ligation. The resulting recombinant vector is used to transform a host. The transformants are analyzed for the presence and proper orientation of the inserted gene. In addition, the cloning vector may be used to transform other strains of a chosen host. Various methods and materials for preparing recombinant vectors, transforming them to host cells and expressing polypeptides and proteins are described by Panayatatos, N., in "Plasmids, a practical approach (ed. K. G. Hardy, IRL Press) pp. 163–176, by Old and Primrose, principals of gene manipulation (2d Ed, 1981) and are well known by those skilled in the art.

Various cloning vectors may be utilized for expression. Although a plasmid is preferable, the vector may be a bacteriophage or cosmid. The vector chosen should be compatible with the host cell chosen.

Moreover, the plasmid should have a phenotypic property that will enable the transformed host cells to be readily identified and separated from those which are not transformed. Such selection genes can be a gene providing resistance to an antibiotic like for instance, tetracycline carbenicillin, kanamycin, chloramphenicol, streptomycin, etc.

In order to express the coding sequence of a gene in *E. coli* the expression vector should also contain the necessary signals for transcription and translation.

Hence it should contain a promoter, synthetic or derived from a natural source, which is functional in *E. coli*. Preferably, although usually not absolutely necessary, the promoter should be controllable by the manipulator. Examples of widely used controllable promoters for expression in *E. coli* are the lac, the trp, the tac and the lambda PL and PR promoter.

Preferably, the expression vector should also contain a terminator of transcription functional in *E. coli*. Examples of used terminators of transcription are the trp and the rrnB terminators.

Furthermore, the expression vector should contain a ribosome binding site, synthetic or from a natural source, allowing translation and hence expression of a downstream coding. sequence. Moreover, when expression devoid of foreign sequences is desired, a unique restriction site, positioned in such a way that it allows ligation of the sequence directly to the initiation codon of the ribosome binding site, should be present.

A suitable plasmid for performing this type of expression is pKK233-2 (Pharmacia). This plasmid contains the trc promoter, the lac Z ribosome binding site and the rrnB transcription terminator.

Also suitable is plasmid pIGRI (Innogenetics, Ghent, Belgium). This plasmid contains the tetracycline resistance gene and the origin of replication of $pAT_{153}$ (available from Bioexcellence, Biores B.V., Woerden, The Netherlands), the lambda PL promoter up to the MboII site in the 5' untranslated region of the lambda N gene (originating from pPL(λ); Pharmacia).

Downstream from the PL promoter, a synthetic sequence was introduced which encodes a "two cistron" translation casette whereby the stop codon of the first cistron (being the first 25 amino acids of TNF, except for Leu at position 1 which is converted to Val) is situated between the Shine-Dalgarno sequence and the initiation codon of the second ribosome binding site. The restriction and genetic map of pIGRI is represented in FIG. 10a.

FIG. 10b and Table 5 represent respectively the nucleic acid sequence and complete restriction site analysis of pIGRI.

However, when expression as a hybrid protein is desired, then the expression vector should also contain the coding sequence of a peptide or polypeptide which is (preferably highly) expressed by this vector in the appropriate host.

In this case the expression vector should contain a unique cleavage site for one or more restriction endonucleases downstream of the coding sequence.

Plasmids pEX1, 2 and 3 (Boehringer, Mannheim) and pUEX1, 2 and 2 (Amersham) are useful for this purpose.

They contain an ampicillin resistance gene and the origin of replication of pBR322 (Bolivar at al. (1977) Gene 2, 95–113), the lac Z gene fused at its 5' end to the lambda PR promoter together with the coding sequence for the 9 first amino acids of its natural gene cro, and a multiple cloning site at the 3' end of the lac Z coding sequence allowing production of a beta galactosidase fused polypeptide.

The pUEX vectors also contain the CI857 allele of the bacteriophage lambda CI repressor gene.

Also useful is plasmid pmTNF MPH (Innogenetics). It contains the tetracycline resistance gene and the origin of replication of $pAT_{153}$ (obtainable from Bioexcellence, Biores B.V., Woerden. The Netherlands), the lambda PL promoter up to the MboII site in the N gene 5' untranslated region (originating from pPL(λ); Pharmacia), followed by a synthetic ribosome binding site (see sequence data), and the information encoding the first 25 AA of mTNF (except for the initial Leu which is converted to Val). This sequence is, in turn, followed by a synthetic polylinker sequence which encodes six consecutive histidines followed by several proteolytic sites (a formic acid, CNBr, kallikrein, and E. coli protease VII sensitive site, respectively), each accessible via a different restriction enzyme which is unique for the plasmid (SmaI, NcoI, BspMII and StuI, respectively; see restriction and genetic map, FIG. 11a). Downstream from the polylinker, several transcription terminators are present including the E. coli trp terminator (synthetic) and the $rrnBT_1T_2$ (originating from pKK223-3; Pharmacia). The total nucleic acid sequence of this plasmid is represented in FIG. 11b.

Table 6 gives a complete restriction site analysis of pmTNF MPH.

The presence of 6 successive histidines allows purification of the fusion protein by Immobilized Metal Ion Affinity Chromatography (IMAC).

After purification, the foreign part of the hybrid protein can be removed by a suitable protein cleavage method and the cleaved product can then be separated from the uncleaved molecules using the same IMAC based purification procedure.

In all the above-mentioned plasmids where the lambda PL or PR promoter is used, the promoter is temperature-controlled by means of the expression of the lambda cI ts 857 allele which is either present on a defective prophage incorporated in the chromosome of the host (K12ΔH, ATCC no. 33767) or on a second compatible plasmid (pACYC derivative). Only in the pUEX vectors is this cI allele present on the vector itself.

It is to be understood that the plasmids presented above are exemplary and other plasmids or types of expression vectors maybe employed without departing from the spirit or scope of the present invention.

If a bacteriophage or phagemid is used, instead of plasmid, it should have substantially the same characteristics used to select a plasmid as described above.

EXAMPLE IV

Subcloning of the P32 Antigen in Plasmid pIGRI

Fifteen μg of plasmid "BS-BK-$P_{32}$ complet" (see Example II) was digested with EclXI and BstEII (Boehringer, Mannheim) according to the conditions recommended by the supplier except that at least 3 units of enzyme were used per μg of DNA. EclXI cuts at position 226 (FIG. 5) and BstEII at position 1136, thus approaching very closely the start and stop codon of the mature $P_{32}$ antigen. This DNA is hereafter called DNA coding for the "$P_{32}$ antigen fragment".

The DNA coding for the "$P_{32}$ antigen fragment" (as defined above) is subcloned in pIGRI (see FIG. 10a) for expression of a polypeptide devoid of any foreign sequences. To bring the ATG codon of the expression vector in frame with the $P_{32}$ reading frame, an intermediary construct is made in pIG2 (for restriction and genetic map, see FIG. 12a; DNA sequences, see FIG. 12b; complete restriction site analysis, see Table 7).

Five μg of plasmid pIG2 is digested with NcoI. Its 5' sticky ends are filled in prior to dephosphorylation.

Therefore, the DNA was incubated in 40 μl NB buffer (0.05 M Tris-Cl pH 7.4; 10 mM $MgCl_2$; 0.05% β-mercaptoethanol) containing 0.5 mM of all four dXTP (X=A,T,C,G) and 2 μl of Klenow fragment of E. coli DNA polymerase I (5 U/μl, Boehringer, Mannheim) for at least 3 h at 15° C.

After blunting, the DNA was once extracted with one volume of phenol equilibrated against 200 mM Tris-Cl pH 8, twice with at least two volumes of diethylether and finally collected using the "gene clean kit™" (Bio101) as recommended by the supplier. The DNA was then dephosphorylated at the 5' ends in 30 μl of CIP buffer (50 mM TrisCl pH 8, 1 mM $ZnCl_2$) and 20 to 25 units of calf intestine phosphatase (high concentration, Boehringer, Mannheim). The mixture was incubated at 37° C. for 30 min, then EGTA (ethyleneglycol bis (β-aminoethylether)-N,N,N',N' tetraacetic acid) pH 8 is added to a final concentration of 10 mM. The mixture was then extracted with phenol followed by diethylether as described above, and the DNA was precipitated by addition of 1/10 volume of 3 M KAc ($Ac=CH_3COO$) pH 4.8 and 2 volumes of ethanol followed by storage at −20° C. for at least one hour.

After centrifugation at 13000 rpm in a Biofuge A (Hereaus) for 5 min the pelleted DNA was dissolved in $H_2O$ to a final concentration of 0.2 μg/μl.

The EclXI-BstEII fragment, coding for the "$P_{32}$ antigen fragment" (see above) was electrophoresed on a 1% agarose gel (BRL) to separate it from the rest of the plasmid and was isolated from the gel by centrifugation over a Millipore HVLP filter (φ2 cm) (2 min, 13000 rpm, Biofuge at room temperature) and extracted with Tris equilibrated phenol followed by diethylether as described above.

The DNA was subsequently collected using the "Gene clean kit™" (Bio101) as recommended by the supplier.

After that, the 5' sticky ends were blunted by treatment with the Klenow fragment of E. coli DNA polymerase I as described above and the DNA was then again collected using the "Gene clean kit™" in order to dissolve it in 7 μl of $H_2O$.

One µl of vector DNA is added together with one µl of 10× ligase buffer (0.5 M TrisCl pH 7.4, 100 mM $MgCl_2$, 5 mM ATP, 50 mM DTT (dithiothreitol)) and 1 µl of T4 DNA ligase (1 unit/µl, Boehringer, Mannheim). Ligation was performed for 6 h at 13° C. and 5 µl of the mixture is then used to transform strain DH1 (lambda) [strain DH1—ATCC No. 33849—lysogenized with wild type bacteriophage λ] using standard transformation techniques as described for instance by Maniatis et al. in "Molecular cloning, a laboratory manual", Cold Spring Harbor Laboratory (1982).

Individual transformants are grown and lysed for plasmid DNA preparation using standard procedures (Experiments with gene fusions, Cold Spring Harbor Laboratory (1984) (T. J. Silhavy, H. L. Berman and L. W. Enquist, eds) and the DNA preparations are checked for the correct orientation of the gene within the plasmid by restriction enzyme analysis.

A check for correct blunting is done by verifying the restoration of the NcoI site at the 5' and 3' end of the antigen coding sequence. One of the clones containing the $P_{32}$ antigen fragment in the correct orientation is kept for further work and designated $pIG_2$-Mt32. In this intermediary construct, the DNA encoding the antigen is not in frame with the ATG codon. However, it can now be moved as a NcoI fragment to another expression vector.

15 µg of $pIG_2$-Mt32 is digested with NcoI. The NcoI fragment encoding the $P_{32}$ antigen is gel purified and blunted as described above. After purification, using "gene clear kit TM" it is dissolved in 7 µl of $H_2O$.

5 µg of plasmid pIGRI is digested with NcoI, blunted and dephosphorylated as described above. After phenol extraction, followed by diethylether and ethanol precipitation, the pellet is dissolved in $H_2O$ to a final concentration of 0.2 µg/µl.

Ligation of vector and "antigen fragment" DNA is carried out as described above. The ligation mixture is then transformed into strain DH1 (lambda) and individual transformants are analysed for the correct orientation of the gene within the plasmid by restriction enzyme analysis. A check for correct blunting is done by verifying the creation of a new NsiI site at the 5' and 3' ends of the antigen coding sequence. One of the clones containing the $P_{32}$ antigen fragment in the correct orientation is kept for further work and designated pIGRI.Mt32.

EXAMPLE V

Subcloning of the P32 Antigen in pmTNF MPH

Fifteen µg of the plasmid pIG2 Mt32 (see example IV) was digested with the restriction enzyme NcoI (Boehringer, Mannheim), according to the conditions recommended by the supplier except that at least 3 units of enzyme were used per µg of DNA.

After digestion, the reaction mixture is extracted with phenol equilibrated against 200 mM TrisCl pH 8, (one volume), twice with diethylether (2 volumes) and precipitated by addition of 1/10 volume of 3 M KAc ($Ac=CH_3COO$) pH 4.8 and 2 volumes of ethanol followed by storage at −20° C. for at least one hour.

After centrifugation for 5 minutes at 13000 rpm in a Biofuge A (Hereaus) the DNA is electrophoresed on a 1% agarose gel (BRL).

The DNA coding for the "$P_{32}$ antigen fragment" as described above, is isolated by centrifugation over a Millipore HVLP filter (φ2 cm) (2 minutes, 13000 rpm, Biofuge at room temperature) and extracted one with trisCl equilibrated phenol and twice with diethylether. The DNA is subsequently collected using "Gene clean kit™" (Bio 101) and dissolved in 7 µl of $H_2O$.

The 5' overhanging ends of the DNA fragment generated by digestion with NcoI were filled in by incubating the DNA in 40 µl NB buffer (0.05 M Tris-HCl, pH 7.4; 10 mM $MgCl_2$; 0.05% β-mercaptoethanol) containing 0.5 mM of all four dXTPS (X=A, T, C, G) and 2 µl of Klenow fragment of *E. coli* DNA polymerase I (5 units/µl Boehringer Mannheim) for at least 3 h at 15° C. After blunting, the DNA was extracted with phenol, followed by diethylether, and collected using a "gene clean kit™" as described above.

Five µg of plasmid pmTNF MPH is digested with StuI, subsequently extracted with phenol, followed by diethylether, and precipitated as described above. The restriction digest is verified by electrophoresis of a 0.5 µg sample on an analytical 1.2% agarose gel.

The plasmid DNA is then desphosphorylated at the 5' ends to prevent self-ligation in 30 µl of CIP buffer (50 mM TrisCl pH 8, 1 mM ZnCl2) and 20 to 25 units of calf intestine phosphatase (high concentration, Boehringer Mannheim). The mixture is incubated at 37° C. for 30 minutes, then EGTA (ethyleneglycol bis (β-aminoethylether)-N,N,N',N' tetraacetic acid) pH8 is added to a final concentration of 10 mM. The mixture is extracted with phenol followed by diethylether and the DNA is precipitated as described above. The precipitate is pelleted by centrifugation in a Biofuge A (Hereaus) at 13000 rpm for 10 min at 4° C. and the pellet is dissolved in $H_2O$ to a final DNA concentration of 0.2 µg/µl.

One µl of this vector DNA is mixed with the 7 µl solution containing the DNA fragment coding for the "P32antigen fragment" (as defined above) and 1 µl 10× ligase buffer (0.5 M TrisCl pH7.4, 100 mM MgCl2, 5 mM ATP, 50 mM DTT (dithiothreitol)) plus 1 µl $T_4$ DNA ligase (1 unit/µl, Boehringer Mannheim) is added. The mixture is incubated at 13° C. for 6 hours and 5 µl of the mixture is then used for transformation into strain DH1 (lambda) using standard transformation techniques are described by for instance Maniatis et al. in "Molecular cloning, a laboratory manual", Cold Spring Harbor Laboratory (1982).

Individual transformants are grown and then lysed for plasmid DNA preparation using standard procedures (Experiments with gene fusions, Cold Spring Harbor Laboratory 1984 (T. J. Silhavy, M. L. Berman and L. W. Enquist eds.)) and are checked for the correct orientation of the gene within the plasmid by restriction enzyme analysis.

One of the clones containing the DNA sequence encoding the antigen fragment in the correct orientation was retained for further work and designated pmTNF-MPH-Mt32. It encodes all information of the $P_{32}$ antigen starting from position +4 in the amino acid sequence (see FIG. 5). The amino acid sequence of the total fusion protein is represented in FIG. 13.

EXAMPLE VI

Induction of Antigen Expression from pmTNF MPH Mt32

A—Material and Methods

DNA of pmTNF-MPH-Mt32 is transformed into *E. coli* strain K12ΔH (ATCC 33767) using standard transformation procedures except that the growth temperature of the cultures is reduced to 28° C. and the heat shock temperature to 34° C.

A culture of K12ΔH harboring pmTNF-MPH-Mt32, grown overnight in Luria broth at 28° C. with vigorous shaking in the presence of 10 μg/ml tetracycline, is inoculated into fresh Luria broth containing tetracycline (10 μg/ml) and grown to an optical density at 600 nanometers of 0.2 in the same conditions as for the overnight culture.

When the optical density at 600 nanometers has reached 0.2 half of the culture is shifted to 42° C. to induce expression while the other half remains at 28° C. as a control. At several time intervals aliquots are taken which are extracted with one volume of phenol equilibrated against M9 salts (0.1% ammonium chloride, 0.3% potassium dihydrogenium phosphate, 1.5% disodium hydrogenium phosphate, 12 molecules of water) and 1% SDS. At the same time, the optical density (600 nm) of the culture is checked. The proteins are precipitated from the phenol phase by addition of two volumes of acetone and storage overnight at −20° C. The precipitate is pelleted (Biofuge A, 5 min., 13000 rpm, room temperature) dried at the air, dissolved in a volume of Laemmli (Nature (1970) 227:680) sample buffer (+β mercapto ethanol) according to the optical density and boiled for 3 min.

Samples are then run on a SDS polyacrylamide gel (15%) according to Laemmli (1970). Temperature induction of mTNF-His$_6$-P$_{32}$ is monitored by both Coomassie Brilliant Blue (CBB) staining and immunoblotting. CBB staining is performed by immersing the gel in a 1/10 diluted CBB staining solution (0.5 g CBB-R250 (Serva) in 90 ml methanol: H$_2$O (1:1 v/v) and 10 ml glacial acetic acid) and left for about one hour on a gently rotating platform. After destaining for a few hours in destaining solution (30% methanol, 7% glacial acetic acid) protein bands are visualised and can be scanned with a densitometer (Ultroscan XL Enhanced Laser Densitometer, LKB).

For immunoblotting the proteins are blotted onto Hybond C membranes (Amersham) as described by Townbin et al (1979). After blotting, proteins on the membrane are temporarily visualised with Ponceau S (Serva) and the position of the molecular weight markers is indicated. The stain is then removed by washing in H$_2$O. A specific protein binding sites are blocked by incubating the blots in 10% non-fat dried milk for about 1 hour on a gently rotating platform. After washing twice with NT buffer (25 mM Tris-HCl, pH 8.0; 150 mM NaCl) blots are incubated with polyclonal rabbit anti-32-kDa antiserum (1:1000), obtained as described in example I ("screening of the λgt11 *M. tuberculosis* recombinant DNA library with anti-32-kDa antiserum") in the presence of *E. coli* lysate or with monoclonal anti-hTNF-antibody which crossreacts with mTNF (Innogenetics, no. 17F5D10) for at least 2 hours on a rotating platform. After washing twice with NT buffer+0.02% Triton.X.100, blots are incubated for at least 1 hour with the secondary antiserum alkaline phosphatase-conjugated swine anti-rabbit immunoglobulins (1/500; Prosan) in the first case, and alkaline phosphatase conjugated rabbit anti-mouse immunoglobulins (1/500; Sigma) in the second case.

Blots are washed again twice with NT buffer+0.02% Triton X100 and visualisation is then performed with nitro blue tetrazolium (NBT) and 5-bromo-4-chloro-3-indolyl-phosphate (BCIP) from Promega using conditions recommended by the supplier.

B. Results

Upon induction of K12ΔH cells containing pmTNF-MPH-Mt32, a clearly visible band of about 35-kDa appears on CBB stained gels, already one hour after start of induction (FIG. 14a). This band, corresponding to roughly 25% of total protein contents of the cell, reacts strongly with anti-32-kDa and anti-mTNF antisera on immunoblots (FIG. 14b). However, this band represents a cleavage product of the original fusion protein, since a minor band, around 37 kDa, is also visible on immunoblots, reacting specifically with both antisera as well. This suggests that extensive cleavage of the recombinant mTNF-His$_6$-P$_{32}$ takes place about 2–3 kDa from its carboxyterminal end.

EXAMPLE VII

Purification of Recombinant Antigen on Immobilized Metal Ion Affinity Chromatography (IMAC)

The hybrid protein mTNF-His$_6$-P$_{32}$ (amino acid sequence, see FIG. 13) expressed by K12ΔH cells containing pmTNF.MPH.Mt32, is especially designed to facilitate purification by IMAC, since the 6 successive histidines in the polylinker sequence bring about a strong affinity for metal ions (HOCHULI et al, 1988).

a. Preparation of the Crude Cell Extract:

12 l of *E. coli* cells K12ΔH containing plasmid pmTNF-MPH-Mt32 were grown in Luria Broth containing tetracycline (10 μg/ml) at 28° C. to an optical density (600 nm) of 0.2 and then induced by shifting the temperature to 42° C. After 3 hours of induction, cells were harvested by centrifugation (Beckman, JA 10 rotor, 7,500 rpm, 10 min). The cell paste was resuspended in lysis buffer (10 mM KCl, 10 mM Tris-HCl pH 6.8, 5 mM EDTA) to a final concentration of 50% (w/v) cells.

ε-NH$_2$-capronic acid and dithiotreitol (DTT) were added to a final concentration of resp. 20 mM and 1 mM, to prevent proteolytic degradation. This concentrated cell suspension was stored overnight at −70° C.

Cells were lysed by passing them three times through a French press (SLM-Aminco) at a working pressure of 800–1000 psi. During and after lysis, cells were kept systematically on ice.

The cell lysate was cleared by centrifugation (Beckman, JA 20, 18,000 rpm, 20 min, 4° C.). The supernatant (SN) was carefully taken off and the pellet, containing membranes and inclusion bodies, was kept for further work since preliminary experiments had shown that the protein was mainly localised in the membrane fraction.

7 M guanidinium hydrochloride (GuHCl, marketed by ICN) in 100 mM phosphate buffer pH 7.2 was added to the pellet volume to a final concentration of 6 M GuHCl. The pellet was resuspended and extracted in a bounce tissue homogenizer (10 cycles).

After clearing (Beckman, JA 20, 18,000 rpm, 20 min, 4° C.), about 100 ml of supernatant was collected (=extract 1) and the removing pellet was extracted again as described above (=extract 2, 40 ml).

The different fractions (SN,EX1,EX2) were analysed on SDS-PAGE (Laemmli, Nature 1970; 227:680) together with control samples of the induced culture. Scanning of the gel revealed that the recombinant protein makes up roughly 25% of the total protein content of the induced cell culture. After fractionation most of the protein was found back in the extracts. No difference was noticed between reducing and non-reducing conditions (plus and minus β-mercaptoethanol).

b. Preparation of the Ni++ IDA (Imino Diacetic Acid) Column:

5 ml of the chelating gel, Chelating Sepharose 6B (Pharmacia) is washed extensively with water to remove the ethanol in which it is stored and then packed in a "Econo-column" (1×10 cm, Biorad). The top of the column is connected with the incoming fluid (sample, buffer, etc) while the end goes to the $UV_{280}$ detector via a peristaltic jump. Fractions are collected using a fraction collector and, when appropriate, pH of the fractions is measured manually.

The column is loaded with Ni++ (6 ml $NiCl_2.6H_2O$; 5 µg/µl) and equilibrated with starting buffer (6 M guanidinium hydrochloride, 100 mM phosphate buffer, pH 7.2).

After having applied the sample, the column is washed extensively with starting buffer to remove unbound material.

To elute the bound material, 2 different elution procedures are feasible:
1) elution by decreasing pH,
2) elution by increasing imidazol concentration.

Both will be discussed here.

To regenerate the column, which has to be done after every 2–3 runs, 20 ml (about 5 column volumes) of the following solutions are pumped successively through the column:

0.05 M EDTA-0.5 M NaCl
0.1 M NaOH
$H_2O$
6 ml $NiCl_2.6H_2O$ (5 mg/ml).

After equilibrating with starting buffer the column is ready to use again.

c. Chromatography:

All buffers contained 6 M guanidinium hydrochloride throughout the chromatography. The column was developed at a flow rate of 0.5 ml/min at ambient temperature. Fractions of 2 ml were collected and, when appropriate, further analysed by SDS-PAGE and immunoblotting. Gels were stained with Coomassie Brilliant Blue R250 and silver stain, as described by ANSORGE (1985). Immunoblotting was carried out as described in example I. The primary antiserum used was either polyclonal anti-32kDa-antiserum (1/1000) obtained as described in example I ("screening of the λgt11 M. tuberculosis recombinant DNA library with anti-32kDa-antiserum") or anti-E. coli-immunoglobulins (1/500; PROSAN), or monoclonal anti-hTNF-antibody which cross-reacts with mTNF (Innogenetics, No. 17F5D10). The secondary antiserum was alkaline phosphatase conjugated swine anti-rabbit immunoglobulins (1/500, PROSAN), or alkaline phosphatase conjugated rabbit-anti-mouse immunoglobulins (1/500, Sigma).

C1. Elution with Decreasing pH:
Solutions used:
A: 6 M GuHCl 100 mM phosphate pH 7.2
B: 6 M GuHCl 25 mM phosphate pH 7.2
C: 6 M GuHCl 50 mM phosphate pH 4.2

After applying 3 ml of extract 1 ($OD_{280}$=32.0) and extensively washing with solution A, the column is equilibrated with solution B and then developed with a linear pH gradient from 7.2 to 4.2 (25 ml of solution B and 25 ml of solution C were mixed in a gradient former). The elution profile is shown in FIG. 15.

From SDS-PAGE analysis (Coomassie and silverstain) it was clear that most of the originally bound recombinant protein was eluted in the fractions between pH 5.3 and 4.7.

Screening of these fractions on immunoblot with anti-32-kDa and the 17F5D10 monoclonal antibody showed that, together with the intact recombinant protein, also some degradation products and higher aggregation forms of the protein were present, although in much lower amount. Blotting with anti-E. coli antibody revealed that these fractions (pH 5.3–4.7) still contained immunodetectable contaminating E. coli proteins (75, 65, 43, 35 and 31 kDa bands) and lipopolysaccharides.

C2. Elution with Increasing Imidazol Concentration:
Solutions used:
A: 6 M GuHCl 100 mM phosphate pH 7.2
B: 6 M GuHCl 50 mM imidazol pH 7.2
C: 6 M GuHCl 100 mM imidazol pH 7.2
D: 6 M GuHCl 15 mM imidazol pH 7.2
E: 6 M GuHCl 25 mM imidazol pH 7.2
F: 6 M GuHCl 35 mM imidazol pH 7.2

Sample application and washing was carried out as in C1, except that after washing, no equilibration was necessary with 6 M GuHCl 25 mM phosphate. The column was first developed with a linear gradient of imidazol going from 0 to 50 mM (25 ml of solution A and 25 ml of solution B were mixed in a gradient former) followed by a step elution to 100 mM imidazol (solution C). During the linear gradient, proteins were gradually eluted in a broad smear, while the step to 100 mM gave rise to a clear peak (FIG. 16).

SDS-PAGE analysis of the fractions revealed that in the first part of the linear gradient (fr 1–24) most contaminating E. coli proteins were washed out, while the latter part of the gradient (fr 25–50) and the 100 mM peak contained more than 90% of the recombinant protein.

As in C1, these fractions showed, besides a major band of intact recombinant protein, some minor bands of degradation and aggregation products. However, in this case, the region below 24-kDa seemed nearly devoid of protein bands, which suggests that less degradation products co-elute with the intact protein. Also, the same contaminating E. coli proteins were detected by immunoblotting, as in C1, although the 31-kDa band seems less intense and even absent in some fractions.

In a second stage, we developed the column with a step gradient of increasing imidazol concentrations. After having applied the sample and washed the column, 2 column volumes (about 8 ml) of the following solutions were brought successively onto the column solution D, E, F and finally 4 column volumes of solution C. The step gradient resulted in a more concentrated elution profile (FIG. 17) which makes it more suitable for scaling up purposes.

In conclusion, the mTNF-$His_6$-$P_{32}$ protein has been purified to at least 90% by IMAC. Further purification can be achieved through a combination of the following purification steps:

IMAC on chelating superose (Pharmacia)
ion exchange chromatography (anion or cation)
reversed phase chromatography
gel filtration chromatography
immunoaffinity chromatography
elution from polyacrylamide gel.

These chromatographic methods are commonly used for protein purification.

The plasmids of FIGS. 10b, 11b and 12b are new.

BIBLIOGRAPHY

1. Abou-Zeid, C., T. L. Ratliff, H. G. Wiker, M. Harboe, J. Bennedsen and G. A. W. Rook, 1988. Characterization of fibronectin-biding antigens released by Mycobacterium tuberculosis and Mycobacterium bovis BCG. Infect. Imm. 56, 3046–3051.

2. Bellon, B. 1988. Apple Macintosh programs for nucleic and protein sequence analysis. Nucleic Acid Res. 16:1837–1846.
3. Bibb, M. J., P. R. Findlay and M. W. Jonhson. 1984. The relationship between base composition and codon usage in bacterial genes and its use for the simple and reliable identification of protein-coding sequences. Gene. 30: 157–166.
4. Bresson, G. M. and K. K. Stanley. 1987. pUEX, a bacterial expression vector related to pEX with universal host specificity. Nucl. Aci. Res. 15:10056.
5. Chang, S. Engineering for protein secretion in Gram positive bacteria. Methods Enzymol., 153:507–516.
6. Chen, E. J. and P. H. Seeburg. 1985. Supercoil sequencing: a fast simple method for sequencing plasmid DNA.DNA 4:165–170.
7. Closs, O., M. Harboe, N. H. Axelsen-Christensen and M. Magnussen. 1980. The antigens of *Mycobacterium bovis*, strain BCG, studied by cross-immuno-electrophoresis: a reference system. Scand. J. Immunol. S12N:249–263.
8. De Bruyn, J. R. Bosmans, J. Nyabenda and J. P. Van Vooren. 1989. Effect of zinc deficiency of the appearance of two immunodominant protein antigens (32-kDa and 65-kDa) in culture filtrates of Mycobacteria. J. Gen. Micriob. 135: 79–84.
9. De Bruyn, J., K. Huygen, R. Bosmans, M. Fauville, R. Lippens, J. P. Van Vooren, P. Falmagne, M. Weckx, H. G. Wiker, M. Harboe and M. Turneer. 1987. Purification, partial characterization and identification of a 32-kDa protein antigen of *Mycobacterium bovis* BCG. Microb. Pathogen. 2:351–366.
10. Felnberg, A. P. and R. Vogelstein. 1983. A technique for radiolabelling DNA restriction endonuclease fragments to high specific activity. Anal. Biochem. 132:6–13.
11. Hawley, D. K. and W. R. Mc Clure. 1983. Compilation and analysis of *E. coli* promoter DNA sequences. Nucleic Acids Res. 11:2237–2255.
12. Huygen, K., J. P. Van Vooren, M. Turneer, R. Bosmans, P. Dierckx and J. De Bruyn. 1988. Specific lymphoproliferation-interferon production and serum immunoglobulin G directed against a purified 32-kDa Mycobacterial antigen (P32) in patient with active tuberculosis. Scand. J. Immunol. 27:187–194.
13. Huygen, K., K. Palfliet, F. Jurton, J. Hilgers, R. ten Berg, J. P. Van Vooren and J. De Bruyn. 1989. H-2-linked control of in vitro interferon production in response to 32-kilodalton (P32) of *Mycobacterium bovis bacillus* Calmette-Guerin. Infect. Imm. 56:3196–3200.
14. Huynh, T. V., R. A. Young and R. W. Davis. 1985. Constructing and screening libraries in gt10 and gt11 p. 49–78. in: DNA cloning. Vol. I, A practical approach. Ed. D. M. Glover. IRL Press, Oxford-Washington, D.C.
15. Kyte, J. and R. F. Doolittle. 1982. Simple method for displaying the hydropathy character of a protein. J. Mol. Biol. 157:105–132.
16. Maniatis, T., E. F. Fritsch and J. Sambrook. 1982. Molecular cloning: a laboratory manual. Cold Spring Harbor Laboratory, Cold Spring Harbor, N.Y.
17. Matsuo, K., R. Yamaguchi, A. Yamazaki, H. Tasaka and T. Yamada. 1988. Cloning and expression of the *Mycobacterium bovis* BCG gene for extracellular α-antigen. J. Bacteriol. 170:3847–3854.
18. Mawam, A. M. and W. Gilbert. 1977. A new method for sequencing DNA. Proc. Natl. Acad. Sci. USA. 74:560–564.
19. Mehra, V., D. sweetser and R. A. Young. 1986. Efficient mapping of protein antigenic determinants. Proc. Natl. Acad. Sci. USA. 83:7013–7017.
20. Mustafa, A. B., H. K. Gill, A. Nerland, W. J. Britton, V. Mehra, B. R. Bloom, R. A. Young and T. Godal. 1986. Human T-cell clones recognize a major *M. Leprae* protein antigen expressed in *E. coli*. Nature (London). 319:63–38.
21. Neesen, K. and G. Volckaert. 1989. Construction and shuttling of novel bifunctional vectors for *Streptomyces* spp. and *Escherichia coli*. J. Bacteriol. 171:1569–1573.
22. Oliver, D. 1985. Protein secretion in *Escherichia coli*. Ann. Rev. Microbiol. 39:615–648.
23. Pearson, W. R. and D. J. Lipman. 1988. Improved tools for biological sequence comparison. Proc. Natl. Acad. Sci. USA. 85:2444–2448.
24. Rumschlag, H. S., T. S. Shinnick and M. L. Cohen. 1988. Serological response of patients with lepromatous and tuberculous leprosy to 30-, 31- and 32-kilodalton antigens of *Mycobacterium tuberculosis*. J. Clin. Microbiol. 26:2200–2202.
25. Sanger, F., S. Niklon and A. R. Coulson. 1977. DNA sequencing with chain termination inhibitors. Proc. Natl. Acad. Sci. USA. 74:5463–5487.
26. Shinnick, T. M. 1987. The 65-kilodalton antigen of *Mycobacterium tuberculosis*. J. Bacteriol. 169:1080–1088.
27. Thole, J. E. R., W. C. A. Van Shooten, W. J. Keulen, P. W. M. Hermans, A. A., M. Janson, R. R. P. De Vries, A. H. J. Kolk and J. D. A. Van Embden. 1988. Use of recombinant antigens expressed in *Escherichia coli* K-12 to map B-cell and T-cell epitopes on the immunodominant 65-kilodalton protein of *Mycobacterium bovis* BCG. Infect. Immun. 56:1633–1640.
28. Thole. J. E. R., W. J. Keulen, J. De Bruyn, A. H. J. Kolk, D. G. Groothuis, L. G. Berwald, R. H. Tiesjema and J. D. A. Van Embden. 1987. Characterization, sequence determination and immunogenicity of a 64-kilodalton protein of *Mycobacterium bovis* BCG expressed in *Escherichia coli* K-12. Infect. Imm. 55:1466–1475.
29. Towbin, H., T. Staehelin and J. Gordon. 1979. Electrophoretic transfer of proteins from polyacrylamide gels to nitrocellulose sheets: procedure and some applications. Proc. Natl. Acad. Sci. USA 76:4350–4354.
30. Turneer, M., J. P. Van Vooren, J. De Bruyn, E. Serruys, P. Dierckx and J. C. Yernault. 1988. Humoral immune response in human tuberculosis: immunoglobulins G, A and M directed against the purified P32 protein antigen of *Mycobacterium bovis bacillus* Calmette-Guerin. J. Clin. Microbiol. 26:1714–1719.
31. Van Vooren, J. P., C. M. Farber, E. Noel, N. Mavroudakis, M. Turneer, J. De Bruyn, F. Legros and J. C. Yernault. 1989 Local anti-P32 humoral response in tuberculous meningitis. Tubercle. 70:123–126.
32. Volckaert, G. 1987. A systematic approach to chemical sequencing by subcloning in pGV451 and derived vectors. Methods Enzymol. 155:231–250.
33. Volckaert, G., El. De Vieeschouwer, R. Frank and H. Bloecker. 1984. A novel type of cloning vectors for ultrarapid chemical degradation sequencing of DNA. Gene Anal. Techn. 1:52–59.
34. Wiker, H. G., M. Harboe, S. Nagal, M. E. Patarroyo, C. Ramirez and N. Cruz. 1986. MPB59, a widely cross-reacting protein of *Mycobacterium bovis* BCG. Int. Arch. Alllergy Appl. Immunol. 81:307–314.

35. Young, R. A., B. R. Bloom, C. M. Grosskinsky, J. Ivanji, D. Thomas and R. W. Davis. 1985. Dissection of *Mycobacterium tuberculosis* antigens using recombinant DNA. Proc. Natl. Acad; Sci. USA, 82:2583–2587.
36. HOCHULI, E., BANNWARTH, W., DÖBELI, H., GENTZ, R. and STÜCBER, D. (1988). Genetic Approach to facilitate purification of recombinant proteins with a novel metal chelate adsorbent. Biotechnology, November 1988, p. 1321–1325.
37. ANSORGE, W. (1985), Fast and sensitive detection of protein and DNA bands by treatment with potassium permanganate. J. Biochem. Biophys. Meth., 11:13–20.

The invention claimed is:

1. A composition comprising an isolated polypeptide, wherein the polypeptide comprises an amino acid sequence set forth in LYLLDGLRAQDDFSGWDINT (SEQ ID NO:25).

2. The composition of claim 1, further comprising a pharmaceutically acceptable vehicle.

3. The composition of claim 1, wherein the polypeptide consists of the amino acid sequence set forth in SEQ ID NO:25.

4. The composition of claim 3, further comprising a pharmaceutically acceptable vehicle.

5. The composition of claim 1, wherein the polypeptide further comprises a cysteine residue added at an amino or carboxyl terminal end of the polypeptide.

6. The composition of claim 1, wherein the polypeptide further comprises a tyrosine residue added at an amino or carboxyl terminal end of the polypeptide.

7. The composition of claim 1, further comprising a heterologous polypeptide sequence comprising 1 to 1000 amino acids.

8. The composition of claim 7, further comprising a pharmaceutically acceptable vehicle.

9. The composition of claim 7, wherein the heterologous polypeptide is a natural or synthetic carrier polypeptide of sufficient molecular weight for the composition to induce a cellular immune response when administered to a mammal.

10. The composition of claim 9, wherein the composition induces a cellular immune response by activating *Mycobacterium tuberculosis* antigen-responsive T-cells.

11. The composition of claim 9, wherein the composition induces the production of antibodies against *Mycobacterium tuberculosis*.

12. An immunogenic conjugate comprising a first polypeptide coupled to a second polypeptide, wherein the first polypeptide comprises an amino acid sequence set forth in SEQ ID NO:25, and the second polypeptide is a natural or synthetic polypeptide of sufficient molecular weight for the conjugate to induce a cellular immune response when administered to a mammal.

13. The conjugate of claim 12, wherein the conjugate induces a cellular immune response by activating *Mycobacterium tuberculosis* antigen-responsive T-cells.

14. The conjugate of claim 12, wherein the composition induces the production of antibodies against *Mycobacterium tuberculosis*.

15. The conjugate of claim 12, further comprising a pharmaceutically acceptable vehicle.

16. The conjugate of claim 12, wherein the first polypeptide consists of the amino acid sequence set forth in SEQ ID NO:25.

* * * * *

SEQUENCE LISTING

```
<160> NUMBER OF SEQ ID NOS: 53

<210> SEQ ID NO 1
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 1
cagcttgttg acagggttcg tggc                                              24

<210> SEQ ID NO 2
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 2
ggttcgtggc gccgtcacg                                                    19

<210> SEQ ID NO 3
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 3
cgtcgcgcgc ctagtgtcgg                                                   20

<210> SEQ ID NO 4
<211> LENGTH: 23
<212> TYPE: DNA
<213> ORGANISM: Artificial Sequence
<220> FEATURE:
<223> OTHER INFORMATION: Synthetically generated oligonucleotide

<400> SEQUENCE: 4
cggcgccgtc ggtggcacgg cga                                               23

<210> SEQ ID NO 5
<211> LENGTH: 23
<212> TYPE: DNA
<213> ORGANISM: Artificial Sequence
<220> FEATURE:
<223> OTHER INFORMATION: Synthetically generated oligonucleotide

<400> SEQUENCE: 5
cgtcggcgcg gccctagtgt cgg                                               23

<210> SEQ ID NO 6
<211> LENGTH: 18
<212> TYPE: DNA
<213> ORGANISM: Artificial Sequence
<220> FEATURE:
```

```
<223> OTHER INFORMATION: Synthetically generated oligonucleotide

<400> SEQUENCE: 6
tcgcccgccc tgtacctg                                                 18

<210> SEQ ID NO 7
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 7
gcgctgacgc tggcgatcta tc                                            22

<210> SEQ ID NO 8
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 8
ccgctgttga acgtcgggaa g                                             21

<210> SEQ ID NO 9
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 9
aagccgtcgg atctgggtgg caac                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 10
acggcactgg gtgccacgcc caac                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 11
acgcccaaca ccgggcccgc cgca                                          24

<210> SEQ ID NO 12
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 12
acgggcactg ggtgccacgc ccaac                                         25
```

<210> SEQ ID NO 13
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 13
acgccccaac accgggcccg cgcccca                                27

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
gagtacctgc aggtgccgtc gccgtcgatg ggccg                       35

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
atcaacaccc cggcgttcga gtggtac                                27

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
gtaccactcg aacgccgggg tgttgat                                27

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tgccagactt acaagtggga                                        20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tcccacttgt aagtctggca                                        20

<210> SEQ ID NO 19
<211> LENGTH: 20
<212> TYPE: DNA
<213> ORGANISM: Artificial Sequence
<220> FEATURE:
<223> OTHER INFORMATION: Primer -continued

```
<400> SEQUENCE: 19
tcctgaccag cgagctgccg                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cggcagctcg ctggtcagga                                              20

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
cctgatcggc ctggcgatgg gtgacgc                                      27

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
gcgtcaccca tcgccaggcc gatcagg                                      27

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
gcgccccagt actcccagct gtgcgt                                       26

<210> SEQ ID NO 24
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 24

Gln Val Pro Ser Pro Ser Met Gly Arg Asp Ile Lys Val Gln Phe Gln
  1               5                  10                  15

Ser Gly Gly Ala
             20

<210> SEQ ID NO 25
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 25

Leu Tyr Leu Leu Asp Gly Leu Arg Ala Gln Asp Asp Phe Ser Gly Trp
```

-continued

```
                1               5                  10                 15
Asp Ile Asn Thr
            20

<210> SEQ ID NO 26
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 26

Ser Phe Tyr Ser Asp Trp Tyr Gln Pro Ala Cys Arg Lys Ala Gly Cys
1               5                   10                  15

Gln Thr Tyr Lys
            20

<210> SEQ ID NO 27
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 27

Leu Thr Ser Glu Leu Pro Gly Trp Leu Gln Ala Asn Arg His Val Lys
1               5                   10                  15

Pro Thr Gly Ser
            20

<210> SEQ ID NO 28
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 28

Lys Ala Ser Asp Met Trp Gly Pro Lys Glu Asp Pro Ala Trp Gln Arg
1               5                   10                  15

Asn Asp Pro Leu
            20

<210> SEQ ID NO 29
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 29

Cys Gly Asn Gly Lys Pro Ser Asp Leu Gly Gly Asn Asn Leu Pro Ala
1               5                   10                  15

Lys Phe Leu Glu
            20

<210> SEQ ID NO 30
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 30
```

-continued

Lys Pro Asp Leu Gln Arg His Trp Val Pro Arg Pro Thr Pro Gly Pro
1               5                   10                  15

Pro Gln Gly Ala
            20

<210> SEQ ID NO 31
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 31

Ser Phe Tyr Ser Asp Trp Tyr Gln Pro Ala Cys Gly Lys Ala Gly Cys
1               5                   10                  15

Gln Thr Tyr Lys
            20

<210> SEQ ID NO 32
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 32

Pro Asp Leu Gln Arg Ala Leu Gly Ala Thr Pro Asn Thr Gly Pro Ala
1               5                   10                  15

Pro Gln Gly Ala
            20

<210> SEQ ID NO 33
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 33

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
            20                  25                  30

<210> SEQ ID NO 34
<211> LENGTH: 1357
<212> TYPE: DNA
<213> ORGANISM: Mycobacterium tuberculosis
<220> FEATURE:
<221> NAME/KEY: CDS
<222> LOCATION: (182)...(1240)
<220> FEATURE:
<221> NAME/KEY: sig_peptide
<222> LOCATION: (182)...(358)
<220> FEATURE:
<221> NAME/KEY: misc_feature
<222> LOCATION: 302, 306, 1198
<223> OTHER INFORMATION: n = g or gg
<220> FEATURE:
<221> NAME/KEY: misc_feature
<222> LOCATION: 308
<223> OTHER INFORMATION: n = c or cc
<220> FEATURE:
<221> NAME/KEY: misc_feature
<222> LOCATION: 620, 1103
<223> OTHER INFORMATION: n = c or g
<220> FEATURE:
<221> NAME/KEY: misc_feature

```
<222> LOCATION: 1102
<223> OTHER INFORMATION: n = c or g and different from psition 620
<220> FEATURE:
<221> NAME/KEY: misc_feature
<222> LOCATION: 1229
<223> OTHER INFORMATION: n = c or cg
<220> FEATURE:
<221> NAME/KEY: misc_feature
<222> LOCATION: 1231
<223> OTHER INFORMATION: n = g or cc

<400> SEQUENCE: 34
cgacacatgc ccagacactg cggaaatgcc accttcaggc cgtcgcgtcg gtcccgaatt      60
ggccgtgaac gaccgccgga taagggtttc ggcggtgcgc ttgatgcggg tggacgccca     120
agttgtggtt gactacacga gcactgccgg gcccagcgcc tgcagtctga cctaattcag     180 g atg cgc cca aac atg cat gga tgc gtt gag atg agg atg agg gaa gca    229
  Met Arg Pro Asn Met His Gly Cys Val Glu Met Arg Met Arg Glu Ala
      -55                 -50                 -45 aga atg cag ctt gtt gac agg gtt cgt ggc gcc gtc acg ggt atg tcg     277
Arg Met Gln Leu Val Asp Arg Val Arg Gly Ala Val Thr Gly Met Ser
            -40                 -35                 -30 cgt cga ctc gtg gtc ggg gcc gtc ncg cnc nta gtg tcg ggt ctg gtc     325
Arg Arg Leu Val Val Gly Ala Val Xaa Xaa Xaa Val Ser Gly Leu Val
        -25                 -20                 -15 ggc gcc gtc ggt ggc acg gcg acc gcg ggg gca ttt tcc cgg ccg ggc     373
Gly Ala Val Gly Gly Thr Ala Thr Ala Gly Ala Phe Ser Arg Pro Gly
    -10                 -5                  1                   5 ttg ccg gtg gag tac ctg cag gtg ccg tcg ccg tcg atg ggc cgt gac     421
Leu Pro Val Glu Tyr Leu Gln Val Pro Ser Pro Ser Met Gly Arg Asp
                10                  15                  20 atc aag gtc caa ttc caa agt ggt ggt gcc aac tcg ccc gcc ctg tac     469
Ile Lys Val Gln Phe Gln Ser Gly Gly Ala Asn Ser Pro Ala Leu Tyr
            25                  30                  35 ctg ctc gac ggc ctg cgc gcg cag gac gac ttc agc ggc tgg gac atc     517
Leu Leu Asp Gly Leu Arg Ala Gln Asp Asp Phe Ser Gly Trp Asp Ile
        40                  45                  50 aac acc ccg gcg ttc gag tgg tac gac cag tcg ggc ctg tcg gtg gtc     565
Asn Thr Pro Ala Phe Glu Trp Tyr Asp Gln Ser Gly Leu Ser Val Val
    55                  60                  65 atg ccg gtg ggt ggc cag tca agc ttc tac tcc gac tgg tac cag ccc     613
Met Pro Val Gly Gly Gln Ser Ser Phe Tyr Ser Asp Trp Tyr Gln Pro
70                  75                  80                  85 gcc tgc ngc aag gcc ggt tgc cag act tac aag tgg gag acc ttc ctg     661
Ala Cys Xaa Lys Ala Gly Cys Gln Thr Tyr Lys Trp Glu Thr Phe Leu
                90                  95                  100 acc agc gag ctg ccg ggg tgg ctg cag gcc aac agg cac gtc aag ccc     709
Thr Ser Glu Leu Pro Gly Trp Leu Gln Ala Asn Arg His Val Lys Pro
            105                 110                 115 acc gga agc gcc gtc gtc ggt ctt tcg atg gct gct tct tcg gcg ctg     757
Thr Gly Ser Ala Val Val Gly Leu Ser Met Ala Ala Ser Ser Ala Leu
        120                 125                 130 acg ctg gcg atc tat cac ccc cag cag ttc gtc tac gcg gga gcg atg     805
Thr Leu Ala Ile Tyr His Pro Gln Gln Phe Val Tyr Ala Gly Ala Met
    135                 140                 145 tcg ggc ctg ttg gac ccc tcc cag gcg atg ggt ccc acc ctg atc ggc     853
Ser Gly Leu Leu Asp Pro Ser Gln Ala Met Gly Pro Thr Leu Ile Gly
150                 155                 160                 165 ctg gcg atg ggt gac gct ggc ggc tac aag gcc tcc gac atg tgg ggc     901
Leu Ala Met Gly Asp Ala Gly Gly Tyr Lys Ala Ser Asp Met Trp Gly
                170                 175                 180
```

-continued

```
ccg aag gag gac ccg gcg tgg cag cgc aac gac ccg ctg ttg aac gtc        949
Pro Lys Glu Asp Pro Ala Trp Gln Arg Asn Asp Pro Leu Leu Asn Val
            185                 190                 195 ggg aag ctg atc gcc aac aac acc cgc gtc tgg gtg tac tgc ggc aac        997
Gly Lys Leu Ile Ala Asn Asn Thr Arg Val Trp Val Tyr Cys Gly Asn
        200                 205                 210 ggc aag ccg tcg gat ctg ggt ggc aac aac ctg ccg gcc aag ttc ctc       1045
Gly Lys Pro Ser Asp Leu Gly Gly Asn Asn Leu Pro Ala Lys Phe Leu
    215                 220                 225 gag ggc ttc gtg cgg acc agc aac atc aag ttc caa gac gcc tac aac       1093
Glu Gly Phe Val Arg Thr Ser Asn Ile Lys Phe Gln Asp Ala Tyr Asn
230                 235                 240                 245 gcc ggt ggn ngc cac aac ggc gtg ttc gac ttc ccg gac agc ggt acg       1141
Ala Gly Gly Xaa His Asn Gly Val Phe Asp Phe Pro Asp Ser Gly Thr
                250                 255                 260 cac agc tgg gag tac tgg ggc gcg cag ctc aac gct atg aag ccc gac       1189
His Ser Trp Glu Tyr Trp Gly Ala Gln Leu Asn Ala Met Lys Pro Asp
            265                 270                 275 ctg caa cgn cac tgg gtg cca cgc cca aca ccg ggc ccg ncn cag ggc       1237
Leu Gln Arg His Trp Val Pro Arg Pro Thr Pro Gly Pro Xaa Gln Gly
        280                 285                 290 gcc tagctccgaa cagacacaac atctagcnnc ggtgacccct gtggnncana            1290
Ala tgtttcctaa atcccgtccc tagctcccgc ngcnnccgtg tggttagcta cctgacnnca     1350
tgggttt                                                               1357
```

<210> SEQ ID NO 35
<211> LENGTH: 353
<212> TYPE: PRT
<213> ORGANISM: Mycobacterium tuberculosis
<220> FEATURE:
<221> NAME/KEY: SIGNAL
<222> LOCATION: (1)...(59)
<220> FEATURE:
<221> NAME/KEY: VARIANT
<222> LOCATION: -19, -18
<223> OTHER INFORMATION: Xaa = Ala Arg or Gly Ala Ala
<220> FEATURE:
<221> NAME/KEY: VARIANT
<222> LOCATION: 88, 249
<223> OTHER INFORMATION: Xaa = Arg or Gly
<220> FEATURE:
<221> NAME/KEY: VARIANT
<222> LOCATION: 281-286
<223> OTHER INFORMATION: Xaa = His Trp Val Pro Arg Pro or Ala Leu Gly
    Ala
<220> FEATURE:
<221> NAME/KEY: VARIANT
<222> LOCATION: 288
<223> OTHER INFORMATION: Xaa = Pro or Pro Asn Thr
<220> FEATURE:
<221> NAME/KEY: VARIANT
<222> LOCATION: 291
<223> OTHER INFORMATION: Xaa = Pro or Ala Pro

<400> SEQUENCE: 35

```
Met Arg Pro Asn Met His Gly Cys Val Glu Met Arg Met Arg Glu Ala
            -55                 -50                 -45

Arg Met Gln Leu Val Asp Arg Val Arg Gly Ala Val Thr Gly Met Ser
        -40                 -35                 -30

Arg Arg Leu Val Val Gly Ala Val Xaa Xaa Leu Val Ser Gly Leu Val
    -25                 -20                 -15

Gly Ala Val Gly Gly Thr Ala Thr Ala Gly Ala Phe Ser Arg Pro Gly
-10                 -5                  1                   5
```

-continued

```
Leu Pro Val Glu Tyr Leu Gln Val Pro Ser Pro Ser Met Gly Arg Asp
                 10                  15                  20
Ile Lys Val Gln Phe Gln Ser Gly Gly Ala Asn Ser Pro Ala Leu Tyr
             25                  30                  35
Leu Leu Asp Gly Leu Arg Ala Gln Asp Phe Ser Gly Trp Asp Ile
         40                  45                  50
Asn Thr Pro Ala Phe Glu Trp Tyr Asp Gln Ser Gly Leu Ser Val Val
 55                  60                  65
Met Pro Val Gly Gly Gln Ser Ser Phe Tyr Ser Asp Trp Tyr Gln Pro
 70                  75                  80                  85
Ala Cys Xaa Lys Ala Gly Cys Gln Thr Tyr Lys Trp Glu Thr Phe Leu
                 90                  95                 100
Thr Ser Glu Leu Pro Gly Trp Leu Gln Ala Asn Arg His Val Lys Pro
                105                 110                 115
Thr Gly Ser Ala Val Val Gly Leu Ser Met Ala Ala Ser Ser Ala Leu
                120                 125                 130
Thr Leu Ala Ile Tyr His Pro Gln Gln Phe Val Tyr Ala Gly Ala Met
         135                 140                 145
Ser Gly Leu Leu Asp Pro Ser Gln Ala Met Gly Pro Thr Leu Ile Gly
150                 155                 160                 165
Leu Ala Met Gly Asp Ala Gly Gly Tyr Lys Ala Ser Asp Met Trp Gly
                170                 175                 180
Pro Lys Glu Asp Pro Ala Trp Gln Arg Asn Asp Pro Leu Leu Asn Val
                185                 190                 195
Gly Lys Leu Ile Ala Asn Asn Thr Arg Val Trp Val Tyr Cys Gly Asn
             200                 205                 210
Gly Lys Pro Ser Asp Leu Gly Gly Asn Asn Leu Pro Ala Lys Phe Leu
         215                 220                 225
Glu Gly Phe Val Arg Thr Ser Asn Ile Lys Phe Gln Asp Ala Tyr Asn
230                 235                 240                 245
Ala Gly Gly Xaa His Asn Gly Val Phe Asp Phe Pro Asp Ser Gly Thr
                250                 255                 260
His Ser Trp Glu Tyr Trp Gly Ala Gln Leu Asn Ala Met Lys Pro Asp
                265                 270                 275
Leu Gln Arg Xaa Xaa Xaa Xaa Xaa Xaa Thr Xaa Gly Pro Xaa Gln Gly
             280                 285                 290
Ala
```

<210> SEQ ID NO 36
<211> LENGTH: 1357
<212> TYPE: DNA
<213> ORGANISM: Mycobacterium tuberculosis
<220> FEATURE:
<221> NAME/KEY: CDS
<222> LOCATION: (182)...(1240)
<220> FEATURE:
<221> NAME/KEY: sig_peptide
<222> LOCATION: (182)...(358)
<220> FEATURE:
<221> NAME/KEY: misc_feature
<222> LOCATION: 1268, 1269, 1285, 1286, 1289, 1321, 1324, 1325, 1347, 1348
<223> OTHER INFORMATION: n = a, t, c, or g

<400> SEQUENCE: 36
cgacacatgc ccagacactg cggaaatgcc accttcaggc cgtcgcgtcg gtcccgaatt    60
ggccgtgaac gaccgccgga taagggtttc ggcggtgcgc ttgatgcggg tggacgccca   120

-continued

```
agttgtggtt gactacacga gcactgccgg gcccagcgcc tgcagtctga cctaattcag         180 g atg cgc cca aac atg cat gga tgc gtt gag atg agg atg agg gaa gca         229
  Met Arg Pro Asn Met His Gly Cys Val Glu Met Arg Met Arg Glu Ala
              -55                 -50                 -45 aga atg cag ctt gtt gac agg gtt cgt ggc gcc gtc acg ggt atg tcg           277
Arg Met Gln Leu Val Asp Arg Val Arg Gly Ala Val Thr Gly Met Ser
            -40                 -35                 -30 cgt cga ctc gtg gtc ggg gcc gtc gcg cgc cta gtg tcg ggt ctg gtc           325
Arg Arg Leu Val Val Gly Ala Val Ala Arg Leu Val Ser Gly Leu Val
        -25                 -20                 -15 ggc gcc gtc ggt ggc acg gcg acc gcg ggg gca ttt tcc cgg ccg ggc           373
Gly Ala Val Gly Gly Thr Ala Thr Ala Gly Ala Phe Ser Arg Pro Gly
    -10                  -5                  1                   5 ttg ccg gtg gag tac ctg cag gtg ccg tcg ccg tcg atg ggc cgt gac           421
Leu Pro Val Glu Tyr Leu Gln Val Pro Ser Pro Ser Met Gly Arg Asp
                 10                  15                  20 atc aag gtc caa ttc caa agt ggt ggt gcc aac tcg ccc gcc ctg tac           469
Ile Lys Val Gln Phe Gln Ser Gly Gly Ala Asn Ser Pro Ala Leu Tyr
             25                  30                  35 ctg ctc gac ggc ctg cgc gcg cag gac gac ttc agc ggc tgg gac atc           517
Leu Leu Asp Gly Leu Arg Ala Gln Asp Asp Phe Ser Gly Trp Asp Ile
         40                  45                  50 aac acc ccg gcg ttc gag tgg tac gac cag tcg ggc ctg tcg gtg gtc           565
Asn Thr Pro Ala Phe Glu Trp Tyr Asp Gln Ser Gly Leu Ser Val Val
     55                  60                  65 atg ccg gtg ggt ggc cag tca agc ttc tac tcc gac tgg tac cag ccc           613
Met Pro Val Gly Gly Gln Ser Ser Phe Tyr Ser Asp Trp Tyr Gln Pro
 70                  75                  80                  85 gcc tgc cgc aag gcc ggt tgc cag act tac aag tgg gag acc ttc ctg           661
Ala Cys Arg Lys Ala Gly Cys Gln Thr Tyr Lys Trp Glu Thr Phe Leu
                 90                  95                  100 acc agc gag ctg ccg ggg tgg ctg cag gcc aac agg cac gtc aag ccc           709
Thr Ser Glu Leu Pro Gly Trp Leu Gln Ala Asn Arg His Val Lys Pro
             105                 110                 115 acc gga agc gcc gtc gtc ggt ctt tcg atg gct gct tct tcg gcg ctg           757
Thr Gly Ser Ala Val Val Gly Leu Ser Met Ala Ala Ser Ser Ala Leu
         120                 125                 130 acg ctg gcg atc tat cac ccc cag cag ttc gtc tac gcg gga gcg atg           805
Thr Leu Ala Ile Tyr His Pro Gln Gln Phe Val Tyr Ala Gly Ala Met
     135                 140                 145 tcg ggc ctg ttg gac ccc tcc cag gcg atg ggt ccc acc ctg atc ggc           853
Ser Gly Leu Leu Asp Pro Ser Gln Ala Met Gly Pro Thr Leu Ile Gly
150                 155                 160                 165 ctg gcg atg ggt gac gct ggc ggc tac aag gcc tcc gac atg tgg ggc           901
Leu Ala Met Gly Asp Ala Gly Gly Tyr Lys Ala Ser Asp Met Trp Gly
                 170                 175                 180 ccg aag gag gac ccg gcg tgg cag cgc aac gac ccg ctg ttg aac gtc           949
Pro Lys Glu Asp Pro Ala Trp Gln Arg Asn Asp Pro Leu Leu Asn Val
             185                 190                 195 ggg aag ctg atc gcc aac aac acc cgc gtc tgg gtg tac tgc ggc aac           997
Gly Lys Leu Ile Ala Asn Asn Thr Arg Val Trp Val Tyr Cys Gly Asn
         200                 205                 210 ggc aag ccg tcg gat ctg ggt ggc aac aac ctg ccg gcc aag ttc ctc           1045
Gly Lys Pro Ser Asp Leu Gly Gly Asn Asn Leu Pro Ala Lys Phe Leu
     215                 220                 225 gag ggc ttc gtg cgg acc agc aac atc aag ttc caa gac gcc tac aac           1093
Glu Gly Phe Val Arg Thr Ser Asn Ile Lys Phe Gln Asp Ala Tyr Asn
230                 235                 240                 245 gcc ggt ggg cgc cac aac ggc gtg ttc gac ttc ccg gac agc ggt acg           1141
Ala Gly Gly Arg His Asn Gly Val Phe Asp Phe Pro Asp Ser Gly Thr
```

-continued

```
Ala Gly Gly Arg His Asn Gly Val Phe Asp Phe Pro Asp Ser Gly Thr
                250                 255                 260 cac agc tgg gag tac tgg ggc gcg cag ctc aac gct atg aag ccc gac    1189
His Ser Trp Glu Tyr Trp Gly Ala Gln Leu Asn Ala Met Lys Pro Asp
            265                 270                 275 ctg caa cgg cac tgg gtg cca cgc cca aca ccg ggc ccg ccg cag ggc    1237
Leu Gln Arg His Trp Val Pro Arg Pro Thr Pro Gly Pro Pro Gln Gly
        280                 285                 290 gcc tagctccgaa cagacacaac atctagcnnc ggtgaccctt gtggnncana         1290
Ala tgtttcctaa atcccgtccc tagctcccgc ngcnnccgtg tggttagcta cctgacnnca  1350
tgggttt                                                            1357
```

<210> SEQ ID NO 37
<211> LENGTH: 353
<212> TYPE: PRT
<213> ORGANISM: Mycobacterium tuberculosis
<220> FEATURE:
<221> NAME/KEY: SIGNAL
<222> LOCATION: (1)...(59)

<400> SEQUENCE: 37

```
Met Arg Pro Asn Met His Gly Cys Val Glu Met Arg Met Arg Glu Ala
                -55                 -50                 -45

Arg Met Gln Leu Val Asp Arg Val Arg Gly Ala Val Thr Gly Met Ser
            -40                 -35                 -30

Arg Arg Leu Val Val Gly Ala Val Ala Arg Leu Val Ser Gly Leu Val
        -25                 -20                 -15

Gly Ala Val Gly Gly Thr Ala Thr Ala Gly Ala Phe Ser Arg Pro Gly
    -10                 -5                  1                   5

Leu Pro Val Glu Tyr Leu Gln Val Pro Ser Pro Ser Met Gly Arg Asp
                10                  15                  20

Ile Lys Val Gln Phe Gln Ser Gly Gly Ala Asn Ser Pro Ala Leu Tyr
            25                  30                  35

Leu Leu Asp Gly Leu Arg Ala Gln Asp Asp Phe Ser Gly Trp Asp Ile
        40                  45                  50

Asn Thr Pro Ala Phe Glu Trp Tyr Asp Gln Ser Gly Leu Ser Val Val
    55                  60                  65

Met Pro Val Gly Gly Gln Ser Ser Phe Tyr Ser Asp Trp Tyr Gln Pro
70                  75                  80                  85

Ala Cys Arg Lys Ala Gly Cys Gln Thr Tyr Lys Trp Glu Thr Phe Leu
                90                  95                  100

Thr Ser Glu Leu Pro Gly Trp Leu Gln Ala Asn Arg His Val Lys Pro
            105                 110                 115

Thr Gly Ser Ala Val Val Gly Leu Ser Met Ala Ala Ser Ser Ala Leu
        120                 125                 130

Thr Leu Ala Ile Tyr His Pro Gln Gln Phe Val Tyr Ala Gly Ala Met
    135                 140                 145

Ser Gly Leu Leu Asp Pro Ser Gln Ala Met Gly Pro Thr Leu Ile Gly
150                 155                 160                 165

Leu Ala Met Gly Asp Ala Gly Gly Tyr Lys Ala Ser Asp Met Trp Gly
                170                 175                 180

Pro Lys Glu Asp Pro Ala Trp Gln Arg Asn Asp Pro Leu Leu Asn Val
            185                 190                 195

Gly Lys Leu Ile Ala Asn Asn Thr Arg Val Trp Val Tyr Cys Gly Asn
        200                 205                 210
```

```
Gly Lys Pro Ser Asp Leu Gly Gly Asn Asn Leu Pro Ala Lys Phe Leu
    215                 220                 225

Glu Gly Phe Val Arg Thr Ser Asn Ile Lys Phe Gln Asp Ala Tyr Asn
230                 235                 240                 245

Ala Gly Gly Arg His Asn Gly Val Phe Asp Phe Pro Asp Ser Gly Thr
                250                 255                 260

His Ser Trp Glu Tyr Trp Gly Ala Gln Leu Asn Ala Met Lys Pro Asp
            265                 270                 275

Leu Gln Arg His Trp Val Pro Arg Pro Thr Gly Pro Pro Gln Gly
        280                 285                 290

Ala

<210> SEQ ID NO 38
<211> LENGTH: 1299
<212> TYPE: DNA
<213> ORGANISM: Mycobacterium tuberculosis
<220> FEATURE:
<221> NAME/KEY: CDS
<222> LOCATION: (91)...(1104)
<220> FEATURE:
<221> NAME/KEY: sig_peptide
<222> LOCATION: (91)...(219)

<400> SEQUENCE: 38
actgccgggc ccagcgcctg cagtctgacc taattcagga tgcgcccaaa catgcatgga      60
tgcgttgaga tgaggatgag ggaagcaaga atg cag ctt gtt gac agg gtt cgt     114
                                 Met Gln Leu Val Asp Arg Val Arg
                                                  -40 ggc gcc gtc acg ggt atg tcg cgt cga ctc gtg gtc ggg gcc gtc ggc     162
Gly Ala Val Thr Gly Met Ser Arg Arg Leu Val Val Gly Ala Val Gly
-35                 -30                 -25                 -20 gcg gcc cta gtg tcg ggt ctg gtc ggc gcc gtc ggt ggc acg gcg acc     210
Ala Ala Leu Val Ser Gly Leu Val Gly Ala Val Gly Gly Thr Ala Thr
            -15                 -10                  -5 gcg ggg gca ttt tcc cgg ccg ggc ttg ccg gtg gag tac ctg cag gtg     258
Ala Gly Ala Phe Ser Arg Pro Gly Leu Pro Val Glu Tyr Leu Gln Val
             1                   5                  10 ccg tcg ccg tcg atg ggc cgt gac atc aag gtc caa ttc caa agt ggt     306
Pro Ser Pro Ser Met Gly Arg Asp Ile Lys Val Gln Phe Gln Ser Gly
         15                  20                  25 ggt gcc aac tcg ccc gcc ctg tac ctg ctc gac ggc ctg cgc gcg cag     354
Gly Ala Asn Ser Pro Ala Leu Tyr Leu Leu Asp Gly Leu Arg Ala Gln
 30                  35                  40                  45 gac gac ttc agc ggc tgg gac atc aac acc ccg gcg ttc gag tgg tac     402
Asp Asp Phe Ser Gly Trp Asp Ile Asn Thr Pro Ala Phe Glu Trp Tyr
                 50                  55                  60 gac cag tcg ggc ctg tcg gtg gtc atg ccg gtg ggt ggc cag tca agc     450
Asp Gln Ser Gly Leu Ser Val Val Met Pro Val Gly Gly Gln Ser Ser
             65                  70                  75 ttc tac tcc gac tgg tac cag ccc gcc tgc ggc aag gcc ggt tgc cag     498
Phe Tyr Ser Asp Trp Tyr Gln Pro Ala Cys Gly Lys Ala Gly Cys Gln
         80                  85                  90 act tac aag tgg gag acc ttc ctg acc agc gag ctg ccg ggg tgg ctg     546
Thr Tyr Lys Trp Glu Thr Phe Leu Thr Ser Glu Leu Pro Gly Trp Leu
     95                 100                 105 cag gcc aac agg cac gtc aag ccc acc gga agc gcc gtc gtc ggt ctt     594
Gln Ala Asn Arg His Val Lys Pro Thr Gly Ser Ala Val Val Gly Leu
110                 115                 120                 125 tcg atg gct gct tct tcg gcg ctg acg ctg gcg atc tat cac ccc cag     642
```

```
Ser Met Ala Ala Ser Ser Ala Leu Thr Leu Ala Ile Tyr His Pro Gln
            130                 135                 140 cag ttc gtc tac gcg gga gcg atg tcg ggc ctg ttg gac ccc tcc cag      690
Gln Phe Val Tyr Ala Gly Ala Met Ser Gly Leu Leu Asp Pro Ser Gln
        145                 150                 155 gcg atg ggt ccc acc ctg atc ggc ctg gcg atg ggt gac gct ggc ggc      738
Ala Met Gly Pro Thr Leu Ile Gly Leu Ala Met Gly Asp Ala Gly Gly
        160                 165                 170 tac aag gcc tcc gac atg tgg ggc ccg aag gag gac ccg gcg tgg cag      786
Tyr Lys Ala Ser Asp Met Trp Gly Pro Lys Glu Asp Pro Ala Trp Gln
    175                 180                 185 cgc aac gac ccg ctg ttg aac gtc ggg aag ctg atc gcc aac aac acc      834
Arg Asn Asp Pro Leu Leu Asn Val Gly Lys Leu Ile Ala Asn Asn Thr
190                 195                 200                 205 cgc gtc tgg gtg tac tgc ggc aac ggc aag ccg tcg gat ctg ggt ggc      882
Arg Val Trp Val Tyr Cys Gly Asn Gly Lys Pro Ser Asp Leu Gly Gly
                210                 215                 220 aac aac ctg ccg gcc aag ttc ctc gag ggc ttc gtg cgg acc agc aac      930
Asn Asn Leu Pro Ala Lys Phe Leu Glu Gly Phe Val Arg Thr Ser Asn
                225                 230                 235 atc aag ttc caa gac gcc tac aac gcc ggt ggc ggc cac aac ggc gtg      978
Ile Lys Phe Gln Asp Ala Tyr Asn Ala Gly Gly Gly His Asn Gly Val
        240                 245                 250 ttc gac ttc ccg gac agc ggt acg cac agc tgg gag tac tgg ggc gcg     1026
Phe Asp Phe Pro Asp Ser Gly Thr His Ser Trp Glu Tyr Trp Gly Ala
        255                 260                 265 cag ctc aac gct atg aag ccc gac ctg caa cgg gca ctg ggt gcc acg     1074
Gln Leu Asn Ala Met Lys Pro Asp Leu Gln Arg Ala Leu Gly Ala Thr
270                 275                 280                 285 ccc aac acc ggg ccc gcg ccc cag ggc gcc tagctccgaa cagacacaac       1124
Pro Asn Thr Gly Pro Ala Pro Gln Gly Ala
                290                 295 atctagcggc ggtgacccct gtggtcgccg ccgtagatgt ttcctaaatc ccgtccctag   1184
ctcccgccgc gggccgtgtg gttagctacc tgacgggcta ggggttggcc ggggcggttg   1244
acgccgggtg cacacagcct acacgaacgg aagtggaca catgaagggt cggtc         1299

<210> SEQ ID NO 39
<211> LENGTH: 338
<212> TYPE: PRT
<213> ORGANISM: Mycobacterium tuberculosis
<220> FEATURE:
<221> NAME/KEY: SIGNAL
<222> LOCATION: (1)...(43)

<400> SEQUENCE: 39

Met Gln Leu Val Asp Arg Val Arg Gly Ala Val Thr Gly Met Ser Arg
            -40                 -35                 -30

Arg Leu Val Val Gly Ala Val Gly Ala Ala Leu Val Ser Gly Leu Val
        -25                 -20                 -15

Gly Ala Val Gly Gly Thr Ala Thr Ala Gly Ala Phe Ser Arg Pro Gly
        -10                  -5                   1                   5

Leu Pro Val Glu Tyr Leu Gln Val Pro Ser Pro Ser Met Gly Arg Asp
                10                  15                  20

Ile Lys Val Gln Phe Gln Ser Gly Gly Ala Asn Ser Pro Ala Leu Tyr
            25                  30                  35

Leu Leu Asp Gly Leu Arg Ala Gln Asp Asp Phe Ser Gly Trp Asp Ile
        40                  45                  50

Asn Thr Pro Ala Phe Glu Trp Tyr Asp Gln Ser Gly Leu Ser Val Val
```

```
                    55                  60                  65
Met Pro Val Gly Gly Gln Ser Ser Phe Tyr Ser Asp Trp Tyr Gln Pro
 70                  75                  80                  85

Ala Cys Gly Lys Ala Gly Cys Gln Thr Tyr Lys Trp Glu Thr Phe Leu
                 90                  95                 100

Thr Ser Glu Leu Pro Gly Trp Leu Gln Ala Asn Arg His Val Lys Pro
            105                 110                 115

Thr Gly Ser Ala Val Val Gly Leu Ser Met Ala Ala Ser Ser Ala Leu
        120                 125                 130

Thr Leu Ala Ile Tyr His Pro Gln Gln Phe Val Tyr Ala Gly Ala Met
    135                 140                 145

Ser Gly Leu Leu Asp Pro Ser Gln Ala Met Gly Pro Thr Leu Ile Gly
150                 155                 160                 165

Leu Ala Met Gly Asp Ala Gly Gly Tyr Lys Ala Ser Asp Met Trp Gly
                170                 175                 180

Pro Lys Glu Asp Pro Ala Trp Gln Arg Asn Asp Pro Leu Leu Asn Val
            185                 190                 195

Gly Lys Leu Ile Ala Asn Asn Thr Arg Val Trp Val Tyr Cys Gly Asn
        200                 205                 210

Gly Lys Pro Ser Asp Leu Gly Gly Asn Asn Leu Pro Ala Lys Phe Leu
    215                 220                 225

Glu Gly Phe Val Arg Thr Ser Asn Ile Lys Phe Gln Asp Ala Tyr Asn
230                 235                 240                 245

Ala Gly Gly Gly His Asn Gly Val Phe Asp Phe Pro Asp Ser Gly Thr
                250                 255                 260

His Ser Trp Glu Tyr Trp Gly Ala Gln Leu Asn Ala Met Lys Pro Asp
            265                 270                 275

Leu Gln Arg Ala Leu Gly Ala Thr Pro Asn Thr Gly Pro Ala Pro Gln
        280                 285                 290

Gly Ala
    295

<210> SEQ ID NO 40
<211> LENGTH: 3423
<212> TYPE: DNA
<213> ORGANISM: Artificial Sequence
<220> FEATURE:
<223> OTHER INFORMATION: plasmid vector

<400> SEQUENCE: 40
ttccggggat ctctcaccta ccaaacaatg ccccctgca aaaataaat tcatataaaa      60 aacatacaga taaccatctg cggtgataaa ttatctctgg cggtgttgac ataaatacca    120
ctggcggtga tactgagcac atcagcagga cgcactgacc accatgaagg tgacgctctt    180
aaaaattaag ccctgaagaa gggcaggggt accaggaggt ttaaatcatg gtaagatcaa    240
gtagtcaaaa ttcgagtgac aagcctgtag cccacgtcgt agcaaaccac caagtggagg    300
agcagtaacc atggttactg gagaaggggg accaactcag cgctgaggtc aatctgccca    360
agtctagagt cgacctgcag cccaagcttg gctgttttgg cggatgagag aagattttca    420
gcctgataca gattaaatca gaacgcagaa gcggtctgat aaaacagaat ttgcctggcg    480
gcagtagcgc ggtggtccca cctgacccca tgccgaactc agaagtgaaa cgccgtagcg    540
ccgatggtag tgtggggtct ccccatgcga gagtagggaa ctgccaggca tcaaataaaa    600
cgaaaggctc agtcgaaaga ctgggccttt cgttttatct gttgtttgtc ggtgaacgct    660
```

```
ctcctgagta ggacaaatcc gccgggagcg gatttgaacg ttgcgaagca acggcccgga      720
gggtggcggg caggacgccc gccataaact gccaggcatc aaattaagca gaaggccatc      780
ctgacggatg gcctttttgc gtttctacaa actcttttgt ttattttttct aaatacattc     840 aaatatgtat ccgctcatga gacaataacc ctgataaatg cttcaataat aaaaggatct     900
aggtgaagat cctttttgat aatctcatga ccaaaatccc ttaacgtgag ttttcgttcc      960
actgagcgtc agaccccgta gaaaagatca aaggatcttc ttgagatcct ttttttctgc     1020
gcgtaatctg ctgcttgcaa acaaaaaaac caccgctacc agcggtggtt tgtttgccgg     1080
atcaagagct accaactctt tttccgaagg taactggctt cagcagagcg cagataccaa     1140
atactgtcct tctagtgtag ccgtagttag gccaccactt caagaactct gtagcaccgc     1200
ctacatacct cgctctgcta atcctgttac cagtggctgc tgccagtggc gataagtcgt     1260
gtcttaccgg gttggactca agacgatagt taccggataa ggcgcagcgg tcgggctgaa     1320
cggggggttc gtgcacacag cccagcttgg agcgaacgac ctacaccgaa ctgagatacc     1380
tacagcgtga gcattgagaa agcgccacgc ttcccgaagg gagaaaggcg gacaggtatc     1440
cggtaagcgg cagggtcgga acaggagagc gcacgaggga gcttccaggg ggaaacgcct     1500
ggtatcttta tagtcctgtc gggtttcgcc acctctgact tgagcgtcga ttttgtgat     1560 gctcgtcagg gggcggagc ctatggaaaa acgccagcaa cgcggccttt ttacggttcc     1620
tggccttttg ctggcctttt gctcacatgt tctttcctgc gttatcccct gattctgtgg     1680
ataaccgtat taccgccttt gagtgagctg ataccgctcg ccgcagccga acgaccgagc     1740
gcagcgagtc agtgagcgag gaagcggaag agcgctgact ccgcgtttc cagactttac      1800 gaaacacgga aaccgaagac cattcatgtt gttgctcagg tcgcagacgt tttgcagcag     1860
cagtcgcttc acgttcgctc gcgtatcggt gattcattct gctaaccagt aaggcaaccc     1920
cgccagccta gccgggtcct caacgacagg agcacgatca tgcgcacccg tggccaggac     1980
ccaacgctgc ccgagatgcg ccgcgtgcgg ctgctggaga tggcggacgc gatggatatg     2040
ttctgccaag ggttggtttg cgcattcaca gttctccgca agaattgatt ggctccaatt     2100
cttggagtgg tgaatccgtt agcgaggtgc cgccggcttc cattcaggtc gaggtggccc     2160
ggctccatgc accgcgacgc aacgcgggga ggcagacaag gtatagggcg cgcctacaa     2220 tccatgccaa cccgttccat gtgctcgccg aggcggcata aatcgccgtg acgatcagcg     2280
gtccagtgat cgaagttagg ctggtaagag ccgcgagcga tccttgaagc tgtccctgat     2340
ggtcgtcatc tacctgcctg gacagcatgg cctgcaacgc gggcatcccg atgccgccgg     2400
aagcgagaag aatcataatg gggaaggcca tccagcctcg cgtcgcgaac gccagcaaga     2460
cgtagcccag cgcgtcggcc gccatgccgg cgataatggc ctgcttctcg ccgaaacgtt     2520
tggtggcggg accagtgacg aaggcttgag cgagggcgtg caagattccg aataccgcaa     2580
gcgacaggcc gatcatcgtc gcgctccagc gaaagcggtc ctcgccgaaa atgacccaga     2640
gcgctgccgg cacctgtcct acgagttgca tgataaagaa gacagtcata agtgcggcga     2700
cgatagtcat gccccgcgcc caccggaagg agctgactgg gttgaaggct ctcaagggca     2760
tcggtcgacg ctctccctta tgcgactcct gcattaggaa gcagcccagt agtaggttga     2820
ggccgttgag caccgccgcc gcaaggaatg gtgcatgcaa ggagatgcg cccaacagtc      2880 ccccggccac ggggcctgcc accatacccca cgccgaaaca agcgctcatg agcccgaagt     2940
ggcgagcccg atcttcccca tcggtgatgt cggcgatata ggcgccagca accgcacctg     3000
tggcgccggt gatgccggcc acgatgcgtc cggcgtagag gatccacagg acgggtgtgg     3060
```

```
tcgccatgat cgcgtagtcg atagtggctc caagtagcga agcgagcagg actgggcggc    3120
ggccaaagcg gtcggacagt gctccgagaa cgggtgcgca tagaaattgc atcaacgcat    3180
atagcgctag cagcacgcca tagtgactgg cgatgctgtc ggaatggacg atatcccgca    3240
agaggcccgg cagtaccggc ataaccaagc ctatgcctac agcatccagg gtgacggtgc    3300
cgaggatgac gatgagcgca ttgttagatt tcatacacgg tgcctgactg cgttagcaat    3360
ttaactgtga taaactaccg cattaaagct tatcgatgat aagctgtcaa acatgagaat    3420
taa                                                                 3423

<210> SEQ ID NO 41
<211> LENGTH: 3474
<212> TYPE: DNA
<213> ORGANISM: Artificial Sequence
<220> FEATURE:
<223> OTHER INFORMATION: plasmid vector

<400> SEQUENCE: 41
aattccgggg atctctcacc taccaaacaa tgcccccctg caaaaaataa attcatataa      60
aaaacataca gataaccatc tgcggtgata aattatctct ggcggtgttg acataaatac     120
cactggcggt gatactgagc acatcagcag gacgcactga ccaccatgaa ggtgacgctc     180
ttaaaaatta gccctgaag aagggcaggg gtaccaggag gtttaaatca tggtaagatc     240
aagtagtcaa aattcgagtg acaagcctgt agcccacgtc gtagcaaacc accaagtgga     300
ggagcaggga attcaccatc accatcacca cgtggatccc gggcccatgg ctttccggag     360
gcctctagag tcgaccggca tgcaagctta agtaagtaag ccgccagttc cgctggcggc     420
attttttttg atgcccaagc ttggctgttt tggcggatga gagaagattt tcagcctgat     480
acagattaaa tcagaacgca gaagcggtct gataaaacag aatttgcctg gcggcagtag     540
cgcggtggtc ccacctgacc ccatgccgaa ctcagaagtg aaacgccgta gcgccgatgg     600
tagtgtgggg tctccccatg cgagagtagg gaactgccag gcatcaaata aaacgaaagg     660
ctcagtcgaa agactgggcc tttcgtttta tctgttgttt gtcggtgaac gctctcctga     720
gtaggacaaa tccgccggga gcggatttga acgttgcgaa gcaacggccc ggagggtggc     780
gggcaggacg cccgccataa actgccaggc atcaaattaa gcagaaggcc atcctgacgg     840 atggccttttt tgcgtttcta caaactcttt tgtttatttt tctaaataca ttcaaatatg     900
tatccgctca tgagacaata accctgataa atgcttcaat aataaaagga tctaggtgaa     960
gatccttttt gataatctca tgaccaaaat cccttaacgt gagttttcgt tccactgagc    1020
gtcagacccc gtagaaaaga tcaaaggatc ttcttgagat ccttttttc tgcgcgtaat    1080 ctgctgcttg caaacaaaaa accaccgct accagcggtg gtttgtttgc cggatcaaga    1140
gctaccaact cttttccga aggtaactgg cttcagcaga gcgcagatac caaatactgt    1200
ccttctagtg tagccgtagt taggccacca cttcaagaac tctgtagcac cgcctacata    1260
cctcgctctg ctaatcctgt taccagtggc tgctgccagt ggcgataagt cgtgtcttac    1320
cgggttggac tcaagacgat agttaccgga taaggcgcag cggtcgggct gaacggggggg    1380 ttcgtgcaca cagcccagct tggagcgaac gacctacacc gaactgagat acctacagcg    1440
tgagcattga gaaagcgcca cgcttcccga agggagaaag gcggacaggt atccggtaag    1500
cggcagggtc ggaacaggag agcgcacgag ggagcttcca gggggaaacg cctggtatct    1560
ttatagtcct gtcgggtttc gccacctctg acttgagcgt cgatttttgt gatgctcgtc    1620
```

```
aggggggcgg agcctatgga aaaacgccag caacgcggcc ttttacggt tcctggcctt      1680 ttgctggcct tttgctcaca tgttctttcc tgcgttatcc cctgattctg tggataaccg      1740
tattaccgcc tttgagtgag ctgataccgc tcgccgcagc cgaacgaccg agcgcagcga      1800
gtcagtgagc gaggaagcgg aagagcgctg acttccgcgt ttccagactt tacgaaacac      1860
ggaaaccgaa gaccattcat gttgttgctc aggtcgcaga cgttttgcag cagcagtcgc      1920
ttcacgttcg ctcgcgtatc ggtgattcat tctgctaacc agtaaggcaa ccccgccagc      1980
ctagccgggt cctcaacgac aggagcacga tcatgcgcac ccgtggccag gacccaacgc      2040
tgcccgagat gcgccgcgtg cggctgctgg agatggcgga cgcgatggat atgttctgcc      2100
aagggttggt ttgcgcattc acagttctcc gcaagaattg attggctcca attcttggag      2160
tggtgaatcc gttagcgagg tgccgccggc ttccattcag gtcgaggtgg cccggctcca      2220
tgcaccgcga cgcaacgcgg ggaggcagac aaggtatagg gcggcgccta caatccatgc      2280
caacccgttc catgtgctcg ccgaggcggc ataaatcgcc gtgacgatca gcggtccagt      2340
gatcgaagtt aggctggtaa gagccgcgag cgatccttga agctgtccct gatggtcgtc      2400
atctacctgc ctggacagca tggcctgcaa cgcgggcatc ccgatgccgc cggaagcgag      2460
aagaatcata atggggaagg ccatccagcc tcgcgtcgcg aacgccagca agacgtagcc      2520
cagcgcgtcg gccgccatgc cggcgataat ggcctgcttc tcgccgaaac gtttggtggc      2580
gggaccagtg acgaaggctt gagcgagggc gtgcaagatt ccgaataccg caagcgacag      2640
gccgatcatc gtcgcgctcc agcgaaagcg gtcctcgccg aaaatgaccc agagcgctgc      2700
cggcacctgt cctacgagtt gcatgataaa gaagacagtc ataagtgcgg cgacgatagt      2760
catgccccgc gcccaccgga aggagctgac tgggttgaag gctctcaagg gcatcggtcg      2820
acgctctccc ttatgcgact cctgcattag gaagcagccc agtagtaggt tgaggccgtt      2880
gagcaccgcc gccgcaagga atggtgcatg caaggagatg gcgcccaaca gtcccccggc      2940 cacgggcct gccaccatac ccacgccgaa acaagcgctc atgagcccga agtggcgagc      3000
ccgatcttcc ccatcggtga tgtcggcgat ataggcgcca gcaaccgcac ctgtggcgcc      3060
ggtgatgccg gccacgatgc gtccggcgta gaggatccac aggacgggtg tggtcgccat      3120
gatcgcgtag tcgatagtgg ctccaagtag cgaagcgagc aggactgggc ggcggccaaa      3180
gcggtcggac agtgctccga gaacgggtgc gcatagaaat tgcatcaacg catatagcgc      3240
tagcagcacg ccatagtgac tggcgatgct gtcggaatgg acgatatccc gcaagaggcc      3300
cggcagtacc ggcataacca agcctatgcc tacagcatcc agggtgacgg tgccgaggat      3360
gacgatgagc gcattgttag atttcataca cggtgcctga ctgcgttagc aatttaactg      3420
tgataaacta ccgcattaaa gcttatcgat gataagctgt caaacatgag aatt            3474
```

<210> SEQ ID NO 42
<211> LENGTH: 3301
<212> TYPE: DNA
<213> ORGANISM: Artificial Sequence
<220> FEATURE:
<223> OTHER INFORMATION: plasmid vector

<400> SEQUENCE: 42

```
ttccggggat ctctcaccta ccaaacaatg cccccctgca aaaataaat tcatataaaa        60 aacatacaga taaccatctg cggtgataaa ttatctctgg cggtgttgac ataaatacca      120
ctggcggtga tactgagcac atcagcagga cgcactgacc accatgaagg tgacgctctt      180
aaaaattaag ccctgaagaa gggcagggt accaggaggt ttaaatattc catggggggg      240
```

-continued

```
atcctctaga gtcgacctgc agcccaagct tggctgtttt ggcggatgag agaagatttt      300
cagcctgata cagattaaat cagaacgcag aagcggtctg ataaaacaga atttgcctgg      360
cggcagtagc gcggtggtcc cacctgaccc catgccgaac tcagaagtga aacgccgtag      420
cgccgatggt agtgtggggt ctccccatgc gagagtaggg aactgccagg catcaaataa      480
aacgaaaggc tcagtcgaaa gactgggcct ttcgttttat ctgttgtttg tcggtgaacg      540
ctctcctgag taggacaaat ccgccgggag cggatttgaa cgttgcgaag caacggcccg      600
gagggtggcg ggcaggacgc ccgccataaa ctgccaggca tcaaattaag cagaaggcca      660
tcctgacgga tggccttttt gcgtttctac aaactctttt gtttattttt ctaaatacat      720
tcaaatatgt atccgctcat gagacaataa ccctgataaa tgcttcaata ataaaaggat      780
ctaggtgaag atccttttg ataatctcat gaccaaaatc ccttaacgtg agttttcgtt      840
ccactgagcg tcagaccccg tagaaaagat caaaggatct tcttgagatc ctttttttct      900
gcgcgtaatc tgctgcttgc aaacaaaaaa accaccgcta ccagcggtgg tttgtttgcc      960
ggatcaagag ctaccaactc tttttccgaa ggtaactggc ttcagcagag cgcagatacc     1020
aaatactgtc cttctagtgt agccgtagtt aggccaccac ttcaagaact ctgtagcacc     1080
gcctacatac ctcgctctgc taatcctgtt accagtggct gctgccagtg gcgataagtc     1140
gtgtcttacc gggttggact caagacgata gttaccggat aaggcgcagc ggtcgggctg     1200
aacgggggt tcgtgcacac agcccagctt ggagcgaacg acctacaccg aactgagata     1260
cctacagcgt gagcattgag aaagcgccac gcttcccgaa gggagaaagg cggacaggta     1320
tccggtaagc ggcagggtcg gaacaggaga gcgcacgagg gagcttccag ggggaaacgc     1380
ctggtatctt tatagtcctg tcgggtttcg ccacctctga cttgagcgtc gatttttgtg     1440
atgctcgtca gggggcgga gcctatggaa aaacgccagc aacgcggcct ttttacggtt     1500
cctggccttt tgctggcctt tgctcacat gttctttcct gcgttatccc ctgattctgt     1560
ggataaccgt attaccgcct ttgagtgagc tgataccgct cgccgcagcc gaacgaccga     1620
gcgcagcgag tcagtgagcg aggaagcgga agagcgctga cttccgcgtt tccagacttt     1680
acgaaacacg gaaaccgaag accattcatg ttgttgctca ggtcgcagac gttttgcagc     1740
agcagtcgct tcacgttcgc tcgcgtatcg gtgattcatt ctgctaacca gtaaggcaac     1800
cccgccagcc tagccgggtc ctcaacgaca ggagcacgat catgcgcacc cgtggccagg     1860
acccaacgct gcccgagatg cgccgcgtgc ggctgctgga gatggcggac gcgatggata     1920
tgttctgcca agggttggtt tgcgcattca cagttctccg caagaattga ttggctccaa     1980
ttcttggagt ggtgaatccg ttagcgaggt gccgccggct tccattcagg tcgaggtggc     2040
ccggctccat gcaccgcgac gcaacgcggg gaggcagaca aggtataggg cggcgcctac     2100
aatccatgcc aacccgttcc atgtgctcgc cgaggcggca taaatcgccg tgacgatcag     2160
cggtccagtg atcgaagtta ggctggtaag agccgcgagc gatccttgaa gctgtccctg     2220
atggtcgtca tctacctgcc tggacagcat ggcctgcaac gcgggcatcc cgatgccgcc     2280
ggaagcgaga agaatcataa tggggaaggc catccagcct cgcgtcgcga acgccagcaa     2340
gacgtagccc agcgcgtcgg ccgccatgcc ggcgataatg gcctgcttct cgccgaaacg     2400
tttggtggcg ggaccagtga cgaaggcttg agcgagggcg tgcaagattc cgaataccgc     2460
aagcgacagg ccgatcatcg tcgcgctcca gcgaaagcgg tcctcgccga aaatgaccca     2520
gagcgctgcc ggcacctgtc ctacgagttg catgataaag aagacagtca taagtgcggc     2580
```

```
gacgatagtc atgccccgcg cccaccggaa ggagctgact gggttgaagg ctctcaaggg    2640
catcggtcga cgctctccct tatgcgactc ctgcattagg aagcagccca gtagtaggtt    2700
gaggccgttg agcaccgccg ccgcaaggaa tggtgcatgc aaggagatgg cgcccaacag    2760
tcccccggcc acgggcctg  ccaccatacc cacgccgaaa caagcgctca tgagcccgaa    2820
gtggcgagcc cgatcttccc catcggtgat gtcggcgata taggcgccag caaccgcacc    2880
tgtggcgccg tgatgccgg  ccacgatgcg tccggcgtag aggatccaca ggacgggtgt    2940
ggtcgccatg atcgcgtagt cgatagtggc tccaagtagc gaagcgagca ggactgggcg    3000
gcggccaaag cggtcggaca gtgctccgag aacgggtgcg catagaaatt gcatcaacgc    3060
atatagcgct agcagcacgc catagtgact ggcgatgctg tcggaatgga cgatatcccg    3120
caagaggccc ggcagtaccg gcataaccaa gcctatgcct acagcatcca gggtgacggt    3180
gccgaggatg acgatgagcg cattgttaga tttcatacac ggtgcctgac tgcgttagca    3240
atttaactgt gataaactac cgcattaaag cttatcgatg ataagctgtc aaacatgaga    3300
a                                                                    3301
```

<210> SEQ ID NO 43
<211> LENGTH: 338
<212> TYPE: PRT
<213> ORGANISM: Artificial Sequence
<220> FEATURE:
<223> OTHER INFORMATION: Synthetically generated peptide

<400> SEQUENCE: 43

```
Met Val Arg Ser Ser Gln Asn Ser Ser Asp Lys Pro Val Ala His
 1               5                  10                  15

Val Val Ala Asn His Gln Val Glu Glu Gln Gly Ile His His His
            20                  25                  30

His His Val Asp Pro Gly Pro Met Ala Phe Arg Arg His Gly Pro Gly
        35                  40                  45

Leu Pro Val Glu Tyr Leu Gln Val Pro Ser Pro Ser Met Gly Arg Asp
 50                  55                  60

Ile Lys Val Gln Phe Gln Ser Gly Gly Ala Asn Ser Pro Ala Leu Tyr
 65                  70                  75                  80

Leu Leu Asp Gly Leu Arg Ala Gln Asp Phe Ser Gly Trp Asp Ile
                85                  90                  95

Asn Thr Pro Ala Phe Glu Trp Tyr Asp Gln Ser Gly Leu Ser Val Val
                    100                 105                 110

Met Pro Val Gly Gly Gln Ser Ser Phe Tyr Ser Asp Trp Tyr Gln Pro
            115                 120                 125

Ala Cys Gly Lys Ala Gly Cys Gln Thr Tyr Lys Trp Glu Thr Phe Leu
        130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
                    180                 185                 190

Ser Gly Leu Leu Asp Pro Ser Gln Ala Met Gly Pro Thr Leu Ile Gly
            195                 200                 205

Leu Ala Met Gly Asp Ala Gly Gly Tyr Lys Ala Ser Asp Met Trp Gly
        210                 215                 220

Pro Lys Glu Asp Pro Ala Trp Gln Arg Asn Asp Pro Leu Leu Asn Val
```

```
                     225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Glu
                325                 330                 335

Gly Ala

<210> SEQ ID NO 44
<211> LENGTH: 324
<212> TYPE: PRT
<213> ORGANISM: Mycobacterium tuberculosis

<400> SEQUENCE: 44

Val Asp Arg Val Arg Gly Ala Val Thr Gly Met Ser Arg Arg Leu Val
1               5                   10                  15

Val Gly Ala Val Gly Ala Ala Leu Val Ser Gly Leu Val Gly Ala Val
                20                  25                  30

Gly Gly Thr Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
    50                  55                  60

Gln Phe Gln Ser Gly Gly Ala Asn Ser Pro Ala Leu Tyr Leu Leu Asp
65                  70                  75                  80

Gly Leu Arg Ala Gln Asp Asp Phe Ser Gly Trp Asp Ile Asn Thr Pro
                85                  90                  95

Ala Phe Glu Trp Tyr Asp Gln Ser Gly Leu Ser Val Val Met Pro Val
            100                 105                 110

Gly Gly Gln Ser Ser Phe Tyr Ser Asp Trp Tyr Gln Pro Ala Cys Gly
        115                 120                 125

Lys Ala Gly Cys Gln Thr Tyr Lys Trp Glu Thr Phe Leu Thr Ser Glu
130                 135                 140

Leu Pro Gly Trp Leu Gln Ala Asn Arg His Val Lys Pro Thr Gly Ser
145                 150                 155                 160

Ala Val Val Gly Leu Ser Met Ala Ala Ser Ser Ala Leu Thr Leu Ala
                165                 170                 175

Ile Tyr His Pro Gln Gln Phe Val Tyr Ala Gly Ala Met Ser Gly Leu
            180                 185                 190

Leu Asp Pro Ser Gln Ala Met Gly Pro Thr Leu Ile Gly Leu Ala Met
        195                 200                 205

Gly Asp Ala Gly Gly Tyr Lys Ala Ser Asp Met Trp Gly Pro Lys Glu
    210                 215                 220

Asp Pro Ala Trp Gln Arg Asn Asp Pro Leu Leu Asn Val Gly Lys Leu
225                 230                 235                 240

Ile Ala Asn Asn Thr Arg Val Trp Val Tyr Cys Gly Asn Gly Lys Pro
                245                 250                 255

Ser Asp Leu Gly Gly Asn Asn Leu Pro Ala Lys Phe Leu Glu Gly Phe
```

```
                        260                 265                 270
Val Arg Thr Ser Asn Ile Lys Phe Gln Asp Ala Tyr Asn Ala Gly Gly
            275                 280                 285
Gly His Asn Gly Val Phe Asp Phe Pro Asp Ser Gly Thr His Ser Trp
    290                 295                 300
Glu Tyr Trp Gly Ala Gln Leu Asn Ala Met Lys Pro Asp Leu Gln Arg
305                 310                 315                 320
Ala Leu Gly Ala

<210> SEQ ID NO 45
<211> LENGTH: 324
<212> TYPE: PRT
<213> ORGANISM: Mycobacterium bovis

<400> SEQUENCE: 45

Met Thr Asp Val Ser Arg Lys Ile Arg Ala Trp Gly Arg Arg Leu Met
1               5

Ser Leu Gly Ala

<210> SEQ ID NO 46
<211> LENGTH: 1017
<212> TYPE: DNA
<213> ORGANISM: Mycobacterium tuberculosis

<400> SEQUENCE: 46

| | | | | |
|---|---|---|---|---|
| atgcagcttg | ttgacagggt | tcgtggcgcc | gtcacgggta | tgtcgcgtcg actcgtggtc | 60 |
| ggggccgtcg | gcgcggccct | agtgtcgggt | ctggtcggcg | ccgtcggtgg cacggcgacc | 120 |
| gcggggcat | tttcccggcc | gggcttgccg | gtggagtacc | tgcaggtgcc gtcgccgtcg | 180 |
| atgggccgtg | acatcaaggt | ccaattccaa | agtggtggtg | ccaactcgcc cgccctgtac | 240 |
| ctgctcgacg | gcctgcgcgc | gcaggacgac | ttcagcggct | gggacatcaa caccccggcg | 300 |
| ttcgagtggt | acgaccagtc | gggcctgtcg | gtggtcatgc | cggtgggtgg ccagtcaagc | 360 |
| ttctactccg | actggtacca | gcccgcctgc | ggcaaggccg | gttgccagac ttacaagtgg | 420 |
| gagaccttcc | tgaccagcga | gctgccgggg | tggctgcagg | ccaacaggca cgtcaagccc | 480 |
| accggaagcg | ccgtcgtcgg | tctttcgatg | gctgcttctt | cggcgctgac gctggcgatc | 540 |
| tatcaccccc | agcagttcgt | ctacgcggga | gcgatgtcgg | gcctgttgga ccctccccag | 600 |
| gcgatgggtc | ccaccctgat | cggcctggcg | atgggtgacg | ctgcggcta caaggcctcc | 660 |
| gacatgtggg | gcccgaagga | ggacccgcg | tggcagcgca | acgacccgct gttgaacgtc | 720 |
| gggaagctga | tcgccaacaa | caccccgcgtc | tgggtgtact | gcggcaacgg caagccgtcg | 780 |
| gatctgggtg | caacaaacct | gccggccaag | ttcctcgagg | gcttcgtgcg gaccagcaac | 840 |
| atcaagttcc | aagacgccta | caacgccggt | ggcggccaca | acggcgtgtt cgacttcccg | 900 |
| gacagcggta | cgcacagctg | ggagtactgg | ggcgcgcagc | tcaacgctat gaagcccgac | 960 |
| ctgcaacggg | cactgggtgc | cacgcccaac | accgggcccg | cgccccaggg cgcctag | 1017 |

<210> SEQ ID NO 47
<211> LENGTH: 1011
<212> TYPE: DNA
<213> ORGANISM: Mycobacterium tuberculosis

<400> SEQUENCE: 47

| | | | | |
|---|---|---|---|---|
| atgcagcttg | ttgacagggt | tcgtggcgcc | gtcacgggta | tgtcgcgtcg actcgtggtc | 60 |
| ggggccgtcg | cgcgcctagt | gtcgggtctg | gtcggcgccg | tcggtggcac ggcgaccgcg | 120 |
| ggggcatttt | cccggccggg | cttgccggtg | gagtacctgc | aggtgccgtc gccgtcgatg | 180 |
| ggccgtgaca | tcaaggtcca | attccaaagt | ggtggtgcca | actcgccgc cctgtacctg | 240 |
| ctcgacggcc | tgcgcgcgca | ggacgacttc | agcggctggg | acatcaacac cccggcgttc | 300 |
| gagtggtacg | accagtcggg | cctgtcgtg | gtcatgccgg | tgggtggcca gtcaagcttc | 360 |
| tactccgact | ggtaccagcc | cgcctgccgc | aaggccggtt | gccagactta caagtgggag | 420 |
| accttcctga | ccagcgagct | gccggggtgg | ctgcaggcca | acaggcacgt caagcccacc | 480 |
| ggaagcgccg | tcgtcggtct | ttcgatggct | gcttcttcgg | cgctgacgct ggcgatctat | 540 |
| caccccagc | agttcgtcta | cgcggagcg | atgtcgggcc | tgttggaccc ctcccaggcg | 600 |
| atgggtccca | ccctgatcgg | cctggcgatg | ggtgacgctg | cggctacaa ggcctccgac | 660 |
| atgtggggcc | cgaaggagga | cccggcgtgg | cagcgcaacg | accgctgtt gaacgtcggg | 720 |
| aagctgatcg | ccaacaacac | ccgcgtctgg | gtgtactgcg | gcaacggcaa gccgtcggat | 780 | ctgggtggca acaacctgcc ggccaagttc ctcgagggct tcgtgcggac cagcaacatc 840 aagttccaag acgcctacaa cgccggtggg cgccacaacg gcgtgttcga cttcccggac 900 agcggtacgc acagctggga gtactggggc gcgcagctca acgctatgaa gcccgacctg 960 caacggcact gggtgccacg cccaacaccg ggcccgccgc agggcgccta g 1011

<210> SEQ ID NO 48
<211> LENGTH: 972
<212> TYPE: DNA
<213> ORGANISM: Mycobacterium bovis

<400> SEQUENCE: 48
atgacagacg tgagccgaaa gattcgagct tggggacgcc gattgatgat cggcacggca 60
gcggctgtag tccttccggg cctggtgggg cttgccggcg gagcggcaac cgcgggcgcg 120
ttctcccggc cggggctgcc ggtcgagtac ctgcaggtgc cgtcgccgtc gatgggccgc 180
gacatcaagg ttcagttcca gagcggtggg aacaactcac ctgcggttta tctgctcgac 240
ggcctgcgcg cccaagacga ctacaacggc tgggatatca acaccccggc gttcgagtgg 300
tactaccagt cgggactgtc gatagtcatg ccggtcggcg ggcagtccag cttctacagc 360
gactggtaca gcccggcctg cggtaaggct ggctgccaga cttacaagtg ggaaaccctc 420
ctgaccagcg agctgccgca atggttgtcc gccaacaggg ccgtgaagcc caccggcagc 480
gctgcaatcg gcttgtcgat ggccggctcg tcggcaatga tcttggccgc ctaccacccc 540
cagcagttca tctacgccgg ctcgctgtcg gccctgctgg acccctctca ggggatgggc 600
ctgatcggcc tcgcgatggg tgacgccggc ggttacaagg ccgcagacat gtggggtccc 660
tcgagtgacc cggcatggga gcgcaacgac cctacgcagc agatccccaa gctggtcgca 720
aacaacaccc ggctatgggt ttattgcggg aacggcaccc cgaacgagtt gggcggtgcc 780
aacatacccg ccgagttctt ggagaacttc gttcgtagca gcaacctgaa gttccaggat 840
gcgtacaagc ccgcgggcgg gcacaacgcc gtgttcaact tcccgcccaa cggcacgcac 900
agctgggagt actggggcgc tcagctcaac gccatgaagg gtgacctgca gagttcgtta 960
ggcgccggct ga 972

<210> SEQ ID NO 49
<211> LENGTH: 6
<212> TYPE: PRT
<213> ORGANISM: Mycobacterium bovis

<400> SEQUENCE: 49

Phe Ser Arg Pro Gly Leu
1 5

<210> SEQ ID NO 50
<211> LENGTH: 30
<212> TYPE: DNA
<213> ORGANISM: Artificial Sequence
<220> FEATURE:
<223> OTHER INFORMATION: Synthetically generared oliginucleotide

<400> SEQUENCE: 50
caagtggagg agcagtaacc atggttactg 30

<210> SEQ ID NO 51
<211> LENGTH: 60
<212> TYPE: DNA
<213> ORGANISM: Artificial Sequence

```
-continued

<220> FEATURE:
<223> OTHER INFORMATION: Synthetically generared oliginucleotide
<220> FEATURE:
<221> NAME/KEY: CDS
<222> LOCATION: (1)...(60)

<400> SEQUENCE: 51 cag gga att cac cat cac cat cac cac gtg gat ccc ggg ccc atg gct      48
Gln Gly Ile His His His His His His Val Asp Pro Gly Pro Met Ala
 1               5                  10                  15 ttc cgg agg cct                                                      60
Phe Arg Arg Pro
         20

<210> SEQ ID NO 52
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 52

Gln Gly Ile His His His His His His Val Asp Pro Gly Pro Met Ala
 1               5                  10                  15

Phe Arg Arg Pro
         20

<210> SEQ ID NO 53
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 53
ggtaccagga ggtttattcc atgg                                           24
```